United States Patent
Opstelten et al.

(10) Patent No.: US 7,297,680 B2
(45) Date of Patent: *Nov. 20, 2007

(54) COMPOSITIONS OF ERYTHROPOIETIN ISOFORMS COMPRISING LEWIS-X STRUCTURES AND HIGH SIALIC ACID CONTENT

(75) Inventors: Dirk J. E. Opstelten, Oegstgeest (NL); Alphonsus G. C. M. UytdeHaag, Vleuten (NL)

(73) Assignee: Crucell Holland B.V., Leiden (NL)

( * ) Notice: Subject to any disclaimer, the term of this patent is extended or adjusted under 35 U.S.C. 154(b) by 0 days.

This patent is subject to a terminal disclaimer.

(21) Appl. No.: 11/102,073

(22) Filed: Apr. 8, 2005

(65) Prior Publication Data

US 2005/0181359 A1 Aug. 18, 2005

Related U.S. Application Data

(63) Continuation-in-part of application No. 11/026,518, filed on Dec. 30, 2004, which is a continuation-in-part of application No. 10/497,832, filed as application No. PCT/NL02/00804 on Dec. 9, 2002, and a continuation-in-part of application No. 09/549,463, filed on Apr. 14, 2000, now Pat. No. 6,855,544, said application No. 11/102,073 is a continuation-in-part of application No. 10/494,140, filed as application No. PCT/NL02/00686 on Oct. 29, 2002.

(60) Provisional application No. 60/129,452, filed on Apr. 15, 1999.

(51) Int. Cl.
| | |
|---|---|
| *A61K 38/17* | (2006.01) |
| *A61K 35/18* | (2006.01) |
| *A61K 38/14* | (2006.01) |
| *A61K 38/19* | (2006.01) |
| *A61K 31/715* | (2006.01) |

(52) U.S. Cl. ............................. 514/12; 530/380; 514/61

(58) Field of Classification Search ...................... None
See application file for complete search history.

(56) References Cited

U.S. PATENT DOCUMENTS

| 4,703,008 A | 10/1987 | Lin |
| 4,835,260 A | 5/1989 | Shoemaker |
| 5,047,335 A | 9/1991 | Paulson et al. |

(Continued)

FOREIGN PATENT DOCUMENTS

| EP | 0 185 573 | 6/1986 |

(Continued)

OTHER PUBLICATIONS

Yatsiv et al., Erythropoietin is Neuroprotective, Improves Functional Recovery, and Reduces Neuronal Apoptosis and Inflammation in a Rodent Model of Experimental Closed Head Injury, Faseb J., 2005, vol. 19, pp. 1701-1703.*

(Continued)

*Primary Examiner*—Rebecca E. Prouty
*Assistant Examiner*—Rosanne Kosson
(74) *Attorney, Agent, or Firm*—TraskBritt

(57) ABSTRACT

Disclosed are immortalized human embryonic retina cells, having a nucleic acid sequence encoding an adenoviral E1A protein integrated into the genome of the cells, and further comprising a nucleic acid sequence encoding an enzyme involved in post-translational modification of proteins, such as a sialyltransferase, wherein said nucleic acid sequence encoding the enzyme involved in post-translational modification of proteins is under control of a heterologous promoter. Methods for producing recombinant proteins from such cells and obtaining such recombinant proteins having increased sialylation are provided as are novel compositions of isoforms of erythropoietin.

26 Claims, 22 Drawing Sheets

PER.C6-EPO

PER.C6-ST-EPO

U.S. PATENT DOCUMENTS

| | | | |
|---|---|---|---|
| 5,192,539 | A | 3/1993 | Van Der Marel et al. |
| 5,441,868 | A | 8/1995 | Lin |
| 5,457,089 | A | 10/1995 | Fibi et al. |
| 5,494,790 | A | 2/1996 | Sasaki et al. |
| 5,518,913 | A | 5/1996 | Massie et al. |
| 5,631,158 | A | 5/1997 | Dorai et al. |
| 5,714,587 | A * | 2/1998 | Laine .......................... 530/395 |
| 5,767,078 | A | 6/1998 | Johnson et al. |
| 5,773,569 | A | 6/1998 | Wrighton et al. |
| 5,789,247 | A | 8/1998 | Ballay et al. |
| 5,830,851 | A | 11/1998 | Wrighton et al. |
| 5,835,382 | A | 11/1998 | Wilson et al. |
| 5,856,292 | A | 1/1999 | Thomas et al. |
| 5,856,298 | A | 1/1999 | Strickland |
| 5,994,128 | A | 11/1999 | Fallaux et al. |
| 6,033,908 | A | 3/2000 | Bout et al. |
| 6,395,519 | B1 | 5/2002 | Fallaux et al. |
| 6,413,746 | B1 | 7/2002 | Field |
| 6,475,753 | B1 | 11/2002 | Ruben et al. |
| 6,492,169 | B1 | 12/2002 | Vogels et al. |
| 6,506,598 | B1 | 1/2003 | Andersen et al. |
| 6,558,948 | B1 | 5/2003 | Kochanek et al. |
| 6,653,101 | B1 | 11/2003 | Cockett et al. |
| 6,855,544 | B1 | 2/2005 | Hateboer et al. |
| 6,878,549 | B1 | 4/2005 | Vogels et al. |
| 7,125,706 | B2 | 10/2006 | Zhang et al. |
| 2002/0116723 | A1 | 8/2002 | Grigliatti et al. |
| 2002/0182723 | A1 | 12/2002 | Zhang et al. |
| 2003/0087437 | A1 | 5/2003 | Asada et al. |
| 2003/0092160 | A1 | 5/2003 | Bout et al. |
| 2005/0170398 | A1 | 8/2005 | Van Berkel et al. |

FOREIGN PATENT DOCUMENTS

| | | |
|---|---|---|
| EP | 0 411 678 | 2/1991 |
| EP | 0 833 934 B1 | 4/1998 |
| EP | 1 108 787 A2 | 6/2001 |
| WO | WO 93/03163 | 2/1993 |
| WO | WO 95/05465 | 2/1995 |
| WO | WO 95/29994 | 11/1995 |
| WO | WO 97/00326 | 1/1997 |
| WO | WO 97/18318 | 5/1997 |
| WO | WO 98/18926 | 5/1998 |
| WO | WO 98/39411 | 9/1998 |
| WO | WO 98/44141 | 10/1998 |
| WO | WO 99/05268 | 2/1999 |
| WO | WO 99/24068 | 5/1999 |
| WO | WO 00/61164 | 10/2000 |
| WO | WO 00/63403 A | 10/2000 |
| WO | WO 01/05945 A3 | 1/2001 |
| WO | WO 01/38362 A2 | 5/2001 |
| WO | WO 0188117 A2 * | 11/2001 |
| WO | WO 02/018948 | 3/2002 |
| WO | WO 02/053580 | 7/2002 |
| WO | WO 03/003810 A1 | 5/2003 |
| WO | WO 03/048197 A1 | 6/2003 |
| WO | WO 03/048348 A2 | 6/2003 |
| WO | WO 03/051927 | 6/2003 |
| WO | WO 2004/003176 | 1/2004 |
| WO | WO 2004/099396 | 11/2004 |

OTHER PUBLICATIONS

Matsumoto et al., Characterization of a Human Glycoprotein (Erythropoietin) Produced in Culured Tobacco Cells, Plant Mol. Biol., 1995, vol. 27, pp. 1163-1172.*

Schiedner et al., Abstract, Efficient transformation of primary human amniocytes by E1 functions of Ad5: generation of new cell lines for adenoviral vector production, 2000, Hum. Gene Ther. 11, 2105-2116.

Pacitti et al., Inhibition of Reovirus Type 3 Binding to Host Cells by Sialylated Glycoproteins Is Mediated through the Viral Attachment Protein, Journal of Virology, May 1987, pp. 1407-1415, vol. 61, No. 5, American Society for Microbiology.

Zhang et al., Stable expression of human alpha-2,6-sialyltransferase in Chinese hamster ovary cells: functional consequences for human erythropoietin expression and bioactivity, BBA—General Subjects, 1998, pp. 441-452, vol. 1425, No. 3, Elsevier Science Publishers, NL.

Grabenhorst et al., Construction of stable BHK-21 cells coexpressing human secretory glycoproteins and human Gal(beta-1-4)GlcNAc-R alpha-2,6-sialyltransferase alpha-2,6-Linked NeuAc is preferentially attached to the Gal(beta-1-4)GlcNAc(beta-1-2)Man(alpha-1-3)-branch of diantennary oligosaccharides from secreted recombinant beta-trace protein, Eur. J. Biochem, 1995, pp. 718-725, vol. 232, No. 3, Berlin, Germany.

Hollister et al., Stable expression of mammalian beta1,4-galactosyltransferase extends the N-glycosylation pathway in insect cells, Glycobiology, 1998, pp. 473-480, vol. 8, No. 5, IRL Press, United Kingdom.

Jenkins et al., Getting the glycosylation right: Implications for the biotechnology industry, Nature Biotechnology, Aug. 1996, pp. 975-981, vol. 14, No. 8, Nature Publishing, US.

Weikert et al., Engineering Chinese hamster ovary cells to maximize sialic acid content of recombinant glycoproteins, Nature Biotechnology, Nov. 1999, pp. 1116-1121, vol. 17, No. 11, Nature Pub. Co., New York, NY, US.

Minch et al., Tissue Plasminogen Activator Coexpressed in Chinese Hamster Ovary Cells with alpha(2,6)-Sialytransferase Contains NeuAc-alpha(2,6)Gal-beta(1,4)Glc-N-AcR Linkages, Biotechnol. Prog., 1995, pp. 348-351, vol. 11, No. 3.

Pazur et al., Abstract, Oligosaccharides as immunodeterminants of erythropoietin for two sets of anti-carbohydrate antibodies, Journal of Protein Chemistry, Nov. 2000, pp. 631-635, vol. 19, No. 8.

Cronan, Abstract, Biotination of Proteins in-vivo a post-translational modification to label purify and study proteins, Journal of Biological Chemistry, Jun. 25, 1990, pp. 10327-10333, vol. 265, No. 18.

Stockwell et al., High-throughput screening of small molecules in Miniaturized Mammalian Cell-based Assays involving Post-translational Modifications, Chemistry and Biology, Feb. 1999, pp. 71-83, vol. 6, No. 2.

PCT International Search Report, PCT/NL02/00686, dated Mar. 7, 2003.

Pau et al., Abstract, The human cell line PER.C6 provides a new manufacturing system for the production of influenza vaccines, Vaccine, Mar. 21, 2001, pp. 2716-2721, vol. 19, No. 17-19.

Carroll et al., Abstract, Differential Infection of Receptor-modified Host Cells by Receptor-Specific Influenza Viruses, Virus Research, Sep. 1985, pp. 165-179, vol. 3, No. 2.

PCT International Search Report, PCT/NL02/00804, dated Sep. 26, 2003.

Varki et al., Essentials of glycobiology, 1999, Cold Spring Harbor Laboratory Press, Cold Spring Harbor, New York.

Ghosh-Choudhury et al., Protein 1X, a minor component of the human adenovirus capsid, is essential for the packaging of the full length genomes, The EMBO Journal, 1987, pp. 1733-1739, vol. 6, No. 6.

Louis et al., Cloning and Sequencing of the Cellular-Viral Junctions from the Human Adenovirus Type 5 Transformed 293 Cell Line, Virology, 1997, pp. 423-429, vol. 233.

NCBI Entrez Nucleotide accession No. U38242, Oct. 19, 1995.

NCBI Entrez Nucleotide accession No. NC_002018, Jun. 23, 2003.

NCBI Entrez Nucleotide accession No. X02996 J01967 J01968 J01970 J01971 J01972 J01974 J01976 J01977 J01978 J01979 K00515 V00025 V00026 V00027 V00029, Apr. 7, 1999.

Setoguchi et al., "Stimulation of Erythropoiesis by in vivo gene therapy: Physiologic consequences of transfer of the humanerythropoietin gene to experimental animals using an adenovirus vector," Blood, Nov. 1, 1994, pp. 2946-2953, vol. 84, No. 9.

European Search Report 05 10 0732, Apr. 7, 2005.

Fallaux et al, "New helper cells and matched early region 1-deleted adenovirus vectors prevent generation of replication-competent adenoviruses," Human Gene Therapy, Sep. 1, 1998, vol. 9, No. 1, pp. 1909-1917. Abstract.

Grand et al., "Modulation of the level of expression of cellular genes in adenovirus 12-infected and transformed human cells," Eur Mol Biol Organ J. 1986, 5 (6) 1253-1260. Abstract.

Grand et al., "The high levels of p53 present in adenovirus early region 1-transformed human cells do not cause up-regulation of MDM2 expression," Virology, 1995, vol. 210, No. 2, pp. 323-334. Abstract.

Yu et al., "Enhanced c-erbB-2/neu expression in human ovarian cancer cells correlates with more severe malignancy that can be suppressed by EIA," Cancer Res., 1993, 53 (4) 891-8. Abstract.

Bout et al., "Production of RCA-free batches of E1-deleted recombinant adenoviral vectors on PER.C6," Nucleic Acids Symp. Ser. 1998, XP-002115716, pp. 35-36.

Boutl et al., A novel packaging cell line (PER.C6) for efficient production of RCA-free batches of E1-deleted recombinant adenoviral vectors, Cancer Gene Therapy, 1997, pp. S32-S33, vol. 4, No. 6.

Bout et al., "Improved helper cells for RCA-free production of E1-deleted recombinant adenovirus vectors," Cancer Gene Therapy, 1996, pp. S24, vol. 3, No. 6.

Alkhatib et al., "Expression of Bicistronic Measles Virus P/C mRNA by Using Hybrid Adenovirus: Levels of C Protein Synthesized In Vivo Are Unaffected by the Presence or Absence of the Upstream P Initiator Codon," Journal of Virology, Nov. 1988, pp. 4059-4068, vol. 62, No. 11.

Alkhatib et al., "High-Level Eurcaryotic In Vivo Expression of Biologically Active Measles Virus Hemagglutinin by Using an Adenovirus Type 5 Helper-Free Vector System," Journal of Virology, Aug. 1988, pp. 2718-2727, vol. 62, No. 8.

Berg et al., High-Level Expression of Secreted Proteins from Cells Adapted to Serum-Free Suspension Culture, Research Report, BioTechniques, 1993, pp. 972-978, vol. 14, No. 6.

Brown et al., "Evaluation of Cell Line 293 for Virus isolation in Routine Viral Diagnosis," Journal of Clinical Microbiology, Apr. 1986, pp. 704-708, vol. 23, No. 4.

Bukreyev et al., "Recombinant Respiratory Syncytial Virus from Which the Entire SH Gene Has Been Deleted Grows Efficiently in Cell Culture and Exhibits Site-Specific Attenuation in the Respiratory Tract of the Mouse," Journal of Virology, Dec. 1997, pp. 8973-8982, vol. 71, No. 12.

Caravokyri et al., "Constitutive Episomal Expression of Polypeptide IX (pIX) in a 293-Based Cell Line Complements that Deficiency of pIX Mutant Adenovirus Type 5," Journal of Virology, Nov. 1995, pp. 6627-6633, vol. 69, No. 11.

Certificate of deposit of the PER.C6 cell line (ECACC deposit under No. 96022940), date not available.

Ciccarone et al., "Lipofectamine 2000 Reagent for Transfection of Eukaryotic Cells," Focus, 1999, pp. 54-55, vol. 21, No. 2.

Cote et al., Serum-Free Production of Recombinant Proteins and Adenoviral Vectors by 293SF-3F6 Cells, Biotechnology and Bioengineering, Sep. 5, 1998, pp. 567-575, vol. 59, No. 5.

DuBridge et al., "Analysis of Mutation in Human Cells by Using an Epstein-Barr Virus Shuttle System," Molecular and Cellular Biology, Jan. 1987, pp. 397-387, vol. 7, No. 1.

Endo et al., Growth of Influenza A Virus in Primary, Differentiated Epithelial Cells Derived from Adenoids, Journal of Virology, Mar. 1996, pp. 2055-2058, vol. 70, No. 3.

Fallaux et al., Characterization of 911: A New Helper Cell Line for the Titration and Propagation of Early Region 1-Deleted Adenoviral Vectors, Human Gene Therapy, Jan. 20, 1996, pp. 215-222, vol. 7. Figure 1 submitted by Opponent 1, 1996.

Gallimore et al., Transformation of Human Embryo Retinoblasts with Simian Virus 40, Adenovirus and ras Oncogenes, Anticancer Research, 1986, pp. 499-508, vol. 6.

Garnier et al., Scale-up of the adenovirus expression system for the production of recombinant protein in human 293S cells, Cytotechnology, 1994, pp. 145-155, vol. 15.

GenBank Accession No. X02996.1, 1993, "Adenovirus type 5 left 32% of the genome."

GIBCO cell culture, A Guide to Serum-Free Cell Culture, www.invitrogen.com, 2000.

Graham et al., "Characteristics of a Human Cell Line Transformed by DNA from Human Adenovirus Type 5," J. Gen. Virol., 1997, pp. 59-72, vol. 36.

Graham et al., "Growth of 293 cells in suspension culture," J Gen Virol, Mar. 1987, pp. 937-940, vol. 68.

Graham, Cell Lines, Promochem (visited Apr. 10, 2005) <http://www.lgcpromochem-atcc.com/SearchCatalogs/longview.cfm?view=ce.1146678...>.

Holzer et al., "Construction of a Vaccinia Virus Deficient in the Essential DNA Repair Enzyme Uracil DNA Glycosylase by a Complementing Cell Line," Journal of Virology, Jul. 1997, pp. 4997-5002, vol. 71, No. 7.

Inoue et al., Production of Recombinant Human Monoclonal Antibody Using ras-Amplified BHK-21 Cells in a Protein-free Medium, Biosci. Biotech. Biochem., 1996, pp. 811-817, vol. 60, No. 5.

Interlocutory Decision of the Opposition Division of Jul. 21, 2003 in the case EP 0 695 351(European application 94 913 174.2).

Lopez et al., Efficient production of biologically active human recombinant proteins in human lymphoblastoid cells form integrative and episomal expression vectors, Gene, 1994, pp. 285-291, vol. 148.

Lutz et al., "The Product of the Adenovirus Intermediate Gene IX is a Transcriptional Activator," Journal of Virology, Jul. 1997, pp. 5102-5109, vol. 71, No. 7.

Manservigi et al., "Protection from Herpes Simplex Virus Type 1 Lethal and Latent Infections by Secreted Recombinant Glycoprotein B Constitutively Expressed in Human Cells with a BK Virus Episomal Vector," Journal of Virology, Jan. 1990, pp. 431-436, vol. 64, No. 1.

Marketing Authorization and Scientific Discussion for Xigris, 2002.

Massie et al., Improved Adenovirus Vector Provides Herpes Simplex Virus Ribonucleotide Reductase R1 and R2 Subunits Very Efficiently, Biotechnology, Jun. 1995, pp. 602-608, vol. 13.

Merten et al., Production of Influenza Virus in Cell Cultures for Vaccine Preparation, Exp Med Biol., 1996, pp. 141-151, vol. 397.

Neumann et al., "Generation of influenza A viruses entirely from cloned cDNAs," Proc. Natl. Acad. Sci., Aug. 1999, pp. 9345-9350, vol. 96.

Notice of Opposition to a European Patent for 1 161 548 by Serono, 2005.

Opposition against European patent 1 108 878 B1 filed Oct. 5, 2005 in the name and on behalf of CEVEC Pharmaceuticals GmbH.

Opposition against European patent 1 161 548 B1 filed Nov. 16, 2005, in the name and on behalf of CEVEC Pharmaceutical GmbH.

Opposition against European patent 1108787 filed Oct. 5, 2005 in the name and on behalf of Probiogen AG.

Ory et al., "A stable human-derived packaging cell line for production of high titer retrovirus/vesicular stomatitis virus G pseudotypes," Proc. Natl. Acad. Sci., Oct. 1996, pp. 11400-11406, vol. 93.

Parkinson et al., "Stable Expression of a Secretable Deletion Mutant of Recombinant Human Thrombomodulin in Mammalian Cells," The Journal of Biological Chemistry, Jul. 25, 1990, pp. 12602-12610, vol. 265, No. 21.

Paul et al., Increased Viral Titer Through Concentration of Viral Harvests from Retroviral Packaging Lines, Human Gene Therapy, 1993, pp. 609-615, vol. 4.

Pleschka et al., "A Plasmid-Based Reverse Genetics System for Influenza A Virus," Journal of Virology, Jun. 1996, pp. 4188-4192, vol. 70, No. 6.

PubMed listing of abstracts (visited Apr. 10, 2005) <http://www.ncbi.nlm.nih.gov/entrez/query.fcgi?CMD=search&DB=pubmed.

Reina et al., Comparison of Madin-Darby Canine Kidney cells (MDCK) with a Green Monkey Continuous Cell Line (Vero) and Human Lung Embryonated Cells (MRC-5) in the Isolation of Influenza A Virus from Nasopharyngeal Aspirates by Shell Vial Culture, Journal of Clinical Microbiology, Jul. 1997, pp. 1900-1901, vol. 35, No. 7.

Rhim et al., "Development of Human Cell Lines from Multiple Organs," Annals of the New York Academy of Sciences, 2000, pp. 16-25, vol. 919.

Spector et al., "Regulation of Integrated Adenovirus Sequences During Adenovirus Infection of Transformed Cells," Journal of Virology, Dec. 1980, pp. 860-871, vol. 36, No. 3.

Stevens et al., "The N-Terminal Extension of the Influenza B Virus Nucleoprotein Is Not Required for Nuclear Accumulation or the Expression and Replication of a Model RNA," Journal of Virology, Jun. 1998, pp. 5307-5312, vol. 72, No. 6.

U.S. Department of Health and Human Services, Public Health Service, Food and drug Administration, Center for Biologics Evaluation and Research, International Association for Biologicals, National Institute of Allergy and Infectious Diseases, National Vaccine Program Office, World Health Organization, Evolving Scientific and Regulatory Perspectives on Cell Substrates for Vaccine Development, Workshop, Friday, Sep. 10, 1997 (visited Sep. 30, 2005) <http://www.fda.gov.cber.minutes/0910evolv.txt>.

Yan et al., Novel Asn-linked oligosaccharides terminating in GalNAcbeta(1-4)[Fucalpha(1-3)]GlcNAcbeta(1-.) are present in recombinant human Protein C expressed in human kidney 293 cells, Glycobiology, 1993, pp. 597-608, vol. 3, No. 6.

Yeager et al., Constructing immortalized human cell lines. Current Opinion Biotechnology, 1999, pp. 465-469, vol. 10.

Yeh et al., Adenoviral Vectors, pp. 25-42 of "Concepts in Gene Therapy," Publishers: Walter de Gruyter, New York, date not available.

Bout et al., "PER.C6 as production platform for human monoclonal antibodies," Human Antibodies, Oct. 8, 2003, pp. 30, vol. 12, No. 1-2.

Jones et al., "High-Level Expression of Recombinant IgG in the Human Cell Line PER.C6," Biotechnology Progress, Jan. 14, 2003, pp. 163-168, vol. 19.

Jones et al., "PER.C6 Cell Lines for Human Antibody Production: Crucell's Technology Maintains 'Human' Glycoylation Patterns," Genetic Engineering News, May 15, 2002, pp. 50, 54, vol. 80, No. 5.

Kurokawa et al., Biotech. Bioeng. 1994, vol. 44, pp. 95-103.

Pham et al., Abstract, "Large-Scale Transient Transfection of Serum-Free Suspension-Growing HEK293 EBNA1 Cells: Peptone Additives Improve Cell Growth and Transfection Efficiency," Biotechnology and Bioengineering, Nov. 5, 2003, pp. 332-342, vol. 84, No. 3.

Schultz-Cherry et al., J. Clin. Micro. 1998, pp. 3718-3720, vol. 36.

Trudel et al., Process Biochemistry Jan./Feb. 1983, pp. 2-4 and 9.

Xie et al., "Large-Scale Propagation of a Replication-Defective Adenovirus Vector in Stirred-Tank Bioreactor PER.C6 Cell Culture Under Sparging Conditions," Jul. 5, 2003, Biotechnology and Bioengineering, pp. 45-52, vol. 83, No. 1.

Xie et al., "Serum-Free Suspension Cultivation of PER.C6 Cells and Recombinant Adenovirus Production Under Different pH Conditions," Biotechnology and Bioengineering, Dec. 5, 2002, pp. 569-579, vol. 80, No. 5.

Yallop et al., "PER.C6® Cells for the Manufacture of Biopharmaceutical Proteins," Modern Biopharmaceuticals, ED. J. Knablein, 2005, Wiley-VCH Verlag GmbH & Co. KGaA, Weinheim, Germany.

* cited by examiner

A = Eprex
B = PER.C6-α2,6ST-EPO
C = PER.C6-EPO

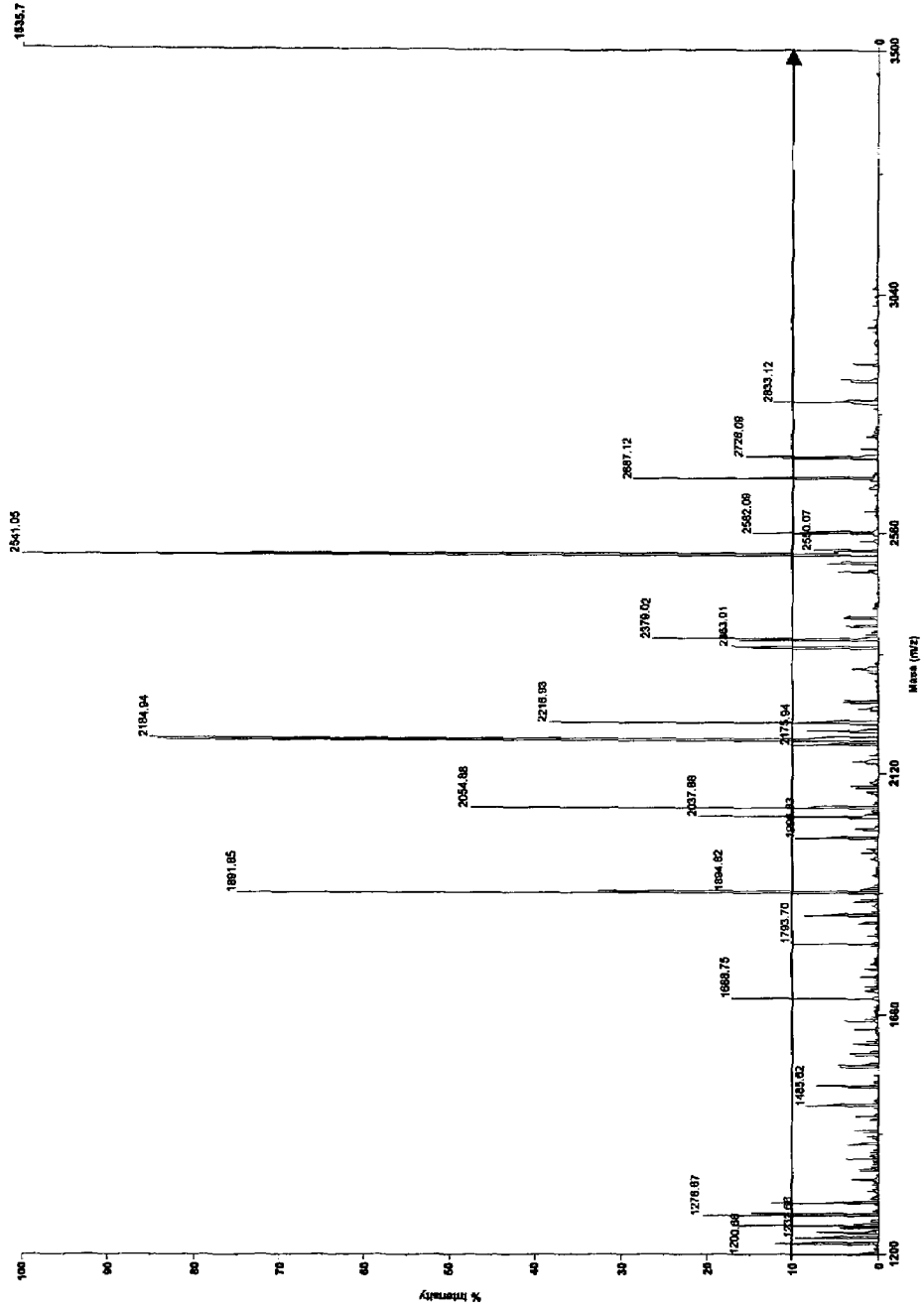

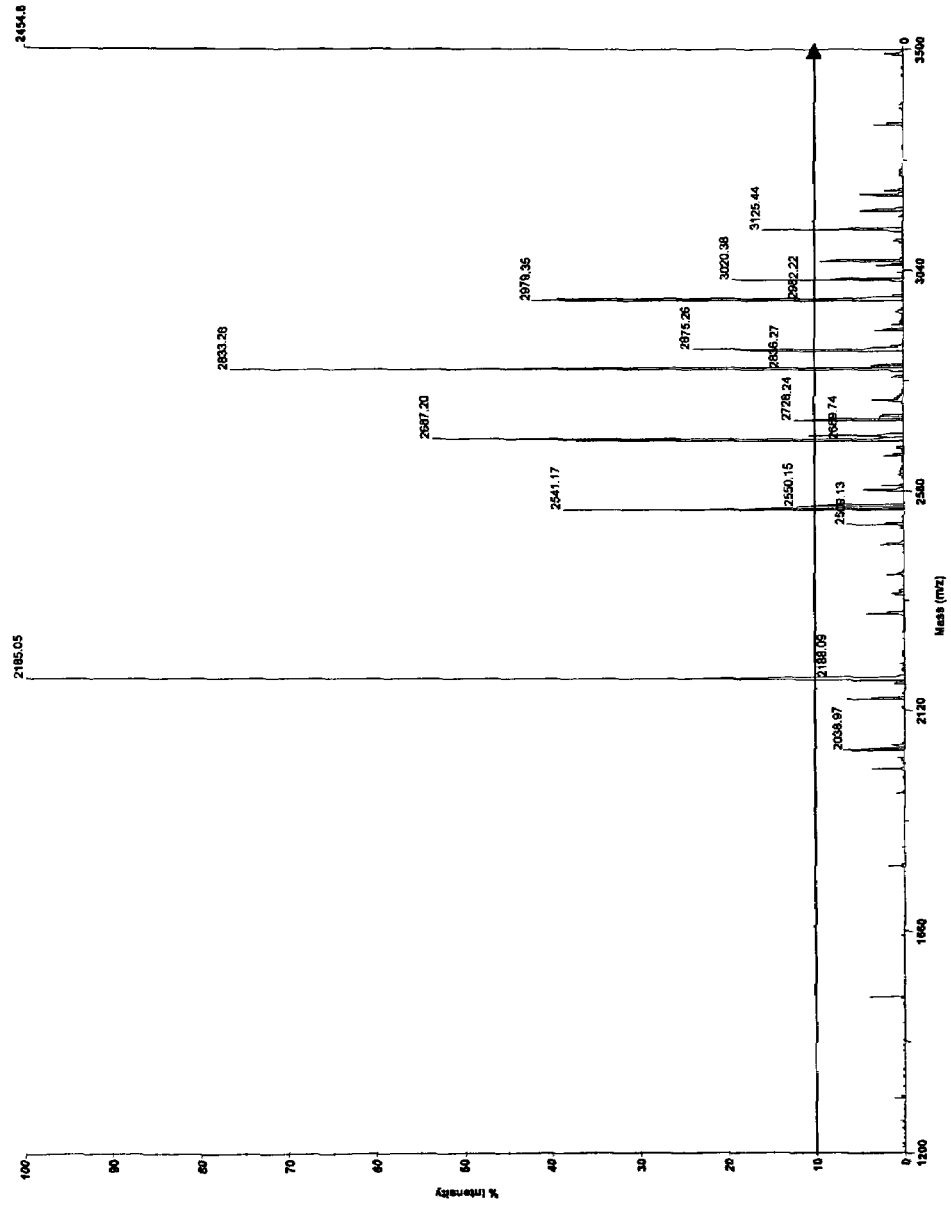

Fig. 12
PER.C6-EPO
A.
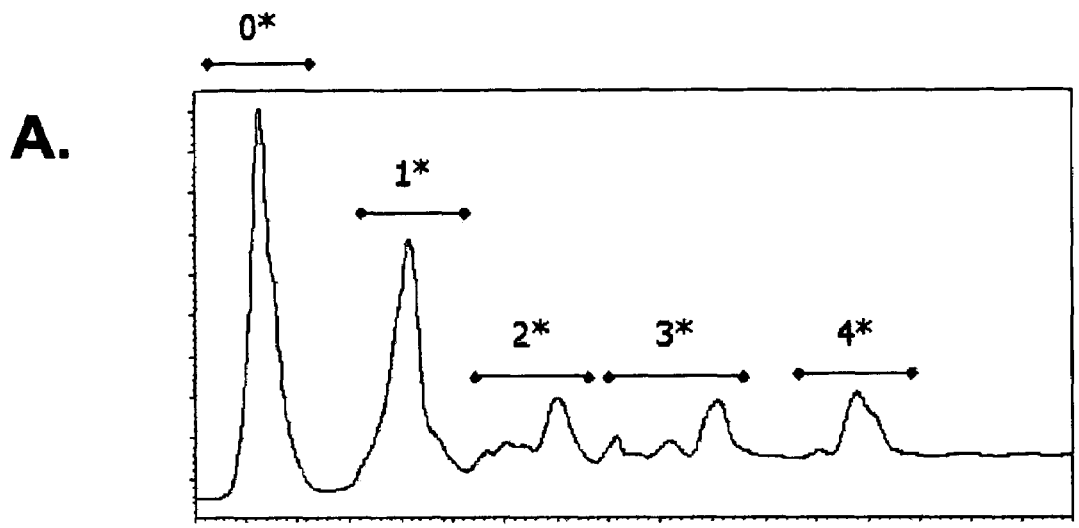
\* Number of sialic acids per glycan
PER.C6-ST-EPO
B.
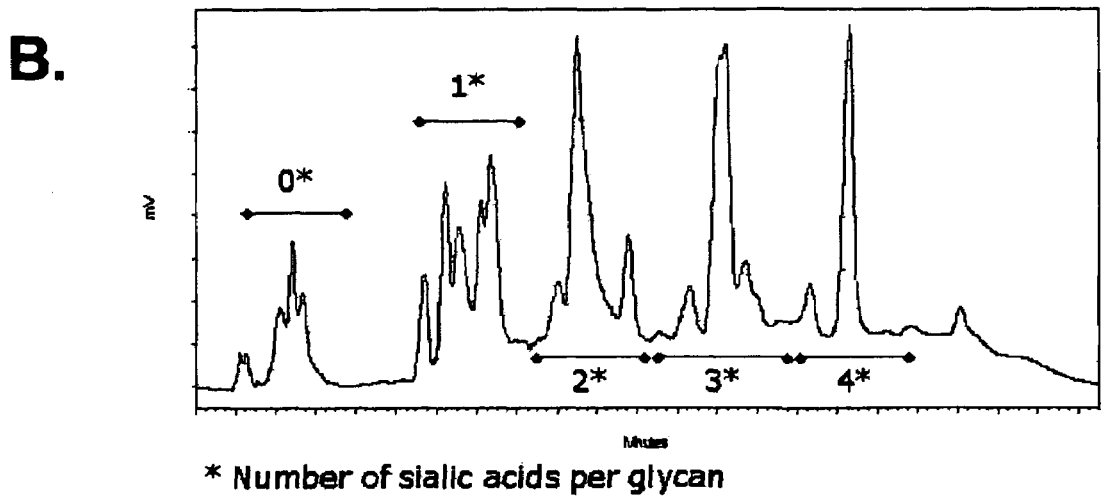
\* Number of sialic acids per glycan

Fig. 16
A.
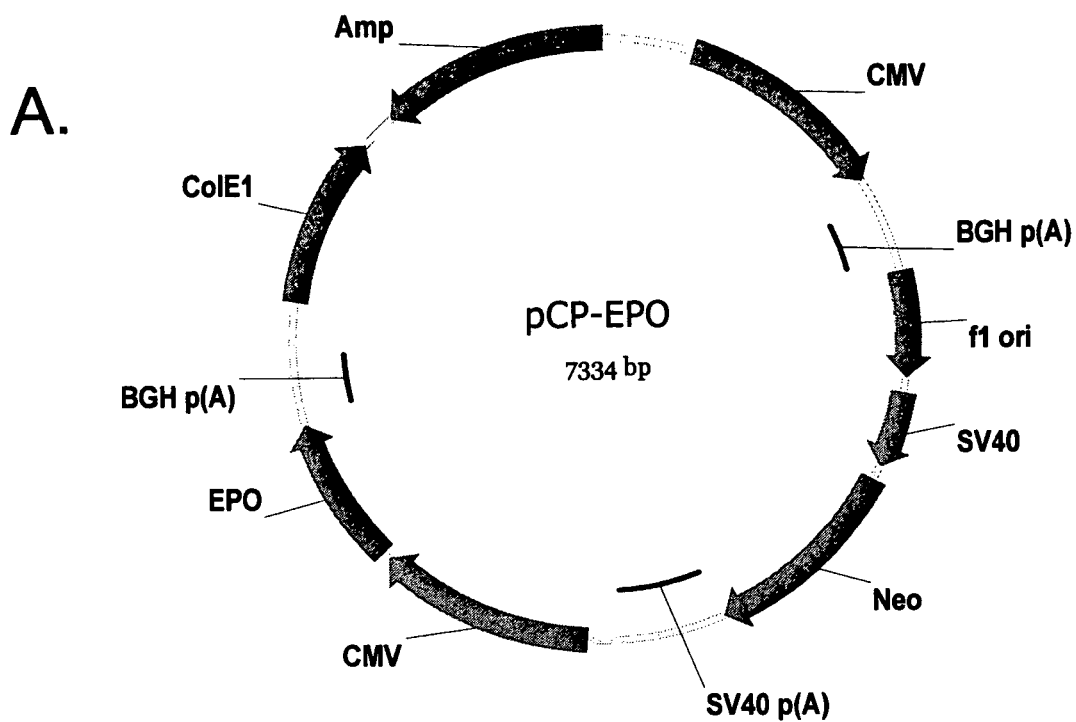
B.
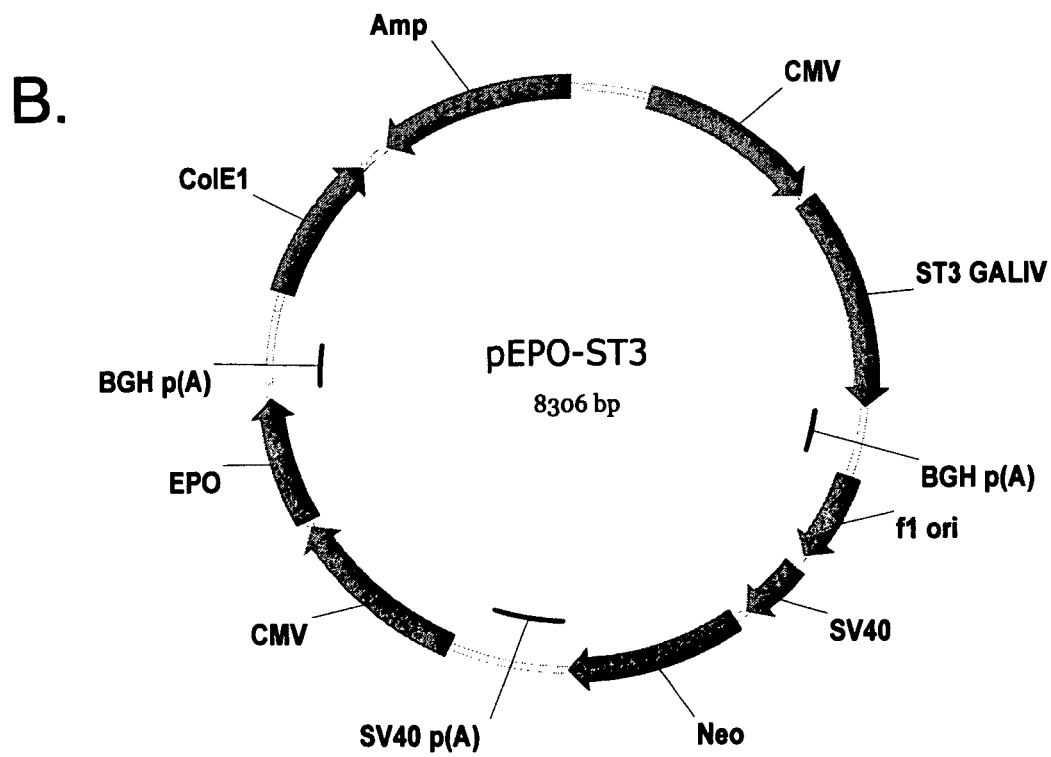

COMPOSITIONS OF ERYTHROPOIETIN ISOFORMS COMPRISING LEWIS-X STRUCTURES AND HIGH SIALIC ACID CONTENT

CROSS-REFERENCE TO RELATED APPLICATIONS

This application is a continuation-in-part of co-pending U.S. patent application Ser. No. 11/026,518, filed Dec. 30, 2004, which itself is a continuation-in-part of U.S. patent application Ser. No. 09/549,463, filed Apr. 14, 2000, now U.S. Pat. No. 6,855,544, the entire contents of all of which, including their respective sequence listings, are incorporated by this reference, which application claims priority under 35 U.S.C. Section 119(e) to Provisional Patent Application Ser. No. 60/129,452 filed Apr. 15, 1999, and which U.S. patent application Ser. No. 11/026,518 is further a continuation-in-part of co-pending U.S. patent application Ser. No. 10/497,832, filed Jan. 10, 2005, which is the national entry under 35 U.S.C. § 371 of PCT International Application Number PCT/NL02/00804, filed on Dec. 9, 2002, published in English as PCT International Patent Publication WO 03/048348 A2 on Jun. 12, 2003, the contents of all of which are incorporated by this reference. This application is further a continuation-in-part of co-pending U.S. patent application Ser. No. 10/494,140, filed Apr. 29, 2004, which published on Jul. 28, 2005 as Publication No. US2005/0164917, which is a national entry under 35 U.S.C. § 371 of PCT International Application Number PCT/NL02/00686, filed on Oct. 29, 2002, published in English as PCT International Patent Publication WO 03/038100 A1 on May 8, 2003, the entire contents of all of which are incorporated by this reference.

SEQUENCE LISTING

A sequence listing has been included herein to comply with the requirements of 37 C.F.R. §§ 1.821 through 1.825.

TECHNICAL FIELD

The invention relates generally to biotechnology and recombinant protein production, more particularly to the use of a human cell for the production of proteins. The invention is particularly useful for the production of proteins that benefit from post-translational or peri-translational modifications such as glycosylation and proper folding.

BACKGROUND

The expression of human recombinant proteins in heterologous cells has been well documented. Many production systems for recombinant proteins have become available, ranging from bacteria, yeasts, and fungi to insect cells, plant cells and mammalian cells. However, despite these developments, some production systems are still not optimal, or are only suited for production of specific classes of proteins. For instance, proteins that require post- or peri-translational modifications such as glycosylation, g-carboxylation, or g-hydroxylation cannot be produced in prokaryotic production systems. Another well-known problem with prokaryotic expression systems is the incorrect folding of the product to be produced, even leading to insoluble inclusion bodies in many cases.

Eukaryotic systems are an improvement in the production of, in particular, eukaryote derived proteins, but the available production systems still suffer from a number of drawbacks. The hypermannosylation in, for instance, yeast strains affects the ability of yeasts to properly express glycoproteins. Hypermannosylation often even leads to immune reactions when a therapeutic protein thus prepared is administered to a patient. Furthermore, yeast secretion signals are different from mammalian signals, leading to a more problematic transport of mammalian proteins, including human polypeptides, to the extracellular, which in turn results in problems with continuous production and/or isolation. Mammalian cells are widely used for the production of such proteins because of their ability to perform extensive post-translational modifications. The expression of recombinant proteins in mammalian cells has evolved dramatically over the past years, resulting in many cases in a routine technology.

In particular, Chinese hamster ovary cells ("CHO cells") have become a routine and convenient production system for the generation of biopharmaceutical proteins and proteins for diagnostic purposes. A number of characteristics make CHO cells very suitable as a host cell. The production levels that can be reached in CHO cells are extremely high. The cell line provides a safe production system, which is free of infectious or virus-like particles. CHO cells have been extensively characterized, although the history of the original cell line is vague. CHO cells can grow in suspension until reaching high densities in bioreactors, using serum-free culture media; a dhfr-mutant of CHO cells (DG-44 clone. Urlaub et al., 1983) has been developed to obtain an easy selection system by introducing an exogenous dhfr gene and thereafter a well-controlled amplification of the dhfr gene and the transgene using methotrexate.

However, glycoproteins or proteins comprising at least two (different) subunits continue to pose problems. The biological activity of glycosylated proteins can be profoundly influenced by the exact nature of the oligosaccharide component. The type of glycosylation can also have significant effects on immunogenicity, targeting and pharmacokinetics of the glycoprotein. In recent years, major advances have been made in the cellular factors that determine the glycosylation, and many glycosyl transferase enzymes have been cloned. This has resulted in research aimed at metabolic engineering of the glycosylation machinery (Fussenegger et al., 1999; Lee et al., 1989; Vonach et al., 1998; Jenikins et al., 1998; Zhang et al., 1998; Muchmore et al., 1989). Examples of such strategies are described herein.

CHO cells lack a functional α-2,6 sialyl-transferase enzyme, resulting in the exclusive addition of sialyc acids to galactose via α-2,3 linkages. It is known that the absence of α-2,6 linkages can enhance the clearance of a protein from the bloodstream. To address this problem, CHO cells have been engineered to resemble the human glycani profile by transfecting the appropriate glycosyl transferases. CHO cells are also incapable of producing Lewis-X oligosaccharides. CHO cell lines have been developed that express human N-acetyl-D-glucosaminyltransferase and α-1,3-fucosyltransferase III. In contrast, it is known that rodent cells, including CHO cells, produce CMP-N-acetylneuraminic acid hydrolase which lead to CMP-N-acetylneuraminic acids (Jenkins et al., 1996), an enzyme that is absent in humans. The proteins that carry this type of glycosylation can produce a strong immune response when injected (Kawashima et al., 1993). The recent identification of the rodent gene that encodes the hydrolase enzyme will most likely facilitate the development of CHO cells that lack this activity and will avoid this rodent-type modification.

Thus, it is possible to alter the glycosylation potential of mammalian host cells by expression of human glucosyl transferase enzymes. Yet, although the CHO-derived glycan structures on the recombinant proteins may mimic those present on their natural human counterparts, a potential problem exists in that they are still found to be far from identical. Another potential problem is that not all glycosylation enzymes have been cloned and are therefore available for metabolic engineering. The therapeutic administration of proteins that differ from their natural human counterparts may result in activation of the immune system of the patient and cause undesirable responses that may affect the efficacy of the treatment. Other problems using non-human cells may arise from incorrect folding of proteins that occurs during or after translation which might be dependent on the presence of the different available chaperone proteins. Aberrant folding may occur, leading to a decrease or absence of biological activity of the protein. Furthermore, the simultaneous expression of separate polypeptides that will together form proteins comprised of the different subunits, like monoclonal antibodies, in correct relative abundancies is of great importance. Human cells will be better capable of providing all necessary facilities for human proteins to be expressed and processed correctly.

It would thus be desirable to have methods for producing human recombinant proteins that involve a human cell that provides consistent human-type processing like post-translational and peri-translational modifications, such as glycosylation, which preferably is also suitable for large-scale production.

SUMMARY OF THE INVENTION

Described are, among other things, methods and compositions for producing recombinant proteins in a human cell line. The methods and compositions are particularly useful for generating stable expression of human recombinant proteins of interest that are modified post-translationally, for example, by glycosylation. Such proteins are believed to have advantageous properties in comparison with their counterparts produced in non-human systems such as Chinese hamster ovary cells.

The invention thus provides a method for producing at least one proteinaceous substance in a cell including a eukaryotic cell having a sequence encoding at least one adenoviral E1 protein or a functional homologue, fragment and/or derivative thereof in its genome, which cell does not encode a structural adenoviral protein from its genome or a sequence integrated therein, the method including providing the cell with a gene encoding a recombinant proteinaceous substance, culturing the cell in a suitable medium and harvesting at least one proteinaceous substance from the cell and/or the medium. A proteinaceous substance is a substance including at least two amino-acids linked by a peptide bond. The substance may further include one or more other molecules physically linked to the amino acid portion or not. Non-limiting examples of such other molecules include carbohydrate and/or lipid molecules.

A nucleic acid sequence encoding an adenovirus structural protein should not be present for a number of reasons. One reason is that the presence of an adenoviral structural protein in a preparation of produced protein is highly undesired in many applications of such produced protein. Removal of the structural protein from the product is best achieved by avoiding its occurrence in the preparation. Preferably, the eukaryotic cell is a mammalian cell. In a preferred embodiment, the proteinaceous substance harvested from the cell and the cell itself is derived from the same species. For instance, if the protein is intended to be administered to humans, it is preferred that both the cell and the proteinaceous substance harvested from the cell are of human origin. One advantage of a human cell is that most of the commercially most attractive proteins are human.

The proteinaceous substance harvested from the cell can be any proteinaceous substance produced by the cell. In one embodiment, at least one of the harvested proteinaceous substances is encoded by the gene. In another embodiment, a gene is provided to the cell to enhance and/or induce expression of one or more endogenously present genes in a cell, for instance, by providing the cell with a gene encoding a protein that is capable of enhancing expression of a proteinaceous substance in the cell.

As used herein, a "gene" is a nucleic acid sequence including a nucleic acid sequence of interest in an expressible format, such as an expression cassette. The nucleic acid sequence of interest may be expressed from the natural promoter or a derivative thereof or an entirely heterologous promoter. The nucleic acid sequence of interest can include introns or not. Similarly, it may be a cDNA or cDNA-like nucleic acid. The nucleic acid sequence of interest may encode a protein. Alternatively, the nucleic acid sequence of interest can encode an anti-sense RNA.

The invention further provides a method for producing at least one human recombinant protein in a cell, including providing a human cell having a sequence encoding at least an immortalizing E1 protein of an adenovirus or a functional derivative, homologue or fragment thereof in its genome, which cell does not produce structural adenoviral proteins, with a nucleic acid encoding the human recombinant protein. The method involves culturing the cell in a suitable medium and harvesting at least one human recombinant protein from the cell and/or the medium. Until the present invention, few, if any, human cells exist that have been found suitable to produce human recombinant proteins in any reproducible and upscaleable manner. We have now found that cells which include at least immortalizing adenoviral E1 sequences in their genome are capable of growing (they are immortalized by the presence of E1) relatively independent of exogenous growth factors. Furthermore, these cells are capable of producing recombinant proteins in significant amounts which are capable of correctly processing the recombinant protein being made. Of course, these cells will also be capable of producing non-human proteins. The human cell lines that have been used to produce recombinant proteins in any significant amount are often tumor (transformed) cell lines. The fact that most human cells that have been used for recombinant protein production are tumor-derived adds an extra risk to working with these particular cell lines and results in very stringent isolation procedures for the recombinant protein in order to avoid transforming activity or tumorigenic material in any protein or other preparations. According to the invention, it is therefore preferred to employ a method wherein the cell is derived from a primary cell. In order to be able to grow indefinitely, a primary cell needs to be immortalized in some kind, which, in the present invention, has been achieved by the introduction of adenovirus E1.

Also described are methods for producing and/or propagating virus particles such as influenza virus particles that preferably are present in a virus isolate obtained from an infected subject, the method comprising the steps of: contacting a cell with a virus particle and culturing the cell under conditions conducive to propagation of the virus particle, wherein the cell over-expresses a nucleic acid encoding an alpha2,6 or an alpha2,3 sialyltransferase. Also disclosed is a method for selective propagation of a set of virus particles such as influenza virus particles present in an influenza isolate, wherein the set of virus particles has affinity for receptors comprising a specific glycosylation residue, the method comprising the steps of: incubating a cell with the isolate; culturing the cell under conditions conducive to propagation of the virus particle; and harvesting virus particles so produced from the cell and/or the culture medium.

Also provided are novel vaccines and methods for making such vaccines, wherein the methods preferably comprise the steps of: treating the produced virus particles to yield antigenic parts; and harvesting at least one antigenic part such as hemagglutinin and/or neuraminidase from influenza virus. The invention further provides cells and cell lines and the use thereof, that over-express certain proteins involved in glycosylation for the production of vaccines, e.g., vaccines against influenza infection. Cells of the present invention are preferably human and transformed by adenovirus E1, such as PER.C6 cells or derivatives thereof.

BRIEF DESCRIPTION OF THE DRAWINGS

FIG. 10. MALDI-MS spectra of de-sialylated N-linked sugars of PER.C6-EPO produced in DMEM, in adherent cell culture (A) and produced in a suspension cell culture in serum-free medium (B).

FIG. 12. The number of sialic acids per N-linked sugar of EPO produced by PER.C6 cells that do not over-express $\alpha$-2,6-sialyltransferase (PER.C6-EPO, panel A), and of EPO produced by PER.C6 cells that do over-express $\alpha$-2,6-sialyltransferase (PER.C6-ST-EPO, panel B) was analyzed by HPLC ion-exchange as described in Example 47. The positions where sugars with 0, 1, 2, 3 or 4 sialic acids have been eluted are marked.

FIG. 16. Plasmid map of the pCP-EPO and pEPO-ST3 expression vectors. CMV=Cytomegalovirus promoter, BGHp(A)=Bovine Growth Hormone poly-adenylation sequence, fl ori=fl origin of replication, SV40=Simian Virus 40 promoter, Neo=Neomycin resistance marker, SV40 p(A)=Simian Virus 40 poly-adenylation sequence, EPO=erythropoietin, ColE1=ColE1 origin of replication, Amp=ampicillin resistance marker. See Example 51.

DETAILED DESCRIPTION

Figure 1:
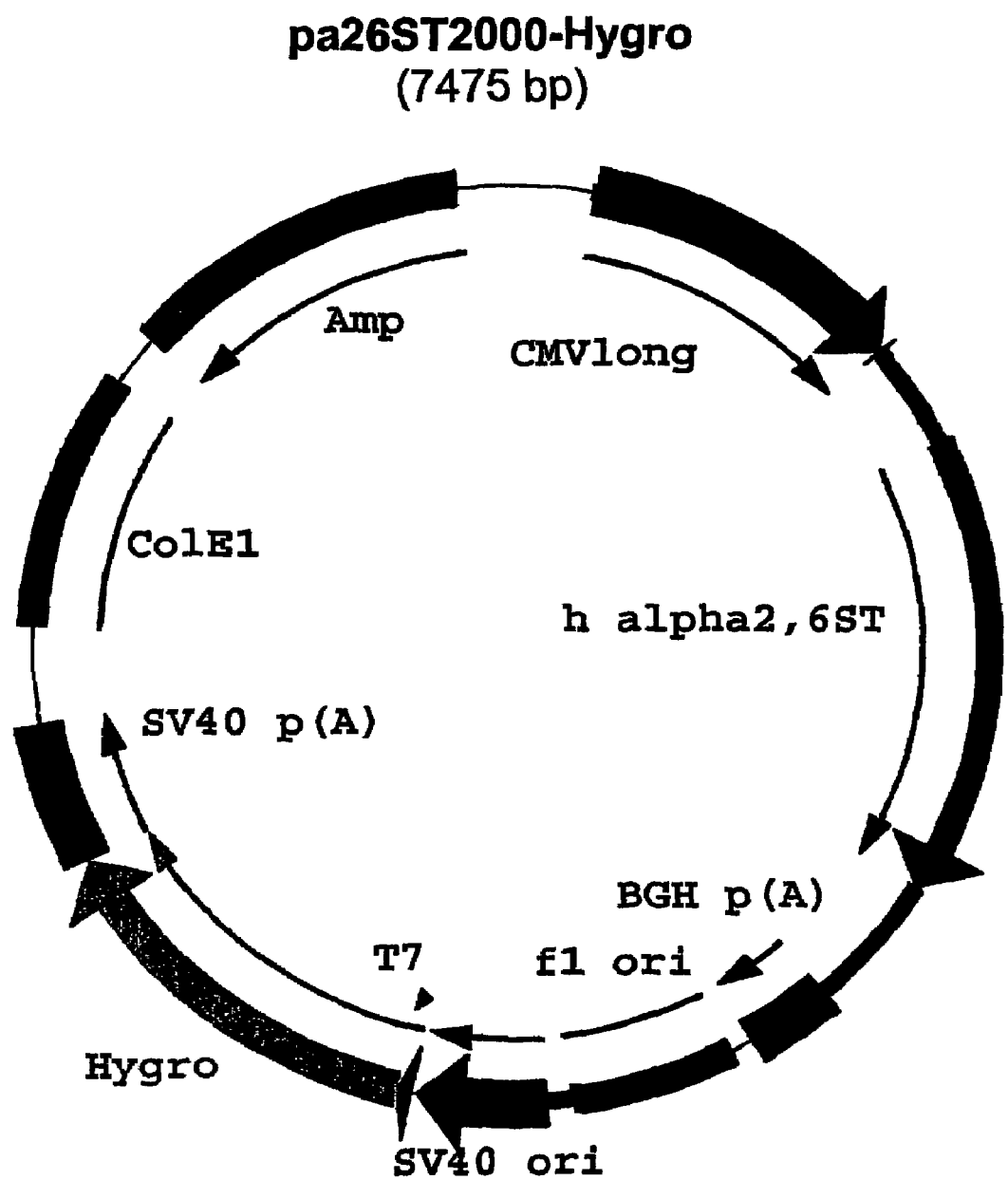
FIG. 1. Schematic representation of pAlpha2,6ST2000/Hygro.

The art is unclear on what the border is between transformed and immortalized. Here, the difference is represented in that immortalized cells grow indefinitely, while the phenotype is still present, and transformed cells also grow indefinitely but also display usually a dramatic change in phenotype.

In order to achieve large-scale (continuous) production of recombinant proteins through cell culture, it is preferred to have cells capable of growing without the necessity of anchorage. The cells of the present invention have that capability. The anchorage-independent growth capability is improved when the cells include a sequence encoding E2A or a functional derivative or analogue or fragment thereof in its genome, wherein preferably the E2A encoding sequence encodes a temperature sensitive mutant E2A, such as ts125. To have a clean, relatively safe production system from which it is easy to isolate the desired recombinant protein, it is preferred to have a method according to the invention, wherein the human cell includes no other adenoviral sequences. The most preferred cell for the methods and uses of the invention is PER.C6 as deposited under ECACC no. 96022940 or a derivative thereof (see, e.g., U.S. Pat. No. 5,994,128 to Fallaux et al. (Nov. 30, 1999), the contents of which are incorporated by this reference). PER.C6 cells behave better in handling than, for instance, transformed human 293 cells that have also been immortalized by the E1 region from adenovirus. PER.C6 cells have been characterized and have been documented very extensively because they behave significantly better in the process of upscaling, suspension growth and growth factor independence. Especially the fact that PER.C6 cells can be brought in suspension in a highly reproducible manner is something that makes it very suitable for large-scale production. Furthermore, the PER.C6 cell line has been characterized for bioreactor growth in which it grows to very high densities.

The cells according to the invention, in particular PER.C6 cells, have the additional advantage that they can be cultured in the absence of animal- or human-derived serum or animal- or human-derived serum components. Thus isolation is easier, while the safety is enhanced due to the absence of additional human or animal proteins in the culture, and the system is very reliable (synthetic media are the best in reproducibility). Furthermore, the presence of the Early region 1A ("E1A") of adenovirus adds another level of advantages as compared to (human) cell lines that lack this particular gene. E1A as a transcriptional activator is known to enhance transcription from the enhancer/promoter of the CMV Immediate Early genes (Olive et al., 1990, Gonnan et al., 1989). When the recombinant protein to be produced is under the control of the CMV enhancer/promoter, expression levels increase in the cells and not in cells that lack E1A.

In one aspect, the invention therefore further provides a method for enhancing production of a recombinant proteinaceous substance in a eukaryotic cell, including providing the eukaryotic cell with a nucleic acid encoding at least part of the proteinaceous substance, wherein the coding sequence is under control of a CMV-promoter, an E1A promoter or a functional homologue, derivative and/or fragment of either and further providing the cell with E1A activity or E1A-like activity. Like the CMV promoter, E1A promoters are more active in cells expressing one or more E1A products than in cells not expressing such products. It is known that indeed the E1A expression enhancement is a characteristic of several other promoters. For the present invention, such promoters are considered to be functional homologues of E1 A promoters. The E1A effect can be mediated through the attraction of transcription activators, the E1A promoter or homologue thereof, and/or through the removal/avoiding attachment of transcriptional repressors to the promoter. The binding of activators and repressors to a promoter occurs in a sequence-dependent fashion. A functional derivative-and or fragment of an E1A promoter or homologue thereof therefore at least includes the nucleic acid binding sequence of at least one E1 A protein regulated activator and/or repressor.

Another advantage of cells of the invention is that they harbor and express constitutively the adenovirus E1B gene. Adenovirus E1B is a well-known inhibitor of programmed cell death, or apoptosis. This inhibition occurs either through the 55K E1B product by its binding to the transcription factor p53 or subsequent inhibition (Yew and Berk 1992). The other product of the E1B region, 19K E1B, can prevent apoptosis by binding and thereby inhibiting the cellular death proteins Bax and Bak, both proteins that are under the control of p53 (White et al., 1992; Debbas and White, 1993; Han et al., 1996; and Farrow et al., 1995). These features can be extremely useful for the expression of recombinant proteins that, when over-expressed, might be involved in the induction of apoptosis through a p53-dependent pathway.

The invention further provides the use of a human cell for the production of a human recombinant protein, the cell having a sequence encoding at least an immortalizing E1 protein of an adenovirus or a functional derivative, homologue or fragment thereof in its genome, which cell does not produce structural adenoviral proteins. In another embodiment, the invention provides such a use wherein the human cell is derived from a primary cell, preferably wherein the human cell is a PER.C6 cell or a derivative thereof.

The invention further provides a use according to the invention, wherein the cell further includes a sequence encoding E2A or a functional derivative or analogue or fragment thereof in its genome, preferably wherein the E2A is temperature sensitive.

The invention also provides a human recombinant protein obtainable by a method according to the invention or by a use according to the invention, the human recombinant protein having a human glycosylation pattern different from the isolated natural human counterpart protein.

In another embodiment, the invention provides a human cell having a sequence encoding E1 of an adenovirus or a functional derivative, homologue or fragment thereof in its genome, which cell does not produce structural adenoviral proteins, and having a gene encoding a human recombinant protein, preferably a human cell which is derived from PER.C6 as deposited under ECACC no. 96022940.

In yet another embodiment, the invention provides such a human cell, PER.C6/E2A, which further includes a sequence encoding E2A or a functional derivative or analogue or fragment thereof in its genome, preferably wherein the E2A is temperature sensitive.

The proteins to be expressed in these cells using the methods of the invention are well known to persons skilled in the art. They are preferably human proteins that undergo some kind of processing in nature, such as secretion, chaperoned folding and/or transport, co-synthesis with other subunits, glycosylation, or phosphorylation. Typical examples for therapeutic or diagnostic use include monoclonal antibodies that are comprised of several subunits, tissue-specific plasminogen activator ("tPA"), granulocyte colony stimulating factor ("G-CSF") and human erythropoietin ("EPO" or "hEPO"). EPO is a typical product that, especially in vivo, heavily depends on its glycosylation pattern for its activity and immunogenicity. Thus far, relatively high levels of EPO have been reached by the use of CHO cells which are differently glycosylated in comparison to EPO purified from human urine, albeit equally active in the enhancement of erythrocyte production. The different glycosylation of such EPO, however, can lead to immunogenicity problems and altered half-life in a recipient.

The present invention also includes a novel human immortalized cell line for this purpose and the uses thereof for production. PER.C6 cells (PCT International Patent Publication WO 97/00326 or U.S. Pat. No. 5,994,128) were generated by transfection of primary human embryonic retina cells using a plasmid that contained the adenovirus serotype 5 (Ad5) E1A- and E1B-coding sequences (Ad5 nucleotides 459-3510) under the control of the human phosphoglycerate kinase ("PGK") promoter.

The following features make PER.C6 particularly useful as a host for recombinant protein production: 1. fully characterized human cell line; 2. developed in compliance with GLP; 3. can be grown as suspension cultures in defined serum-free medium devoid of any human- or animal-derived proteins; 4. growth compatible with roller bottles, shaker flasks, spinner flasks and bioreactors with doubling times of about 35 hrs; 5. presence of E1A causing an up-regulation of expression of genes that are under the control of the CMV enhancer/promoter; and 6. presence of E1B which prevents p53-dependent apoptosis possibly enhanced through overexpression of the recombinant transgene.

In one embodiment, the invention provides a method wherein the cell is capable of producing 2 to 200-fold more recombinant protein and/or proteinaceous substance than conventional mammalian cell lines. Preferably, the conventional mammalian cell lines are selected from the group consisting of CHO, COS, Vero, Hela, BHK and Sp-2 cell lines.

In one aspect of the invention, the proteinaceous substance or protein is a monoclonal antibody. Antibodies, or immunoglobulins ("Igs"), are serum proteins that play a central role in the humoral immune response, binding antigens and inactivating them or triggering the inflammatory response which results in their elimination. Antibodies are capable of highly specific interactions with a wide variety of ligands, including tumor-associated markers, viral coat proteins, and lymphocyte cell surface glycoproteins. They are, therefore, potentially very useful agents for the diagnosis and treatment of human diseases. Recombinant monoclonal and single chain antibody technology is opening new perspectives for the development of novel therapeutic and diagnostic agents. Mouse monoclonal antibodies have been used as therapeutic agents in a wide variety of clinical trials to treat infectious diseases and cancer. The first report of a patient being treated with a murine monoclonal antibody was published in 1980 (Nadler et al. 1980). However, the effects observed with these agents have, in general, been quite disappointing (for reviews, see Lowder et al. 1985, Mellstedt et al. 1991, Baldwin and Byers 1985). Traditionally, recombinant monoclonal antibodies (immunoglobulins) are produced on B-cell hybridomas. Such hybridomas are produced by fusing an immunoglobulin-producing B-cell, initially selected for its specificity, to a mouse myeloma cell and thereby immortalizing the B-cell. The original strategy of immortalizing mouse B-cells was developed in 1975 (Kohler and Milstein). However, immunoglobulins produced in such hybridomas have the disadvantage that they are of mouse origin, resulting in poor antibody specificity, low antibody affinity and a severe host antimouse antibody response (HAMA, Shawler et al. 1985). This HAMA response may lead to inflammation, fever, and even death of the patient.

Mouse antibodies have a low affinity in humans and, for reasons yet unknown, have an extremely short half-life in human circulation (19-42 hours) as compared to human antibodies (21 days, Frodin et al., 1990). That, together with the severity of the HAMA response, has prompted the development of alternative strategies for generating more human or completely humanized immunoglobulins (reviewed by Owens and Young 1994, Sandhu 1992, Vaswani et al. 1998).

One such strategy makes use of the constant regions of the human immunoglobulin to replace its murine counterparts, resulting in a new generation of "chimeric" and "humanized" antibodies. This approach is taken since the HAMA response is mainly due to the constant domains (Oi et al., 1983; Morrison et al., 1984). An example of such a chimeric antibody is CAMPATH-1H (Reichmann et al. 1988). The CAMPATH-1H Ab, used in the treatment of non-Hodgkin's B-cell lymphoma and refractory rheumatoid arthritis, is directed against the human antigen CAMPATH-1 (CDw52) present on all lymphoid cells and monocytes but not on other cell types (Hale et al. 1988, Isaacs et al. 1992). Other examples are Rituxan (Rituximab) directed against human CD20 (Reff et al. 1994) and 15C5, a chimeric antibody raised against human fragment-D dimer (Vandamme et al. 1990, Bulens et al. 1991) used in imaging of blood clotting. However, since these new generation chimeric antibodies are still partly murine, they can induce an immune response in humans, albeit not as severe as the HAMA response against fully murine antibodies of mouse origin.

In another, more sophisticated approach, ranges of residues present in the variable domains of the antibody, but apparently not essential for antigen recognition, are replaced by more human-like stretches of amino acids, resulting in a second generation or hyperchimeric antibodies (Vaswani et al. 1998). A well-known example of this approach is Herceptin (Carter et al. 1992), an antibody that is 95% human, which is directed against HER2 (a tumor-specific antigen) and used in breast tumor patients.

A more preferred manner to replace mouse recombinant immunoglobulins would be one resulting in the generation of human immunoglobulins. Importantly, since it is unethical to immunize humans with experimental biological materials, it is not feasible to subsequently select specific B-cells for immortalization as was shown for mouse B-cells (Kohler and Milstein 1975). Although B-cells from patients were selected for specific antibodies against cancer antigens, it is technically more difficult to prepare human immunoglobulins from human material as compared to mouse antibodies (Kohler and Milstein, 1975). A recombinant approach to produce fully human antibodies became feasible with the use of phage displayed antibody libraries, expressing variable domains of human origin (McCafferty et al. 1990, Clarkson et al. 1991, Barbas et al. 1991, Garrard et al. 1991, Winter et al. 1994, Burton and Barbas, 1994). These variable regions are selected for their specific affinity for certain antigens and are subsequently linked to the constant domains of human immunoglobulins, resulting in human recombinant immunoglobulins. An example of this latter approach is the single chain Fv antibody 17-1A (Riethmuller et al. 1994) that was converted into an intact human IgG1 kappa immunoglobulin named UBS-54, directed against the tumor-associated EpCAM molecule (Huls et al. 1999).

The production systems to generate recombinant immunoglobulins are diverse. The mouse immunoglobulins first used in clinical trials were produced in large quantities in their parental-specific B-cell and fused to a mouse myeloma cell for immortalization. A disadvantage of this system is that the immunoglobulins produced are entirely of mouse origin and render a dramatic immune response (HAMA response) in the human patient (as previously described herein).

Partially humanized or human antibodies lack a parental B-cell that can be immortalized and therefore have to be produced in other systems like CHO cells or Baby Hamster Kidney (BHK) cells. It is also possible to use cells that are normally suited for immunoglobulin production like tumor-derived human or mouse myeloma cells. However, antibody yields obtained in myeloma cells are, in general, relatively low (.+−.0.1 ug/ml) when compared to those obtained in the originally identified and immortalized B-cells that produce fully murine immunoglobulins (.+−.10 ug/ml, Sandhu 1992).

To circumvent these and other shortcomings, different systems are being developed to produce humanized or human immunoglobulins with higher yields.

For example, it was recently shown that transgenic mouse strains can be produced that have the mouse IgG genes replaced with their human counterparts (Bruggeman et al., 1991, Lonberg et al., 1994, Lonberg and Huszar, 1995, Jacobovits, 1995). Yeast artificial chromosomes ("YACs") containing large fragments of the human heavy and light (kappa) chain immunoglobulin (Ig) loci were introduced into Ig-inactivated mice, resulting in human antibody production which closely resembled that seen in humans, including gene rearrangement, assembly, and repertoire (Mendez et al. 1997, Green et al. 1994). Likewise, Fishwild et al. (1996) have constructed human Ig-transgenics in order to obtain human immunoglobulins using subsequent conventional hybridoma technology. The hybridoma cells secreted human immunoglobulins with properties similar to those of wild-type mice including stability, growth, and secretion levels. Recombinant antibodies produced from such transgenic mice strains carry no non-human amino acid sequences.

Nevertheless, human immunoglobulins produced thus far have the disadvantage of being produced in non-human cells, resulting in non-human post-translational modifications like glycosylatiorr and/or folding of the subunits. All antibodies are glycosylated at conserved positions in their constant regions, and the presence of carbohydrates can be critical for antigen clearance functions such as complement activation. The structure of the attached carbohydrate can also affect antibody activity. Antibody glycosylation can be influenced by the cell in which it is produced, the conformation of the antibody and cell culture conditions. For instance, antibodies produced in mouse cells carry glycans containing the Gal alpha1-3Gal residue, which is absent in proteins produced in human cells (Borrebaeck et al. 1993, Borrebaeck, 1999). A very high titer of anti-Gal alpha1-3Gal antibodies is present in humans (100 ug/ml, Galili, 1993), causing a rapid clearance of (murine) proteins carrying this residue in their glycans.

It soon became apparent that, in order to exert an effect, patients need to be treated with very high doses of recombinant immunoglobulins for prolonged periods of time. It seems likely that post-translational modifications on human or humanized immunoglobulins that are not produced on human cells strongly affect the clearance rate of these antibodies from the bloodstream.

It is unclear why immunoglobulins produced on CHO cells also need to be applied in very high dosages, since the Gal alpha1-3Gal residue is not present in glycans on proteins derived from this cell line (Rother and Squinto, 1996). Therefore, other post-translational modifications besides the Gal alpha1-3Gal residues are likely to be involved in specific immune responses in humans against fully human or humanized immunoglobulins produced on such CHO cells.

The art thus teaches that it is possible to produce humanized antibodies without murine-derived protein sequences. However, the current generation of recombinant immunoglobulins still differs from their natural human counterparts, for example, by post-translational modifications such as glycosylation and folding. These differences may result in activation of the immune system of the patient and cause undesirable responses that may affect the efficacy of the treatment. Thus, despite the development of chimeric antibodies, the current production systems still need optimization to produce fully human or humanized active antibodies.

It is thus clearly desirable to have methods for producing fully human antibodies which behave accordingly, and which are, in addition, produced at higher yields than observed in human myeloma cells.

Thus, it would be an improvement in the art to provide a human cell that produces consistent human-type protein processing like post-translational and peri-translational modifications, such as, but not limited to glycosylation. It would be further advantageous to provide a method for producing a recombinant mammalian cell and immunoglobulins from recombinant mammalian cells in large-scale production.

The present invention therefore further provides a method for producing at least one variable domain of an immunoglobulin in a recombinant mammalian cell, including providing a mammalian cell including a nucleic acid encoding at least an immortalizing E1 protein of an adenovirus or a functional derivative, homologue and/or fragment thereof in its genome, and further including a second nucleic acid encoding the immunoglobulin, culturing the cell in a suitable medium and harvesting at least one monoclonal antibody from the cell and/or the medium.

Previously, few, if any, human cells suitable for producing immunoglobulins in any reproducible and upscaleable manner have been found. The cells of the present invention include at least an immortalizing adenoviral E1 protein and are capable of growing relatively independent of exogenous growth factors.

Furthermore, these cells are capable of producing immunoglobulins in significant amounts and are capable of correctly processing the generated immunoglobulins.

The fact that cell types that have been used for immunoglobulin production are tumor-derived adds an extra risk to working with these particular cell lines and results in very stringent isolation procedures for the immunoglobulins in order to avoid transforming activity or tumorigenic material in any preparations. It is therefore preferred to employ a method according to the invention, wherein the cell is derived from a primary cell. In order to be able to grow indefinitely, a primary cell needs to be immortalized, which in the present invention has been achieved by the introduction of an adenoviral E1 protein.

In order to achieve large-scale (continuous) production of immunoglobulins through cell culture, it is preferred to have cells capable of growing without the necessity of anchorage. The cells of the present invention have that capability. The anchorage-independent growth capability is improved when the cells include an adenovirus-derived sequence encoding E2A (or a functional derivative or analogue or fragment thereof) in its genome. In a preferred embodiment, the E2A encoding sequence encodes a temperature sensitive mutant E2A, such as ts125. The cell may, in addition, include a nucleic acid (e.g., encoding tTa), which allows for regulated expression of a gene of interest when placed under the control of a promoter (e.g., a TetO promoter).

The nucleic acid may encode a heavy chain, a variable heavy chain, a light chain, and/or a variable light chain of an immunoglobulin. Alternatively, a separate or distinct nucleic acid may encode one or more variable domain(s) of an Ig (or a functional derivative, homologue and/or fragment thereof) as a counterpart to the first nucleic acid (described above). One or more nucleic acid(s) described herein may encode an ScFv and may be human or humanized. The nucleic acid(s) of the present invention are preferably placed under the control of an inducible promoter (or a functional derivative thereof).

To have a clean and safe production system from which it is easy to isolate the desired immunoglobulins, it is preferred to have a method according to the invention, wherein the human cell includes no other adenoviral sequences. The most preferred cell for the methods and uses of the invention is a PER.C6 cell (or a derivative thereof) as deposited under ECACC no. 96022940. PER.C6 cells have been found to be more stable, particularly in handling, than, for instance, transformed human 293 cells immortalized by the adenoviral E1 region. PER.C6 cells have been extensively characterized and documented, demonstrating good process of upscaling, suspension growth and growth factor independence. Furthermore, PER.C6 can be incorporated into a suspension in a highly reproducible manner, making it particularly suitable for large-scale production. In this regard, the PER.C6 cell line has been characterized for bioreactor growth, where it can grow to very high densities.

The cells of the present invention, in particular PER.C6, can advantageously be cultured in the absence of animal- or human-derived serum, or animal- or human-derived serum components. Thus, isolation of monoclonal antibodies is simplified and safety is enhanced due to the absence of additional human or animal proteins in the culture. The absence of serum further increases reliability of the system since use of synthetic media, as contemplated herein, enhances reproducibility.

The invention further provides the use of a recombinant mammalian cell for the production of at least one variable domain of an immunoglobulin, the cell having a sequence encoding at least an immortalizing E1 protein of an adenovirus or a functional derivative, homologue or fragment thereof in its genome, which cell does not produce structural adenoviral proteins. In another embodiment, the invention provides such a use wherein the cell is derived from a primary cell, preferably wherein the human cell is a PER.C6 cell or a derivative thereof.

The invention further provides a use according to the invention, wherein the cell further includes a sequence encoding E2A (or a functional derivative or analogue or fragment thereof) in its genome, preferably wherein the E2A is temperature sensitive. In addition, the invention provides a method of using the invention, wherein the cell further includes a trans-activating protein for the induction of the inducible promoter. The invention also provides immunoglobulins obtainable by a method according to the invention or by a use according to the invention.

In another embodiment, the invention provides a human cell having a sequence encoding E1 of an adenovirus (or a functional derivative, homologue or fragment thereof) in its genome, which cell does not produce structural adenoviral proteins, and having a gene encoding a human recombinant protein, preferably a human cell which is derived from PER.C6 as deposited under ECACC No. 96022940.

In yet another embodiment, the invention provides such a human cell, PER.C6/E2A, which further includes a sequence encoding E2A (or a functional derivative, analogue or fragment thereof) in its genome, preferably wherein the E2A is temperature sensitive.

Immunoglobulins to be expressed in the cells of the present invention are known to persons skilled in the art. Examples of recombinant immunoglobulins include, but are not limited to, Herceptin, Rituxan (RITUXIMAB), UBS-54, CAMPATH-1H and 15C5.

The present invention further provides methods for producing at least one variable domain of an immunoglobulin in a recombinant mammalian cell utilizing the immortalized recombinant mammalian cell of the invention, culturing the same in a suitable medium, and harvesting at least one variable domain of a selected Ig from the recombinant mammalian cell and/or medium. Immunoglobulins, variable domains of the immunoglobulins, or derivatives thereof may be used for the therapeutic treatment of mammals or the manufacture of pharmaceutical compositions.

In another aspect, the invention provides a method for producing a viral protein other than adenovirus or adenoviral protein for use as a vaccine including providing a cell with at least a sequence encoding at least one gene product of the E1 gene or a functional derivative thereof of an adenovirus, providing the cell with a nucleic acid encoding the viral protein, culturing the cell in a suitable medium allowing for expression of the viral protein and harvesting viral protein from the medium and/or the cell. Until the present invention, there are few, if any (human), cells that have been found suitable to produce viral proteins for use as vaccines in any reproducible and upscaleable manner and/or sufficiently high yields and/or easily purifiable. We have now found that cells which include adenoviral E1 sequences, preferably in their genome, are capable of producing the viral protein in significant amounts.

The preferred cell according to the invention is derived from a human primary cell, preferably a cell which is immortalized by a gene product of the E1 gene. In order to be able to grow, a primary cell, of course, needs to be immortalized. A good example of such a cell is one derived from a human embryonic retinoblast.

In cells according to the invention, it is important that the E1 gene sequences are not lost during the cell cycle. It is therefore preferred that the sequence encoding at least one gene product of the E1 gene is present in the genome of the (human) cell. For reasons of safety, care is best taken to avoid unnecessary adenoviral sequences in the cells according to the invention. It is thus another embodiment of the invention to provide cells that do not produce adenoviral structural proteins. However, in order to achieve large-scale (continuous) virus protein production through cell culture, it is preferred to have cells capable of growing without needing anchorage. The cells of the present invention have that capability. To have a clean and safe production system from which it is easy to recover and, if desirable, to purify the virus protein, it is preferred to have a method according to the invention, wherein the human cell includes no other adenoviral sequences. The most preferred cell for the methods and uses of the invention is PER.C6 as deposited under ECACC no. 96022940, or a derivative thereof.

Thus, the invention provides a method using a cell according to the invention, wherein the cell further includes a sequence encoding E2A or a functional derivative or analogue or fragment thereof, preferably a cell wherein the sequence encoding E2A or a functional derivative or analogue or fragment thereof is present in the genome of the human cell, and most preferably a cell wherein the E2A encoding sequence encodes a temperature sensitive mutant E2A.

Furthermore, as stated, the invention also provides a method according to the invention wherein the (human) cell is capable of growing in suspension.

The invention also includes a method wherein the human cell can be cultured in the absence of serum. The cells according to the invention, in particular PER.C6 cells, have the additional advantage that they can be cultured in the absence of serum or serum components. Thus, isolation is easy, safety is enhanced and reliability of the system is good (synthetic media are the best in reproducibility). The human cells of the invention, and in particular those based on primary cells and particularly the ones based on HER cells, are capable of normal post and peri-translational modifications and assembly. This means that they are very suitable for preparing viral proteins for use in vaccines.

Thus, the invention also includes a method wherein the viral protein includes a protein that undergoes post-translational and/or peri-translational modification, especially wherein the modifications include glycosylation. A good example of a viral vaccine that has been cumbersome to produce in any reliable manner is influenza vaccine. The invention provides a method according to the invention wherein the viral proteins include at least one of an influenza virus neuramidase and/or a hemagglutinin. Other viral proteins (subunits) that can be produced in the methods according to the invention include proteins from enterovirus, such as rhinovirus, aphtovirus, or poliomyelitis virus, herpes virus, such as herpes simplex virus, pseudorabies virus or bovine herpes virus, orthomyxovirus, such as influenza virus, a paramyxovirus, such as New Castle disease virus, respiratory syncitio virus, mumps virus or a measles virus, retrovirus, such as human immunodeficiency virus or a parvovirus or a papovavirus, rotavirus or a coronavirus, such as transmissible gastroenteritis virus or a flavivirus, such as tick-borne encephalitis virus or yellow fever virus, a togavirus, such as rubella virus or Eastern-, Western-, or Venezuelan equine encephalomyelitis virus, a hepatitis causing virus, such as hepatitis A or hepatitis B virus, a pestivirus, such as hog cholera virus or a rhabdovirus, such as rabies virus.

The invention also provides the use of a human cell having a sequence encoding at least one E1 protein of an adenovirus or a functional derivative, homologue or fragment thereof in its genome, which cell does not produce structural adenoviral proteins for the production of at least one viral protein for use in a vaccine. For such a use, the cells preferred in the methods according to the invention are also preferred. The invention also provides the products resulting from the methods and uses according to the invention, especially viral proteins obtainable according to those uses and/or methods, especially when brought in a pharmaceutical composition including suitable excipients and in some formats (subunits) adjuvants. Dosage and ways of administration can be sorted out through normal clinical testing if they are not yet available through the already registered vaccines.

Thus, the invention also provides a viral protein for use in a vaccine obtainable by a method or by a use according to the invention, the viral protein being free of any non-human mammalian proteinaceous material and a pharmaceutical formulation including such a viral protein.

In a preferred embodiment, the invention provides influenza vaccines obtainable by a method according to the invention or by a use according to the invention.

In another aspect, the invention provides the use of an adenoviral E1B protein or a functional derivative, homologue and/or fragment thereof having anti-apoptotic activity for enhancing the production of a proteinaceous substance in a eukaryotic cell, the use including providing the eukaryotic cell with the E1B protein, derivative, homologue and/or fragment thereof. In a preferred embodiment, the use includes a cell of the invention. In another preferred embodiment, the invention provides the use in a method and/or a use of the invention.

In another aspect, the invention provides methods for producing and/or propagating a virus particle, the method comprising the steps of: contacting a cell with a virus particle in a culture medium under conditions conducive to infection of the cell by the virus particle; and culturing the cell under conditions conducive to propagation of the virus particle, wherein the cell over-expresses a nucleic acid encoding an alpha2,6 sialyltransferase or a functional equivalent thereof. The nucleic acid may encode an alpha2,6 sialyltransferase from different sources, such as rat and human. Preferably the alpha2,6 sialyltransferase is human alpha2,6 sialyltransferase. The invention further provides methods for producing and/or propagating a virus particle, the method comprising the steps of: contacting a cell with a virus particle in a culture medium under conditions conducive to infection of the cell by the virus particle; and culturing the cell under conditions conducive to propagation of the virus particle, wherein the cell over-expresses a nucleic acid encoding an alpha2,3 sialyltransferase or a functional equivalent thereof. The nucleic acid may encode an alpha2,3 sialyltransferase from different sources, such as rat and human. Preferably the alpha2,3 sialyltransferase is human alpha2,3 sialyltransferase. In one embodiment of the invention, the virus particle is an influenza virus particle. Other non-limiting examples of virus particles that can be produced and/or propagated by using methods of the present invention are parainfluenza virus, adeno-associated virus ("AAV") or poliomavirus. Any virus that utilizes the glycosylation structures that are induced by the alpha2,3 and alpha2,6 sialyltransferases can be propagated and/or produced by using methods of the present invention.

In a preferred embodiment, the invention provides methods for propagating an influenza virus particle, wherein the influenza virus particle is present in an influenza isolate. More preferred are methods, wherein the influenza isolate is obtained from at least one influenza-infected mammalian subject. Even more preferred, are methods for propagating an influenza virus particle, wherein the influenza-infected mammalian subject is human or pig. In another embodiment, the invention provides methods for producing and/or propagating an influenza virus particle, wherein the influenza isolate is obtained from at least one influenza-infected bird. Isolates as used herein refers to batches of influenza viruses that are obtained from subjects that are infected with influenza viruses. These subjects may be all species that are susceptible for influenza viruses, such as humans, birds, pigs and horses. Humans can get infected with influenza in different ways: either directly from other humans or directly from animal subjects such as pigs and birds. Propagated viruses that are used for vaccine manufacturing might be originally derived from one or more subjects (one or more human individuals, or one or more birds, pigs, etc.) In the case where influenza virus transmission from a bird to a human causes direct disease in humans, as was the case in the Hong Kong in 1997 (see above) it might be useful to be able to produce and/or propagate the influenza virus particles present in the bird isolate directly for vaccine manufacturing. The present invention provides methods for producing and/or propagating influenza virus particles present in isolates that are obtained from species such as birds, pigs, horses and humans by over-expressing the sialyltransferase proteins that are involved in the glycosylation of cell surface proteins and that generate the so-called SAalpha2,3Gal and SAalpha2,6Gal linkages in the oligosaccharide chains. Isolates as used herein preferably refers to clinical isolates (i.e., isolates obtained from diseased patients). Such clinical isolates are also referred to as primary isolates. Primary isolates can be influenza isolates directly obtained from, for instance, the nose, mucus and/or feces of humans or animals that are infected with influenza virus(es). However, isolates that have been propagated on eggs on or cells or on other systems can still be further produced and/or propagated by methods of the present invention. Therefore, virus particles that are produced and/or propagated using the present invention may be present in passaged batches, but are preferably present in primary batches, such as clinical isolates.

In a preferred embodiment of the invention, the production and/or propagation of influenza virus particles is carried out by using cells in a culture medium, wherein the cell is transformed with E1 from adenovirus. More preferably, the cell is a human cell. In a highly preferred aspect, the invention provides methods for propagating an influenza virus particle according to the invention, wherein the human cell is PER.C6 or a derivative thereof.

PER.C6 cells are found to be useful for the propagation of different kinds of viruses such as rotavirus and influenza virus (see, PCT International Publication WO 01/38362). PER.C6 cells were first generated by transforming cells obtained from an embryonal retina with the E1 region of Adenovirus serotype 5. It was found that both alpha2,3 and alpha2,6 sialyltransferase proteins are present and active in PER.C6 cells (Pau et al. 2001). Therefore, virus particles that specifically interact with the sialic acid-galactose linkage of the 2,3 type as well as of the 2,6 type (SAalpha2,3Gal and SAalpha2,6Gal, respectively) were able to grow on PER.C6 cells. It is an important aspect of the invention that over-expression of either one of these sialyltransferase proteins leads to a specific propagation of sets of influenza viruses that either prefer the SAalpha2,3Gal residue or the SAalpha2,6Gal residue. This enables one to generate virus batches for vaccine production that have the best content for optimal protection. This content may differ. As discussed above, some spreading of the virus occurs mainly through human-human contact, while in others (such as the 1997 Hong Kong case, a direct bird-human contact was enough to sort a dramatic effect in humans. Depending on the virulence and the types of influenza viruses that play a role in this, a choice can be made for which set of virus particles in an isolate should be propagated with which the final vaccine is produced.

The present invention also provides methods for producing and/or propagating an influenza virus particle, wherein the nucleic acid encoding the sialyltransferase is heterologous to the cell. Preferably, the nucleic acid encoding the sialyltransferase is integrated into the genome of the cell. Heterologous as used herein means that the nucleic acid is manipulated such that the gene encoding the sialyltransferase expresses more of the protein than without the manipulation. Heterologous also means that the nucleic acid may be from a species that is different from the species from which the cell was derived, but may also be from the same species. A cell is said to over-express the sialyltransferase when the cell expresses more sialyltransferase than typical for that cell. A cell that over-expresses the sialyltransferase may also over-express the protein by manipulation of the genome of the cell such that the gene present in the genome of the cell expresses more of the protein than the cell did before it was manipulated. The over-expression may be induced by external means such as integration of a different or more-active promoter, by removal or inhibition of suppressors that normally limit the expression of the protein, or by chemical means. The over-expression may also be selected for. If cells are selected for a significant over-expression of at least one sialyltransferase they may be used for methods according to the present invention. Therefore, such cells and the use of such cells is also part of the present invention.

In another embodiment, the present invention provides methods for making a vaccine, the method comprising the steps of: producing and/or propagating a virus particle according to methods of the invention; and inactivating the virus particles so produced. Preferably the methods for making a vaccine further comprise the steps of: treating the virus particles so produced to yield antigenic parts; and obtaining at least one of the antigenic parts, preferably through means of purification and/or enrichment for the at least one part. Preferably a purified and/or enriched composition comprising the at least one obtained antigenic part does not comprise other antigenic parts of the treated virus particles. In a more preferred embodiment, the invention provides methods for making a vaccine, wherein the antigenic part comprises the hemagglutinin protein or a part thereof, and/or the neuraminidase protein or a part thereof from influenza virus. The neuraminidase ("NA") and the hemagglutinin ("HA") proteins are the most prominent antigenic parts of the influenza virus particle and are prone to differences during different propagation steps. The invention also provides vaccines obtainable according to methods of the present invention, while it also provides pharmaceutical compositions comprising a vaccine obtainable according to the present invention.

As mentioned, the cells of the present invention are extremely useful for the propagation of primary, clinical isolates comprising influenza virus particles, while the cells can also be applied for propagating isolates that already have been passaged on embryonated eggs or on other systems, to obtain a selection of influenza virus particles that recognize specific glycosylation residues present on glycoproteins. Thus, the present invention also provides the use of a cell line over-expressing an alpha2,6 sialyltransferase or a functional part thereof for the propagation of a virus particle and the use of a cell line over-expressing an alpha2,3 sialyltransferase or a functional part thereof for the propagation of a virus particle. Preferably, the virus particle is an influenza virus particle. More preferably, the influenza virus particle is present in an influenza isolate obtained from at least one influenza-infected mammalian subject. Even more preferred, are uses of the cell line according to the present invention, wherein the influenza-infected mammalian subject is a human or a pig, whereas it is also preferred that the influenza virus particle is present in an influenza isolate obtained from at least one influenza-infected bird.

Further provided is a method for selective production and/or propagation of a set of predetermined virus particles present in an isolate, wherein the set of predetermined virus particles has a preference for a specific glycosylation moiety present on a receptor, and wherein the isolate comprises in addition to the set also virus particles not having the preference, the method comprising the steps of: incubating a cell which is capable of expressing and exposing the receptor comprising the specific glycosylation moiety, with the isolate in a culture medium under conditions conducive to infection of the cell by at least one virus particle present in the set; culturing the cell under conditions conducive to propagation of the virus particle; and harvesting virus particles so produced from the cell and/or the culture medium.

A glycosylation moiety as used herein refers to any kind of residue, linkage and/or group of sugar types present in an oligosaccharide chain on a glycoprotein that is recognized by a virus particle for infection. Preferably, the glycosylation moiety comprises a SAalpha2,6Gal residue or a SAalpha2,3Gal residue. More preferred are methods wherein the set of predetermined virus particles is a set of predetermined influenza virus particles. The SAalpha2,6Gal residue and SAalpha2,3Gal residues are specifically recognized by the HA protein of the virus particle, in the case of influenza. It depends on the HA protein whether there is any specificity in the interaction with either one residue. In general, influenza isolates comprise viruses that interact specifically with the SAalpha2,6Gal residue as well as viruses that specifically interact with the SAalpha2,3Gal residue. With the present invention it is now possible to selectively propagate either set of viruses from clinical, primary and/or passaged isolates to obtain propagated sets of viruses that are useful in the production of an influenza vaccine, useful in humans. Besides the fact that vaccines can be produced for humans, it is also possible by using methods and means of the present invention to selectively propagate viruses for the manufacturing of veterinary applications to, for instance, prevent the spreading of influenza viruses through swine or horse populations. Preferably, the influenza isolate is obtained from at least one influenza-infected human, pig or bird. It is also preferred that the cell is a human cell and that it is transformed with E1 from adenovirus. Highly preferred are cells that are PER.C6 cells or derivatives thereof. "Derivatives" with respect to PER.C6 cells, as used herein, refer to modified versions of the original PER.C6 cells, wherein, for instance, other heterologous nucleic acids are introduced, knocked out, or in other ways modified. Non-limiting examples of PER.C6 derivatives are PER.C6 cells that stable express a temperature-sensitive mutant of Adenovirus E2A, or that express other adenovirus nucleic acids such as E4. If certain nucleic acids in PER.C6 cells have been switched on or off by other means such as chemical treatment or knockout techniques, these cells still remain PER.C6 derivatives.

In another preferred embodiment, the invention provides methods for selective propagation of a set of virus particles present in an isolate, wherein the cell comprises a nucleic acid encoding a sialyltransferase that is heterologous to the cell. Even more preferred are methods according to the present invention, wherein the nucleic acid encoding a sialyltransferase is integrated into the genome of the cell. Such an integrated nucleic acid is preferably stably integrated through the use of selection markers such as the hygromycin and neomycin resistance genes.

The present invention also provides human cells comprising a heterologous nucleic acid encoding an alpha2,6 sialyltransferase or an alpha2,3 sialyltransferase. Preferably, the nucleic acid is integrated into the genome of the human cell. The invention also provides the use of such cells for the selective propagation of virus particles, preferably being influenza virus particles.

The present invention provides optimization of a process for propagation of primary isolates of human influenza virus. Also, the present invention provides optimization of a process for propagating primary as well as laboratory isolates of influenza viruses using the SAalpha2,6Gal or SAalpha2,3Gal (or both) glycosylation moieties present on cell surface glycoproteins. In general, human influenza viruses recognize the SAalpha2,6Gal moiety, while the avian influenza viruses recognize the SAalpha2,3Gal moiety. The swine influenza viruses generally utilize both residues. The invention provides optimization of a process for propagation of any virus for which the replication depends on the activity of alpha2,3 sialyltransferase and/or alpha2,6 sialyltransferase, or more generally, on the presence of SAalpha2,3Gal or SAalpha2,6Gal residues. The methods of the present invention comprise the use of cells in a culture medium. As an example of such a process, human cells were taken that are known to support efficient replication and production of influenza viruses.

The cells of the present invention are not only useful for the propagation of influenza viruses. It is well known in the art that other viruses such as Adeno-Associated Virus (AAV), human poliomavirus and parainfluenza viruses utilize the alpha2,3 and alpha2,6 linkages in glycoproteins for infection (Liu et al. 1998; Suzuki et al. 2001; Walters et al. 2001). Therefore the present invention also provides methods for (selective) production and/or propagation of other viruses that use these glycosylation structures for recognition and infection of the targeted cell. Furthermore, the invention provides the use of the cells of the invention and the methods and means for the production of viruses other than influenza and for the production of vaccines against such viruses, if applicable. The invention, therefore, also provides vaccines against viruses that utilize the SAalpha2,3Gal and the SAalpha2,6Gal residues for cellular recognition and infectivity.

It has been previously demonstrated that PER.C6™ cells (ECACC deposit 96022940) represent an ideal substrate for the propagation of influenza virus and that the production levels from PER.C6 resulted in high-titer preparations suitable for vaccine purposes (WO 01/38362). A novel cell line provided by the present invention, named "PER.C6-alpha2,6ST" is derived from PER.C6 through the following process: a plasmid harboring a nucleic acid encoding human alpha2,6 sialyltransferase under the control of the strong CMV promoter was transfected into PER.C6 cells and cells were subsequently selected for stable integration of the plasmid. The PER.C6-alpha2,6ST cells are characterized by the higher expression of SAalpha2,6Gal-containing receptors as compared to the number of receptors carrying the SAalpha2,6Gal residue in the original PER.C6 cells. This does not directly imply that the proteins carrying such moieties are over-expressed, but that the percentage of proteins carrying the SAalpha2,6Gal residue is higher than the percentage of such proteins in PER.C6 cells. PER.C6 cells are without over-expression of the alpha2,6 sialyltransferase already capable of expressing both SAalpha2,3Gal and SAalpha2,6Gal residues on cell surface glycoproteins. It is, however, an important aspect of the present invention to increase the percentage of proteins carrying the SAalpha2,6Gal residue in comparison to the percentage of proteins that carry the SAalpha2,3Gal residue. Due to direct substrate competition in the intracellular glycosylation machinery, receptors of the SAalpha2,3Gal type become under represented on the cell surface of cells over-expressing the alpha2,6 sialyltransferase protein. These combined characteristics make this new cell line an ideal medium for propagating primary influenza virus isolates without inducing selection pressure in the wild-type population. The propagation of such isolates on the cells of the present invention results in efficient production of large virus stocks with unaltered HA specificity and immunogenicity that are highly useful for the production of vaccines. As virus produced in PER.C6-alpha2,6ST does not present mutations resulting from adaptation to the SAalpha2,3Gal receptor (as is the case for embryonated eggs), the immunogenic properties of this virus are most comparable with those of naturally circulating influenza viruses. Consequently, vaccine preparations obtained from influenza virus grown on PER.C6-alpha2,6ST are ideally suited to induce a protective response against circulating wild-type influenza virus. It is known in the art that human influenza viruses are of the type recognizing the SAalpha2,6Gal linkages and it is, therefore, recognized in the art that it is desired to obtain vaccines comprising proteins from these viruses in order to sort a more protective immune response in humans (Newman et al. 1993).

If human influenza viruses are propagated via embryonated chicken eggs, virus variants that are able to bind specifically to SAalpha2,3Gal will be selected for, and the SAalpha2,6Gal recognizing viruses will be selected out. PER.C6 cells have both SAalpha2,6Gal and SAalpha2,3Gal containing receptors at its surface. For a preferred propagation of the SAalpha2,6Gal recognizing viruses it is, therefore, preferred to have over-expression of receptors that harbor this component, as discussed above. To determine the effect of the opposite, namely over-expression of human alpha2,3 sialyltransferase, the present invention also provides methods and means for generating another novel cell line named "PER.C6-alpha2,3ST." These cells are derived from PER.C6 in a similar manner as described above for the PER.C6-alpha2,6ST cells, by transfection of a plasmid harboring nucleic acid encoding human alpha2,3 sialyltransferase under the control of the strong CMV promoter, after which, cells carrying a stable integration of the plasmid are selected. A PER.C6-alpha2,3ST cell is characterized by the higher expression of SAalpha2,3Gal-containing receptors.

Both alpha2,6 sialyltransferase and alpha2,3 sialyltransferase over-expressing cell lines are useful since alpha2,6 sialyltransferase over-expressing cells can be used for the propagation of influenza viruses that preferably recognize the SAalpha2,6Gal residue, while the alpha2,3 sialyltransferase over-expressing cells can be used for the propagation of influenza viruses that preferably recognize the SAalpha2,3Gal residue. When the infection and the spreading of the viruses mainly occurs via human-human contact and the viruses become more adapted to the infectious route via the SAalpha2,6Gal residues, then it is preferred to apply the alpha2,6 sialyltransferase over-expressing cell line. On the other hand, when the infectivity occurs directly from birds that do not have glycoproteins harboring the SAalpha2,3Gal residue to humans (as was the case in the small but severe epidemic in Hong Kong in 1997) then it is preferred to apply cells that over-express the alpha2,3 sialyltransferase.

As used herein, the terms alpha2,6 sialyltransferase or alpha2,3 sialyltransferase refer to the respective transferases and also to equivalents of the transferase, wherein the equivalents comprise the same transferase activity in kind, not necessarily in amount, as the transferase it is equivalent to. Suitable equivalents can be generated by the person skilled in the art. A part of the transferase is a suitable equivalent if it comprises the same transferase activity in kind not necessarily in amount. Other suitable equivalents are derivatives and/or analogues of alpha2,3 sialyltransferase or alpha2,3 sialyltransferase comprising the same transferase activity in kind, not necessarily in amount, as the transferase it is equivalent to. Such derivatives may be generated through conservative amino acid substitution or otherwise. A derivative can also be made from a part of the respective transferases.

An influenza virus particle, as used herein, can be an influenza virus or an influenza virus-like particle. An equivalent of an influenza virus particle is a virus (like) particle comprising the same infectivity properties in kind, not necessarily in amount, as an influenza virus particle. Such equivalents can, for instance, be generated by recombinant means. Such equivalents may comprise molecules not typically present in an influenza virus.

As shown in U.S. Pat. No. 6,855,544 (the '544 patent) of Hateboer et al., the contents of the entirety of which are incorporated by this reference, immortalized human embryonic retina cells expressing at least an adenovirus E1A protein can be suitably used for the production of recombinant proteins. Recombinant proteins having N-linked glycosylation produced in such cells have a specific glycosylation profile for instance characterized by the presence of Lewis-X structures (described in the incorporated United States Patent Application Publication No. US2005/0164917). Lewis X structures (see FIG. 19) have never been reported to occur in human urinary EPO or in recombinant human EPO produced in CHO and BHK cells. N-acetyl-galactosamine is not found in the N-linked sugars of human urinary EPO and recombinant human EPO produced by CHO cells. Only trace amounts of N-acetyl-galactosamine have been reported to occur in the N-linked sugars in a few batches of recombinant human EPO produced in BHK cells.

Another characteristic of the proteins produced thus far in E1A expressing cells appeared a relatively low galactosylation and low sialylation of the N-linked glycans (WO 03/038100). For certain purposes, this may be an advantage, but for other purposes, higher levels of galactosylation and preferably also sialylation may be beneficial.

For instance, erythropoietin (EPO) that is produced in cells expressing E1A, has a pronounced number of Lewis-X structures and a relatively low percentage of galactosylation and sialylation in the N-linked glycans (WO 03/038100), resulting in molecules that are very suitable for treatment of ischemia/reperfusion injuries, but are less suitable for the treatment of anemia. For the treatment of anemia, it has been established that a high degree of sialylation of EPO is beneficial to increase the half-life of the EPO in serum of treated subjects, and thereby the time when the substance is active in increasing the red blood cell count (Goldwasser et al., 1974). Hence, for the treatment of ischemia/reperfusion injuries, the expression of EPO in E1A-expressing cells has besides the high level of expression the further advantage of preferred glycosylation pattern of the produced EPO for this use. However, for other uses of EPO, different glycosylation patterns may be beneficial.

For other proteins similar situations may exist, i.e., for certain uses the specific glycosylation pattern observed upon expression in E1A-expressing cells may be highly beneficial, while for other purposes a different glycosylation profile may be more suitable.

For the purpose of broadening the potential use spectrum of recombinant proteins produced in E1A-expressing cells, it would therefore be beneficial to increase the galactosylation and sialylation of such proteins. The present invention provides methods to accomplish this.

It has now been found that the glycosylation of recombinant proteins expressed in E1A-expressing cells, such as immortalized human embryonic retina cells, can be altered to increase galactosylation and optionally sialylation, by metabolic and genetic engineering. This finding is put to practice in the present invention, by providing novel processes for the production of recombinant proteins in E1A-expressing cells, resulting in desired novel glycoforms of the produced proteins. The novel glycoforms of these proteins can be used for additional purposes when compared to the same proteins produced in such cells by the hitherto known processes.

The present invention therefore provides a process for producing a protein of interest in an immortalized human embryonic retina cell, said cell expressing at least an adenoviral E1A protein and expressing said protein of interest from a nucleic acid sequence encoding said protein of interest, said nucleic acid sequence being under control of a heterologous promoter, said cell further expressing at least one glycosyltransferase from a nucleic acid sequence encoding said glycosyltransferase under control of a heterologous promoter, said protein of interest comprising at least one N-linked glycan, said process comprising: culturing said cell in suspension in a serum-free culture medium and allowing expression of the recombinant protein in said cell. The glycosyltransferase is preferably a mammalian glycosyltransferase, more preferably a human glycosyltransferase. In preferred embodiments, the glycosyltransferase is a sialyltransferase, preferably chosen from the group consisting of alpha-2,6-sialyltransferases and alpha 2,3-sialyltransferases.

Cells expressing E1A of an adenovirus that can be used according to this aspect of the invention include cells of human origin, and are preferably immortalized. In preferred embodiments these cells also express E1B of an adenovirus. Examples are A549 cells comprising E1 (see, e.g., WO 98/39411), 293 cells (Graham et al., 1977), amniocytes expressing E1 (Schiedner et al., 2000; see U.S. Pat. No. 6,558,948 for immortalization of primary amniocytes with adenovirus E1 sequences), and preferably are human embryonic retina (HER) cells, most preferably PER.C6 cells (U.S. Pat. No. 5,994,128).

N-linked glycans are sugar chains that are covalently linked to asparagine residues of a polypeptide (Varki et al. 1999). The process of N-glycosylation starts with the attachment of a dolichol oligosaccharide precursor to the asparagines precursor. This precursor is subsequently modified into a high-mannose, hybrid, or complex-type oligosaccharide. In complex type N-linked sugars, both the α3- and α6-linked mannose residues are substituted by N-acetylglucosamine (GlcNAc) residues. Complex type N-glycans may contain two to five GlcNAc-bearing branches that are referred to as antennae. The ultimate structure of complex type N-linked sugars may vary extensively and depends on the protein to which they are attached, on the host cell and on the conditions under which the host cell is cultured. The GlcNAc-bearing branches may be modified with galactose (Gal) or N-acetyl-gatactosamine (GalNAc) forming so-called LacNAc or LacdiNAc structures. Also, GlcNAc-bearing branches may contain multiple LacNAc structures forming so-called polylactomine structures. Terminal galactoses may be modified with an α2,3- or an α2,6-linked sialic acid whereas terminal N-acetyl-galactosomines may only be modified with an α2,6-linked sialic acid.

The addition of sialic acids to terminal Gal or GalNAc is mediated by sialyltransferases. Probably more than 20 different sialyltransferases are encoded by the human genome (Harduin-Lepers et al., 2001). They differ in substrate specificity, tissue distribution and various biochemical parameters. No human sialyltransferase has today been described that can link a sialic acid to a LacNac or LacdiNAc structure, which is modified with an α1,3-linked fucose. Such fucose is linked to the GlcNAc residue thereby forming a so-called Lewis x structure. Sialylated Lewis x (sialyl-Lewis x) structures, nevertheless, may exist; yet, these are formed through a process in which the sialic acid is attached to the sugar before the GlcNAc is modified with the α1,3-linked fucose.

The formation of sialyl-Lewis x structures depends, in turn, on the type of fucosyltransferase. Some fucosyltransferases use only non-sialylated LacNac or LacdiNAc structures as a substrate, others only use sialylated LacNAc as a substrate, and a third group of α1,3 fucosyltransferases may use both as a substrate.

Recombinant proteins, such as recombinant human erythropoietin (EPO), produced in PER.C6 cells may be poorly sialylated due to a low incorporation of Gal and due to the presence of α1,3-linked fucoses. The present invention provides a method to increase the sialic acid content of proteins produced in PER.C6 cells. The increased level of sialylation is obtained in two steps: the first step involves the increase in the level galactosylation in order to provide more (acceptor) sites for sialylation. An increase in the level of galactosylation was found to occur when PER.C6 cells were adapted for growth in suspension in a serum-free culture medium. The second step involves the increase the cell's potential to catalyze the process of sialylation, which was accomplished by the over-expression of a sialyltransferase. Because the N-linked sugars of recombinant proteins expressed in PER.C6 cells may contain LacdiNAc structures, which may only be modified with an α2,6-linked sialic acid, an α2,6-sialyltransferase was used to increase the level of sialylation.

Thus, two aspects appear relevant for increasing sialylation of produced proteins in immortalized HER cells that express adenovirus E1A protein: improvement of the galactosylation to increase the number of substrates for sialylation, and increasing the sialylation of the available Gal and GalNAc substrates. The invention has improved the hitherto described protein production process in E1A-expressing immortalized HER cells by overexpressing a glycosylation enzyme—preferably a sialyltransferase—in these cells (genetic engineering), and by culturing such cells in suspension in serum-free medium (metabolic engineering). By combining these measures, the forming of mature N-linked sugars that are sialylated can be dramatically improved over the hitherto described production processes in the absence of overexpression of a glycosyltransferase and performed in cells that have been cultured in a serum-containing medium in an adherent fashion. Each of the two measures, i.e., overexpression of an enzyme involved in post-translational modification of proteins on the one hand, and the growth of the cells in serum-free culture medium in suspension culture, contributes to the improved final result, and hence the invention also comprises embodiments where only one of the two measures is taken at a time. When proteins with N-linked sugars having a high degree of galactosylation and terminal sialylation are desired, it is best to combine these measures according to the invention. It will be clear that these measures can be used to increase the sialylation of the N-linked sugars of any protein comprising N-linked sugars produced in the cells of the invention. In one embodiment, erythropoietin (EPO) or a fragment thereof, a mutein thereof or a derivative thereof is the protein of interest that is produced according to the method of the invention. EPO produced according to this process has higher sialic acid content than EPO produced thus far in cells that express E1A of an adenovirus, and hence more resembles the commercially available EPO preparations. Commercial EPO preparations are usually recombinantly produced in CHO or BHK cells, and fractions containing a high degree of sialylation are isolated, because increased sialylation is beneficial for the half-life of the protein and therefore for the capability to exert its therapeutic effect of increasing hemoglobin and red blood cell counts. Hence, the new cells and process according to the invention provide the possibility to use immortalized HER cells that express E1A for the recombinant production of EPO with increased half-life. In addition, the method benefits from the high level of production that is possible in the cells according to the invention.

Of course, also the EPO or other proteins produced in the E1A containing HER cells that overexpress a sialyltransferase, can be fractionated to obtain further fractions with still higher sialic acid contents, as is also done for commercial preparations of EPO. In one aspect, the EPO produced according to the invention, is purified using an anion exchange column to obtain highly sialylated fractions.

Methods to produce proteins in host cells are well established and known to the person skilled in the art. The use of immortalized HER cells for this purpose is described in the incorporated '544 patent.

In general, the production of a recombinant protein in a host cell comprises the introduction of nucleic acid in expressible format into the host cell, culturing the cells under conditions conducive to expression of the nucleic acid and allowing expression of the said nucleic acid in said cells.

Alternatively, a protein that is naturally expressed in desired host cells, but not at sufficient levels, may be expressed at increased levels by introducing suitable regulation sequences such as a strong promoter in operable association with the desired gene (e.g., see, e.g., WO 99/05268, where the endogenous EPO gene is overexpressed by introduction of a strong promoter upstream of the gene in human cells).

The protein may be expressed intracellularly, but preferably is secreted into the culture medium. Naturally secreted proteins, such as many proteins of interest for pharmaceutical applications, contain secretion signals that bring about secretion of the produced proteins. If desired, secretion signals may also be added to certain proteins, by methods known in the art.

Nucleic acid encoding a protein in expressible format may be in the form of an expression cassette, and usually requires sequences capable of bringing about expression of the nucleic acid, such as enhancer(s), promoter, polyadenylation signal, and the like. Several promoters can be used for expression of recombinant nucleic acid, and these may comprise viral, mammalian, synthetic promoters, and the like. In certain embodiments, a promoter driving the expression of the nucleic acid of interest is the CMV immediate early promoter, for instance comprising nt. −735 to +95 from the CMV immediate early gene enhancer/promoter, as this promoter has been shown to give high expression levels in cells expressing E1A of an adenovirus (e.g., see, e.g., WO 03/051927). The nucleic acid of interest may be a genomic DNA, a cDNA, synthetic DNA, a combination of these, etc.

Cell culture media are available from various vendors, and serum-free culture media are nowadays often used for cell culture, because they are more defined than media containing serum. The cells of the present invention grow well in serum-containing media as well as in serum-free media. Usually a short period is required to adapt PER.C6 cells from a serum containing medium, such as DMEM+9% FBS, to a serum-free medium. One example of a serum-free culture medium that is very suitable for use in the present invention is EX-CELL™ VPRO medium (JRH Biosciences, catalog number 14561). The cells of the invention in general grow adherently in serum-containing media, but are very proficient in growing in suspension to high cell densities (10×106 cells/ml and higher) in serum-free culture media, which means that they do not need a surface to adhere to, but remain relatively free from each other and from the walls of the culture vessel during most of the time. Processes for culturing the cells of the invention to high densities and/or for obtaining very high product yields from these cells have been described (WO 2004/099396), incorporated herein by reference.

The concept of genetic engineering to alter glycosylation of recombinant proteins produced in a cell has been amply established, and is for instance discussed in detail in U.S. Pat. No. 5,047,335, incorporated herein by reference. The general concept of genetically altering glycosylation is discussed therein, and entails introducing into a host cell at least one gene which is capable of expressing at least one enzyme which is selected from the group consisting of glycosyltransferases, fucosyltransferases, galactosyltransferases, beta-acetylgalactosaminyltransferases, N-acetylglycosaminyltransferases and sulfotransferases (collectively referred to herein as 'glycosylation enzymes'), and expressing a sufficient amount of at least one of said enzymes in said cell to thereby alter the glycosylation of a protein produced by said cell. In examples in that document, glycosylation of CHO cells is altered by recombinant expression of a transfected rat alpha-2,6-sialyltransferase gene, resulting in the presence of NeuAc-alpha-2,6Gal sequences on the cell surface carbohydrates, whereas in the absence of the transfected gene, only NeuAc-alpha-2,3Gal sequences are produced in these cells. Subsequent work has established that glycosylation engineering is applicable to the production of recombinant proteins in host cells (e.g., Grabenhorst et al., 1995; Jenkins et al., 1998; Weikert et al., 1999; Fukuta et al., 2000; Prati et al., 2000). Hence, the methods for genetic engineering of glycosylation are well established and known to the person skilled in the art, and can as such be beneficially used in preferred embodiments according to the present invention.

To this purpose, nucleic acid encoding the desired glycosylation enzyme in expressible format is or has been introduced into the cells according to the invention, and the desired glycosylation enzyme is expressed during the culturing of the cells according to the invention when the protein of interest is expressed. This results in an altered glycosylation pattern of the protein of interest as compared to the situation when no recombinant glycosylation enzyme is expressed in the cells. In preferred embodiments, the glycosylation enzyme is a sialyltransferase, more preferred an alpha-2,3-sialyltransferase and/or an alpha-2,6-sialyltransferase. Preferably, the encoded glycosylation enzyme is a mammalian enzyme, more preferably a human enzyme. The nucleic acid encoding the desired glycosylation enzyme preferably is under control of a heterologous promoter, which should be active or have the possibility of being regulated in the cells of the invention. Preferably, the nucleic acid encoding the glycosylation enzyme is integrated into the genome of the cells, to ensure stable inheritance, and provide for stable expression of the enzyme in subsequent generations of the cells. The introduction of a glycosylation enzyme into immortalized HER cells expressing E1A is described herein. As can be seen from the examples, the expression of the sialyltransferase increases the sialylation of recombinant proteins in those cells. Moreover, when the E1A-expressing cells expressing the sialyltransferase are grown in suspension in serum-free culture media according to the present invention, a clear and significant increase in sialylation of the N-linked glycans of a recombinant protein that is expressed in these cells is observed, as can be seen in example 45 below. Hence, in preferred embodiments of the processes according to the present invention, the cells according to the invention comprise nucleic acid encoding a glycosylation enzyme, preferably a sialyltransferase, more preferably alpha-2,6-sialyltransferase, in expressible format, for instance under control of a heterologous promoter, i.e., a promoter that is not the natural promoter of the gene encoding the glycosylation enzyme.

In another preferred embodiment, the cells comprise nucleic acid encoding an alpha-2,3-sialyltransferase, in expressible format, for instance under control of a heterologous promoter. The alpha-2,3-sialyltransferase may be the human α-2,3-sialyltransferase, known as SIAT4C or STZ (GenBank accession number L23767, see also U.S. Pat. No. 5,494,790).

As described herein and in WO 03/038100, EPO molecules comprising Lewis-X structures can be suitably produced in cells that express adenovirus E1A sequences, such as PER.C6 cells. A Lewis-X structure, as present on an N-linked glycan of a glycoprotein such as EPO, is a structure that comprises an α1,3-linked fucose attached to N-acetylglucosamine in a lactosamine-type antenna structure. There are two types of Lewis-X structures: one with a terminal galactose and one with a terminal N-acetylgalactosamine (GalNAc) residue. These terminal groups may or may not be linked to a sialic acid; when linked to a sialic acid, the Lewis-X structure is a sialyl-Lewis-X structure. Hence, sialyl-Lewis-X structures are a subgroup of Lewis-X structures for the purpose of the present invention. One advantage of having a protein comprising N-linked glycans with Lewis-X structures, described in WO 03/038100, is that such structures may aid the protein in binding to certain selectins and provide anti-inflammatory properties. As discussed hereinabove however, it would also be beneficial if such proteins would comprise increased terminal sialylation, to increase the serum half-life and hence effectiveness of the protein for certain therapeutic applications.

As an example, erythropoietin (EPO) produced in PER.C6 cells as described in WO 03/038100 comprises Lewis-X structures, but only a low level of sialic acid (see Example 50, Table 4). The methods described in the present invention provide the possibility to obtain protein molecules comprising Lewis-X structures, and increased numbers of sialic acid moieties attached to their sugar structures.

The invention therefore provides a composition comprising one or more isoforms of an erythropoietin (EPO) comprising glycans linked thereto, wherein said glycans comprise on average: a) at least 1 Lewis-X structure per EPO molecule, and b) at least 6 sialic acid moieties per EPO molecule. A mixture of such isoforms can be obtained by producing EPO in PER.C6 cells that further overexpress a sialyltransferase, and which is cultured in suspension in serum-free medium. Previously disclosed methods (see, the incorporated WO 03/038100) for producing EPO in PER.C6 cells lead to EPO that comprised Lewis-X structures but significantly lower amounts of sialic acids (see entry 1 in Table 4). The composition is generally obtained as a mixture of EPO isoforms, but the person skilled in the art could isolate the separate isoforms, as described in U.S. Pat. No. 5,856,298, in particular Example 1 therein. In more preferred embodiments, the composition comprises on average at least 7 sialic acid moieties per EPO molecule, more preferably at least 8 sialic acid moieties per EPO molecule. The sialic acid moieties are mainly present as terminal sialic acids on N-linked glycans, but some sialic acids might be present on O-linked glycans and contribute to the average sialic acid content of the composition. In certain embodiments, the EPO molecule of the invention comprises 3 N-linked glycans. In certain embodiments, the EPO molecule of the invention comprises 3 N-linked glycans and one O-linked glycan. The Lewis-X structures are present on N-linked glycans of the EPO molecules. It is shown herein that upon expression in PER.C6 cells that overexpress a sialyltransferase and which are cultured in suspension in serum-free medium a composition of EPO molecules is obtained which has on average about 1.2-1.8 Lewis-X structures and about 9 sialic acids per EPO molecule (see entry 2 in Table 4). In certain embodiments, the invention therefore provides a composition comprising one or more isoforms of an erythropoietin (EPO) comprising glycans linked thereto, wherein said glycans comprise on average: a) between 1 and 2 Lewis-X structures per EPO molecule, and b) between 8 and 10 sialic acid moieties per EPO molecule.

Such compositions can be used to further purify and obtain even more preferred compositions, having average sialic acid content that is still higher. The invention therefore also provides a composition comprising one or more isoforms of an erythropoietin (EPO) comprising glycans linked thereto, wherein said glycans comprise on average: a) at least 0.5 Lewis-X structure per EPO molecule, and b) at least 10 sialic acid moieties per EPO molecule. Preferably, such compositions comprise on average at least 11 sialic acid moieties per EPO molecule. It is shown herein that upon separation, EPO fractions can be obtained that comprise on average about 0.6 Lewis-X structures and about 12.6 sialic acid moieties per EPO molecule (see entry 3 in Table 4). In certain embodiments, the invention therefore provides a composition comprising one or more isoforms of an erythropoietin (EPO) comprising glycans linked thereto, wherein said glycans comprise on average: a) between 0.5 and 1 Lewis-X structures per EPO molecule, and b) between 11 and 13 sialic acid moieties per EPO molecule. For comparison, a commercially available EPO preparation analyzed in the same manner does not comprise Lewis-X structures and on average contained about 12.4 sialic acids per EPO molecule (see entry 4 in Table 4).

An erythropoietin in these aspects preferably is human erythropoietin, a fragment of human erythropoietin, or a mutein of human erythropoietin. Such an erythropoietin should preferably be biologically active, which means that it should have at least one of the following activities: a) causing bone marrow cells to increase production of reticulocytes and red blood cells, increase hemogloblin synthesis or iron uptake (see, e.g., U.S. Pat. No. 4,703,008), and/or b) responsive cellular protective activity selected from the group consisting of protecting, maintaining, enhancing or restoring the function or viability of a responsive mammalian cell, tissue or organ, such as for instance disclosed in WO 00/61164 and WO 02/053580. The sequence of human erythropoietin is well known (e.g., U.S. Pat. No. 5,441,868; EP patent 0411678, cDNA: GenBank accession number: MI 1319). EPO muteins, analogues, peptides, or fragments binding the EPO receptor and having some kind of activity associated with EPO have for instance been described in U.S. Pat. Nos. 5,457,089, 4,835,260, 5,767,078, 5,856,292, 4,703,008, 5,773,569, 5,830,851, 5,835,382, and PCT international publications WO 95/05465, WO 97/18318 and WO 98/18926, all incorporated by reference for the purpose of disclosing EPO fragments and EPO muteins having biological activity. The EPO of the invention may also be modified, as for instance disclosed in WO 02/053580, for example, by carbamylation of one or more lysines in the EPO molecule (e.g., see, e.g., WO 02/053580, Leist et al., 2004): such modified EPO has no erythropoietic activity, but retains its tissue protective activity. Certain EPO mutants have also been found to have these properties (Leist et al., 2004), such as EPO with a mutation of serine to glutamate at position 100 (EPO-SIOOE) and EPO with a mutation of arginine to glutamate at position 103 (EPO-R103E). Lists of these and other EPO mutants have been disclosed in WO 2004/003176, incorporated herein by reference. All these modified EPO molecules and all these muteins are included within the scope of an erythropoietin according to the present invention.

To illustrate the invention, the following examples are provided, not intended to limit the scope of the invention. The human erythropoietin (EPO) molecule contains four carbohydrate chains. Three contain N-linkages to asparagines, and one contains an O-linkage to a serine residue. The importance of glycosylation in the biological activity of EPO has been well documented (Delorme et al. 1992; Yamaguchi et al. 1991). The cDNA encoding human EPO was cloned and expressed in PER.C6 cells and PER.C6/E2A cells, expression was shown, and the glycosylation pattern was analyzed.

EXAMPLES

Example 1

Construction of Basic Expression Vectors

Plasmid pcDNA3.1/Hygro(−) (Invitrogen) was digested with NruI and EcoRV, dephosphorylated at the 5' termini by Shrimp Alkaline Phosphatase (SAP, GIBCO Life Tech.) and the plasmid fragment lacking the immediate early enhancer and promoter from CMV was purified from gel. Plasmid pAdApt.TM. (Crucell NV of Leiden, NL), containing the full length CMV enhancer/promoter (−735 to +95) next to overlapping Adeno-derived sequences to produce recombinant adenovirus, was digested with AvrII, filled in with Klenow polymerase and digested with HpaI; the fragment containing the CMV enhancer and promoter was purified over agarose gel. This CMV enhancer and promoter fragment was ligated bluntiblunt to the NruI/EcoRV fragment from pcDNA3.1 /Hygro(−). The resulting plasmid was designated pcDNA2000/Hyg(−).

Figure 2A:
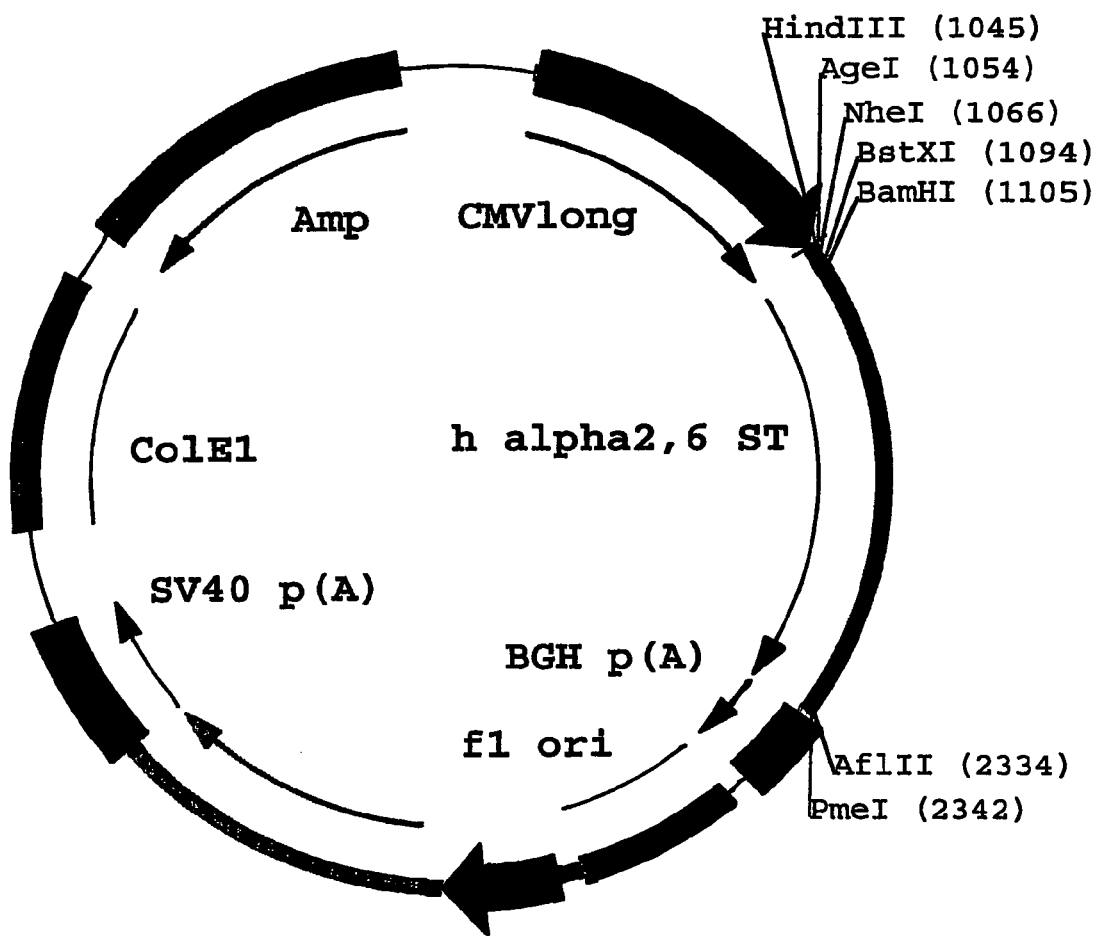
FIG. 2. Schematic representation of (A) pAlpha2,6STcDNA2000/Neo and (B) pAlpha2,6STcDNA2000/Hygro.
Figure 3A:
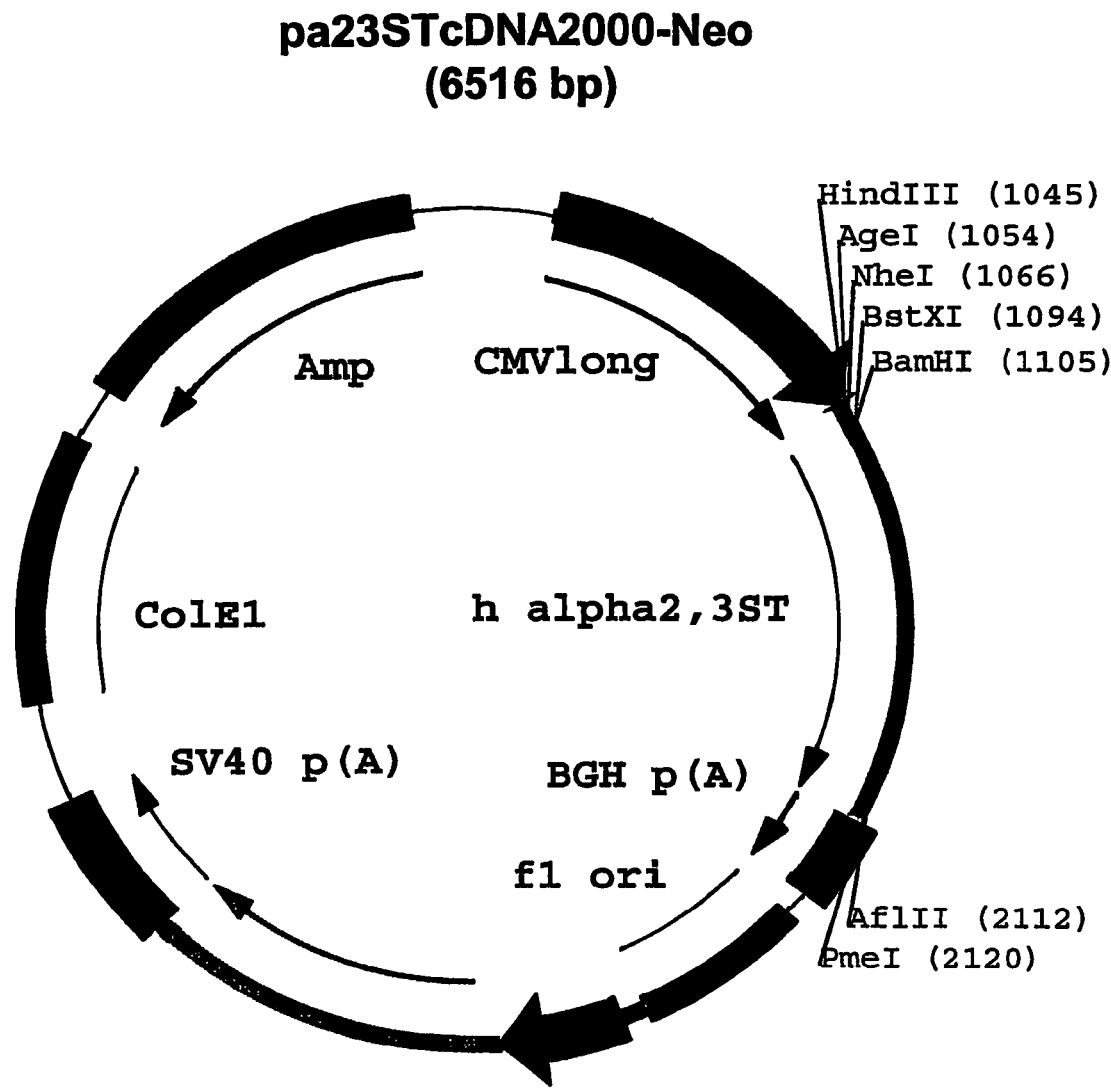
FIG. 3. Schematic representation of (A) pAlpha2,3STcDNA2000/Neo and (B) pAlpha2,3STcDNA2000/Hygro.
Figure 4:
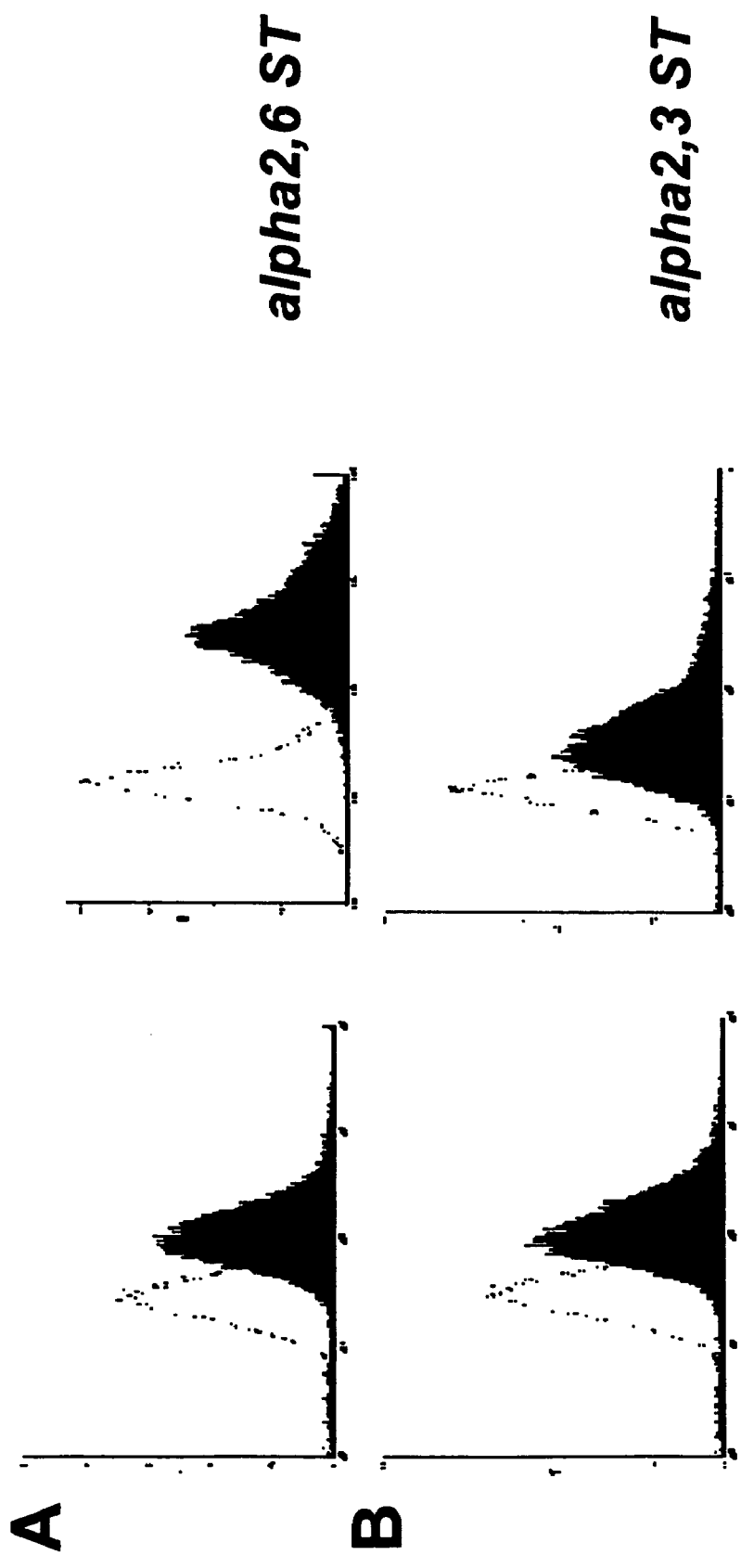
FIG. 4. Detection of (A) SAalpha2,6Gal and (B) SAlapha2,3Gal in PER.C6 and PER.C6/alpha2,6ST by FACS analysis.

Plasmid pcDNA2000/Hyg(−) was digested with PmlI, and the linearized plasmid lacking the Hygromycin resistance marker gene was purified from gel and religated. The resulting plasmid was designated pcDNA2000. Plasmid pcDNA2000 was digested with Pm1I and dephosphorylated by SAP at both termini. Plasmid pIG-GC9 containing the wild type human DHFR cDNA (Havenga et al. 1998) was used to obtain the wild type DHFR-gene by polymerase chain reaction (PCR) with introduced, noncoding Pm1I sites upstream and down stream of the cDNA. PCR primers that were used were DHFR up: 5'-GAT CCA CGT GAG ATC TCC ACC ATG GTT GGT TCG CTA AAC TG-3' (SEQ ID NO: 1), corresponding to the SEQUENCE LISTING of U.S. patent application Ser. No. 09/549,463 (the '544 patent) of Bout et al., the contents of the entirety of which are incorporated by this reference) and DHFR down: 5'-GAT CCA CGT GAG ATC TTT AAT CAT TCT TCT CAT ATAC-3' (SEQ ID NO: 2) corresponding to the incorporated '544 patent. The PCR-product was digested with Pm1I and used for ligation into pcDNA2000 (digested with Pm1I, and dephosphorylated by SAP) to obtain pcDNA2000/DHFRwt (FIG. 1 of the incorporated '544 patent). Wild type sequences and correctly used cloning sites were confirmed by double stranded sequencing. Moreover, a mutant version of the human DHFR gene (DHFRm) was used to reach a 10,000 fold higher resistance to methotrexate in PER.C6 and PER.C6/E2A by selection of a possible integration of the transgene in a genomic region with high transcriptional activity. This mutant carries an amino acid substitution in position 32 (phenylalanine to serine) and position 159 (leucine to proline) introduced by the PCR procedure. PCR on plasmid pIG-GC12 (Havenga et al. 1998) was used to obtain the mutant version of human DHFR. Cloning of this mutant is comparable to wild type DHFR. The plasmid obtained with mutant DHFR was designated pcDNA2000/DHFRm.

pIPspAdapt 6 (Galapagos Genomics of Belgium) was digested with AgeI and BamHI restriction enzymes. The resulting polylinker fragment has the following sequence: 5'-ACC GGT GAA TTC GGC GCG CCG TCG ACG ATA TCG ATC GGA CCG ACG CGT TCG CGA GCG GCC GCA ATT CGC TAG CGT TAA CGG ATC C -3' (SEQ ID NO: 3) corresponding to the incorporated '544 patent. The used AgeI and BamHI recognition sites are underlined. This fragment contains several unique restriction enzyme recognition sites and was purified over agarose gel and ligated to an AgeI/BamHI digested and agarose gel purified pcDNA2000/DHFRwt plasmid. The resulting vector was named pcDNA2001/DHFRwt (FIG. 2 of the incorporated '544 patent).

pIPspAdapt7 (Galapagos of Belgium) is digested with AgeI and BamHI restriction enzymes and has the following sequence: 5'-ACC GGT GAA TTG CGG CCG CTC GCG AAC GCG TCG TCG CGT ATC GAT ATC GTC GAC GGC GCG CCG AAT TCG CTA GCG TTA ACG GAT CC-3' (SEQ ID NO: 4) corresponding to the incorporated '544 patent. The used AgeI and BamHI recognition sites are underlined in co-pending U.S. patent application Ser. No. 10/234,007, filed Sep. 3, 2002, the contents of which are incorporated by this reference ("the '007 application"), published as U.S. patent application Publication 20030092160 to Bout et al. on May 15, 2003. The polylinker fragment contains several unique restriction enzyme recognition sites (different from pIPspAdapt6), which are purified over agarose gel and ligated to an AgeI/BamHI digested and agarose gel purified pcDNA2000/DHFRwt. This results in pcDNA2002/DHFRwt (FIG. 3 of the incorporated '544 patent).

pcDNA2000/DHFRwt was partially digested with restriction enzyme PvuII. There are two PvuII sites present in this plasmid and cloning was performed into the site between the SV40 poly(A) and ColE1, not the PvuII site down stream of the BGH poly(A). A single site digested mixture of plasmid was dephosphorylated with SAP and blunted with Klenow enzyme and purified over agarose gel. pcDNA2000/DHFRwt was digested with MunI and PvuII restriction enzymes and filled in with Klenow and free nucleotides to have both ends blunted. The resulting CMV promoter-linker-BGH poly(A)-containing fragment was isolated over gel and separated from the vector. This fragment was ligated into the partially digested and dephosphorylated vector and checked for orientation and insertion site. The resulting plasmid was named pcDNAs3000/DHFRwt (FIG. 4 of the incorporated '544 patent).

Example 2

Construction of EPO Expression Vectors

The full length human EPO cDNA was cloned, employing oligonucleotide primers EPO-START: 5' AAA AAG GAT CCG CCA CCA TGG GGG TGC ACG AAT GTC CTG CCT G-3' (SEQ ID NO: 5) corresponding to the incorporated '544 patent and EPO-STOP: 5' AAA AAG GAT CCT CAT CTG TCC CCT GTC CTG CAG GCC TC-3' (SEQ ID NO: 6) corresponding to the incorporated '544 patent (Cambridge Bioscience Ltd.) in a PCR on a human adult liver cDNA library. The amplified fragment was cloned into pUC18 linearized with BamHI. Sequence was checked by double stranded sequencing. This plasmid containing the EPO cDNA in pUC18 was digested with BamHI and the EPO insert was purified from agarose gel. Plasmids pcDNA2000/DHFRwt and pcDNA2000/DHFRm were linearized with BamHI and dephosphorylated at the 5' overhang by SAP, and the plasmids were purified from agarose gel. The EPO cDNA fragment was ligated into the BamHI sites of pcDNA2000/DHFRwt and pcDNA2000/DHFRm; the resulting plasmids were designated pEPO2000/DHFRwt (FIG. 5 of the incorporated '544 patent) and pEPO2000/DHFRm.

The plasmid pMLPI.TK (described in PCT International Patent Publication No. WO 97/00326) is an example of an adapter plasmid designed for use in combination with improved packaging cell lines like PER.C6 (described in PCT International Patent Publication No. WO 97/00326 and U.S. Pat. No. 6,033,908 to Bout et al. (Mar. 7, 2000), the contents of both of which are incorporated by this reference). First, a PCR fragment was generated from pZipDMo+PyF101(N—) template DNA (described in International Patent Application No. PCT/NL96/00195) with the following primers: LTR-1 (5'-CTG TAC GTA CCA GTG CAC TGG CCT AGG CAT GGA AAA ATA CAT AAC TG-3' (SEQ ID NO: 7) corresponding to the incorporated '544 patent and LTR-2 (5'-GCG GAT CCT TCG AAC CAT GGT AAG CTT GGT ACC GCT AGC GTT AAC CGG GCG ACT CAG TCA ATC G-3' (SEQ ID NO: 8) corresponding to the incorporated '544 patent). The PCR product was then digested with BamHI and ligated into pMLP10 (Levrero et al. 1991), that was digested with PvuII and BamHI, thereby generating vector pLTR10. This vector contains adenoviral sequences from bp 1 up to bp 454 followed by a promoter consisting of a part of the Mo-MuLV LTR having its wild-type enhancer sequences replaced by the enhancer from a mutant polyoma virus (PyF101). The promoter fragment was designated L420. Next, the coding region of the murine HSA gene was inserted. pLTR10 was digested with BstBI followed by Klenow treatment and digestion with NcoI. The HSA gene was obtained by PCR amplification on pUC18-HSA (Kay et al. 1990, using the following primers: HSA1 (5'-GCG CCA CCA TGG GCA GAG CGA TGG TGG C-3' (SEQ ID NO: 9) corresponding to the incorporated '544 patent) and HSA2 (5'-GTT AGA TCT AAG CTT GTC GAC ATC GAT CTA CTA ACA GTA GAG ATG TAG AA-3' (SEQ ID NO: 10) corresponding to the incorporated '544 patent). The 269 bp PCR fragment was subcloned in a shuttle vector using NcoI and BglII sites. Sequencing confirmed incorporation of the correct coding sequence of the HSA gene, but with an extra TAG insertion directly following the TAG stop codon. The coding region of the HSA gene, including the TAG duplication, was then excised as a NcoI/SalI fragment and cloned into a 3.5 kb NcoI/BstBI cut pLTR10, resulting in pLTR-HSA10. This plasmid was digested with EcoRI and BamHI, after which the fragment, containing the left ITR, the packaging signal, the L420 promoter and the HSA gene, was inserted into vector pMLPI.TK digested with the same enzymes and thereby replacing the promoter and gene sequences, resulting in the new adapter plasmid pAd5/L420-HSA.

The pAd5/L420-HSA plasmid was digested with AvrII and BglII followed by treatment with Klenow and ligated to a blunt 1570 bp fragment from pcDNA1/amp (Invitrogen) obtained by digestion with HhaI and AvrII followed by treatment with T4 DNA polymerase. This adapter plasmid was named pAd5/CLIP.

To enable removal of vector sequences from the left ITR, pAd5/L420-HSA was partially digested with EcoRI and the linear fragment was isolated. An oligo of the sequence 5' TTA AGT CGA C-3' (SEQ ID NO: 11) corresponding to the incorporated '544 patent was annealed to itself, resulting in a linker with a SalI site and EcoRI overhang. The linker was ligated to the partially digested pAd5/L420-HSA vector and clones were selected that had the linker inserted in the EcoRI site 23 bp upstream of the left adenovirus ITR in pAd5/L420-HSA, resulting in pAd5/L420-HSA.sal.

To enable removal of vector sequences from the left ITR, pAd5/CLIP was also partially digested with EcoRI and the linear fragment was isolated. The EcoRI linker 5' TTA AGT CGA C-3' (SEQ ID NO: 12) corresponding to the incorporated '544 patent was ligated to the partially digested pAd5/CLIP vector and clones were selected that had the linker inserted in the EcoRI site 23 bp upstream of the left adenovirus ITR, resulting in pAd5/CLIP.sal. The vector pAd5/L420-HSA was also modified to create a PacI site upstream of the left ITR. Hereto, pAd5/L420-HSA was digested with EcoRI and ligated to a PacI linker (5'-AAT TGT CTT AAT TAA CCG CTT AA-3' (SEQ ID NO: 13) corresponding to the incorporated '544 patent). The ligation mixture was digested with PacI and religated after isolation of the linear DNA from agarose gel to remove concatamerized linkers. This resulted in adapter plasmid pAd5/L420-HSA.pac.

This plasmid was digested with AvrII and BglII. The vector fragment was ligated to a linker oligonucleotide digested with the same restriction enzymes. The linker was made by annealing oligos of the following sequence: PLL-1 (5'-GCC ATC CCT AGG AAG CTT GGT ACC GGT GAA TTC GCT AGC GTT AAC GGA TCC TCT AGA CGA GAT CTG G-3' (SEQ ID NO: 14) corresponding to the incorporated '544 patent) and PLL-2 (5'-CCA GAT CTC GTC TAG AGG ATC CGT TAA CGC TAG CGA ATT CAC CGG TAC CAA GCT TCC TAG GGA TGG C-3' (SEQ ID NO: 15) corresponding to the incorporated '544 patent). The annealed linkers were separately ligated to the AvrII/BglII digested pAd5/L420-HSA.pac fragment, resulting in pAdMire.pac. Subsequently, a 0.7 kb ScaU/BsrGI fragment from pAd5/CLIP.sal containing the sal linker was cloned into the ScaI/BsrGI sites of the pAdMire.pac plasmid after removal of the fragment containing the pac linker. This resulting plasmid was named pAdMire.sal.

Plasmid pAd5/L420-HSA.pac was digested with AvrII and 5' protruding ends were filled in using Klenow enzyme. A second digestion with HindIII resulted in removal of the L420 promoter sequences. The vector fragment was isolated and ligated separately to a PCR fragment containing the CMV promoter sequence. This PCR fragment was obtained after amplification of CMV sequences from pCMVLacI (Stratagene) with the following primers: CMVplus (5'-GAT CGG TAC CAC TGC AGT GGT CAA TAT TGG CCA TTA GCC-3' (SEQ ID NO: 16) corresponding to the incorporated '544 patent) and CMVminA (5'-GAT CAA GCT TCC AAT GCA CCG TTC CCG GC-3' (SEQ ID NO: 17) corresponding to the incorporated '544 patent). The PCR fragment was first digested with PstI after which the 3'-protruding ends were removed by treatment with T4 DNA polymerase. Then the DNA was digested with HindIII and ligated into the AvrII/HindIII digested pAd5/L420-HSA.pac vector. The resulting plasmid was named pAd5/CMV-HSA.pac. This plasmid was then digested with HindIII and BamHI and the vector fragment was isolated and ligated to the HindIII/BglII polylinker sequence obtained after digestion of pAdMire-.pac. The resulting plasmid was named pAdApt.pac and contains nucleotides −735 to +95 of the human CMV promoter/enhancer (Boshart M. et al., 1985).

Figure 6:
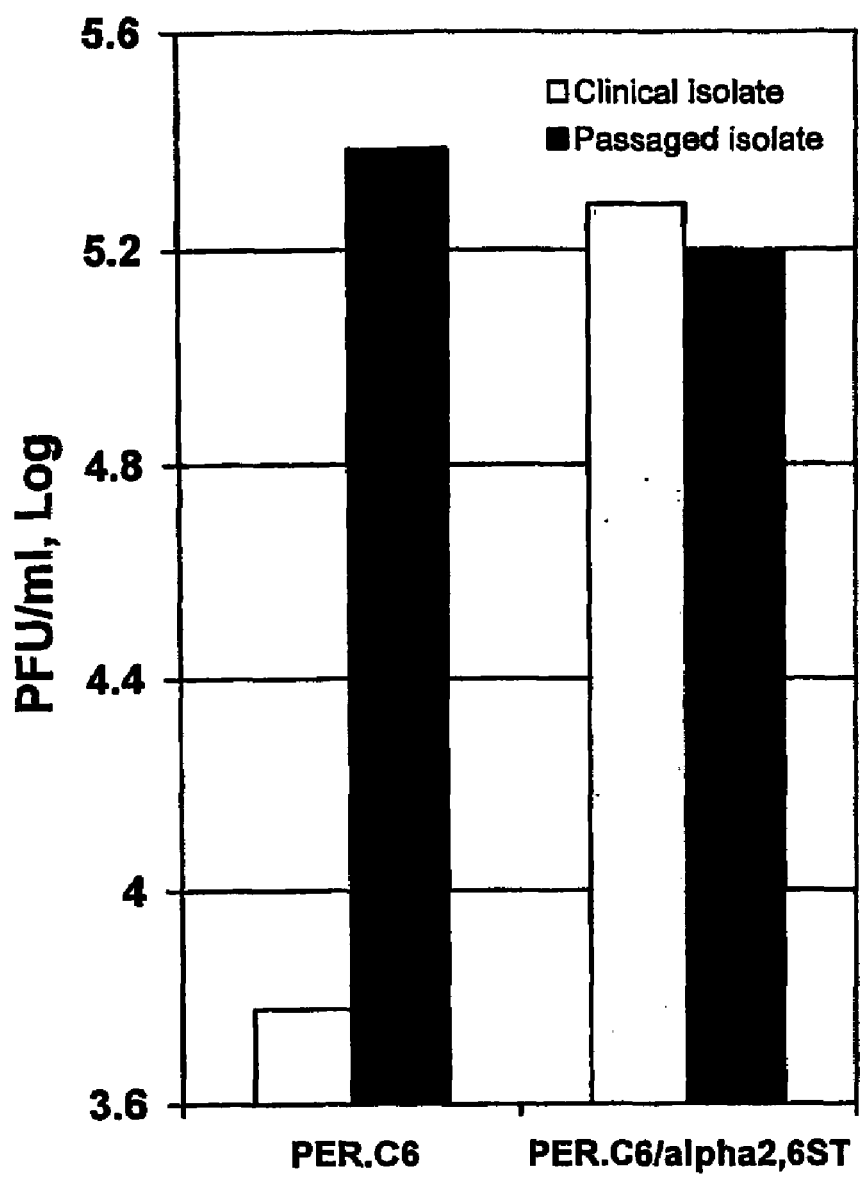
FIG. 6. Propagation of a primary clinical influenza isolate and a egg-passaged influenza batch (from the same primary isolate) on PER.C6 and PER.C6/alpha2,6ST, determined by plaque assay. Infectivity is expressed as plaque-forming units (pfu's) per ml.

The full length human EPO cDNA (GenBank accession number: MI 1319) containing a perfect Kozak sequence for proper translation was removed from the pUC18 backbone after a BamHI digestion. The cDNA insert was purified over agarose gel and ligated into pAdApt.pac, which was also digested with BamHI, subsequently dephosphorylated at the 5' and 3' insertion sites using SAP and also purified over agarose gel to remove the short BamHI-BamHI linker sequence. The obtained circular plasmid was checked with KpnI, DdeI and NcoI restriction digestions that all gave the right size bands. Furthermore, the orientation and sequence was confirmed by double stranded sequencing. The obtained plasmid with the human EPO cDNA in the correct orientation was named pAdApt.EPO (FIG. 6 of the incorporated '544 patent).

Example 3

Construction of UBS-54 Expression Vectors

The constant domains (CH1, -2 and -3) of the heavy chain of the human immunoglobulin G1 (IgG1) gene including intron sequences and connecting ('Hinge') domain were generated by PCR using an upstream and a down stream primer. The sequence of the upstream primer (CAMH-UP) is 5'-GAT CGA TAT CGC TAG CAC CAA GGG CCC ATC GGT C-3' (SEQ ID NO: 18) corresponding to the incorporated '544 patent, in which the annealing nucleotides are depicted in italics and two sequential restriction enzyme recognition sites (EcoRV and NheI) are underlined.

The sequence of the down stream primer (CAMH-DOWN) is: 5'-GAT CGT TTA AAC TCA TTT ACC CGG AGA CAG-3' (SEQ ID NO: 19) corresponding to the incorporated '544 patent, in which the annealing nucleotides are depicted in italics and the introduced PmeI restriction enzyme recognition site is underlined.

The order in which the domains of the human IgG1 heavy chain were arranged is as follows: CH1-intron-Hinge-intron-CH2-intron-CH3. The PCR was performed on a plasmid (pCMgamma NEO Skappa Vgamma Cgamma hu) containing the heavy chain of a humanized antibody directed against D-dimer from human fibrinogen (Vandamme et al. 1990). This antibody was designated "15C5" and the humanization was performed with the introduction of the human constant domains including intron sequences (Bulens et al. 1991). The PCR resulted in a product of 1621 nucleotides. The NheI and PmeI sites were introduced for easy cloning into the pcDNA2000/Hyg(−) polylinker. The NheI site encoded two amino acids (Ala and Ser) that are part of the constant region CH1, but that did not hybridize to the DNA present in the template (Crowe et al. 1992).

The PCR product was digested with NheI and PmeI restriction enzymes, purified over agarose gel and ligated into a NheI and PmeI digested and agarose gel purified pcDNA2000/Hygro(−). This resulted in plasmid pHC2000/Hyg(−) (FIG. 7 of the incorporated '544 patent), which can be used for linking the human heavy chain constant domains, including introns to any possible variable region of any identified immunoglobulin heavy chain for humanization.

The constant domain of the light chain of the human immunoglobulin (IgG1) gene was generated by PCR using an upstream and a down stream primer: The sequence of the upstream primer (CAML-UP) is 5'-GAT CCG TAC GGT GGC TGCACCATC TGT C-3' (SEQ ID NO: 20) corresponding to the incorporated '544 patent, in which the annealing nucleotides are depicted in italics and an introduced SunI restriction enzyme recognition site is underlined.

The sequence of the down stream primer (CAML-DOWN) is 5'-GAT CGT TTA AAC CTA ACA CTC TCC CCT GTT G-3' (SEQ ID NO: 21) corresponding to the incorporated '544 patent, in which the annealing nucleotides are in italics and an introduced PmeI restriction enzyme recognition site is underlined.

The PCR was performed on a plasmid (pCMkappa DHFR13 15C5 kappa humanized) carrying the murine signal sequence and murine variable region of the light chain of 15C5 linked to the constant domain of the human IgG1 light chain (Vandamme et al. 1990; Bulens et al. 1991).

The PCR resulted in a product of 340 nucleotides. The SunI and PmeI sites were introduced for cloning into the pcDNA2001/DHFRwt polylinker. The SunI site encoded two amino acids (Arg and Thr) of which the threonine residue is part of the constant region of human immunoglobulin light chains, while the arginine residue is part of the variable region of CAMPATH-1H (Crowe et al. 1992). This enabled subsequent 3' cloning into the SunI site, which was unique in the plasmid.

The PCR product was digested with SunI and PmeI restriction enzymes purified over agarose gel, ligated into a BamHI, PmeI digested, and agarose gel purified pcDNA2001/DHFRwt, which was blunted by Klenow enzyme and free nucleotides. Ligation in the correct orientation resulted in loss of the BamHI site at the 5' end and preservation of the SunI and PmeI sites. The resulting plasmid was named pLC2001/DHFRwt (FIG. 8 of the incorporated '544 patent), which plasmid can be used for linking the human light chain constant domain to any possible variable region of any identified immunoglobulin light chain for humanization.

pNUT-C gamma (Huls et al., 1999) contains the constant domains, introns and hinge region of the human IgG1 heavy chain (Huls et al. 1999) and received the variable domain upstream of the first constant domain. The variable domain of the gamma chain of fully humanized monoclonal antibody UBS-54 is preceded by the following leader peptide sequence: MACPGFLWALVISTCLEFSM (SEQ ID NO: 22) corresponding to the incorporated '544 patent (sequence: 5'-ATG GCA TGC CCT GGC TTC CTG TGG GCA CTT GTG ATC TCC ACC TGT CTT GAA TTT TCC ATG-3') (SEQ ID NO: 23) corresponding to the incorporated '544 patent. This resulted in an insert of approximately 2 kb in length. The entire gamma chain was amplified by PCR using an upstream primer (UBS-UP) and the down stream primer CAMH-DOWN. The sequence of UBS-UP is as follows: 5'-GAT CAC GCG TGC TAG CCA CCA TGG CAT GCC CTG GCT TC-3' (SEQ ID NO: 24) corresponding to the incorporated '544 patent in which the introduced MluI and NheI sites are underlined and the perfect Kozak sequence is italicized.

Figure 9:
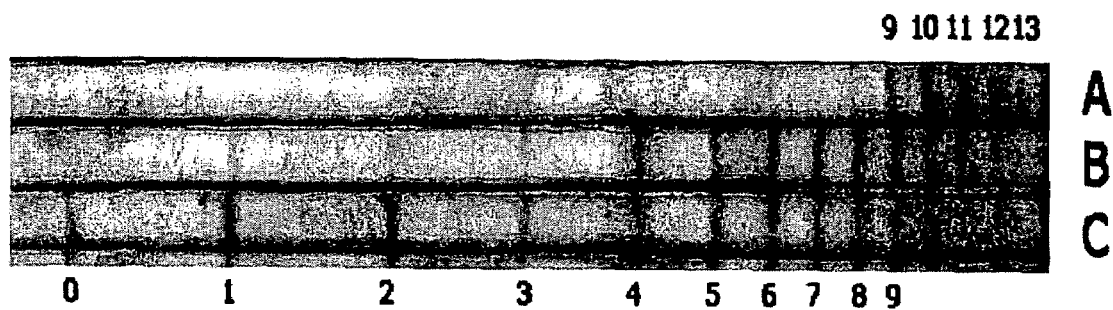
FIG. 9. Sialic acid content as determined by iso-electric focusing of commercially available EPO (EPREX™, lane A), EPO produced in PER.C6-EPO-ST clone 25-3.10 (lane B), and EPO produced in PER.C6-EPO clone 25 (lane C). The putative number of sialic acids per EPO molecule is also shown.

The resulting PCR product was digested with NheI and PmeI restriction enzymes, purified over agarose gel and ligated to the pcDNA2000/Hygro(−) plasmid that is also digested with NheI and PmeI, dephosphorylated with tSAP and purified over gel. The resulting plasmid was named pUBS-Heavy2000/Hyg(−) (FIG. 9 of the incorporated '544 patent). pNUT-C kappa contains the constant domain of the light chain of human IgG1 kappa (Huls et al. 1999) and received the variable domain of fully humanized monoclonal antibody UBS-54 kappa chain preceded by the following leader peptide: MACPGFLWALVISTCLEFSM (SEQ ID NO: 25) corresponding to the incorporated '544 patent (sequence: 5'-ATG GCA TGC CCT GGC TTC CTG TGG GCA CTT GTG ATC TCC ACC TGT CTT GAA TTT TCC ATG -3' (SEQ ID NO: 26) corresponding to the incorporated '544 patent, for details on the plasmid see U-BiSys of Utrecht, NL). This resulted in an insert of approximately 1.2 kb in length.

Figure 11:
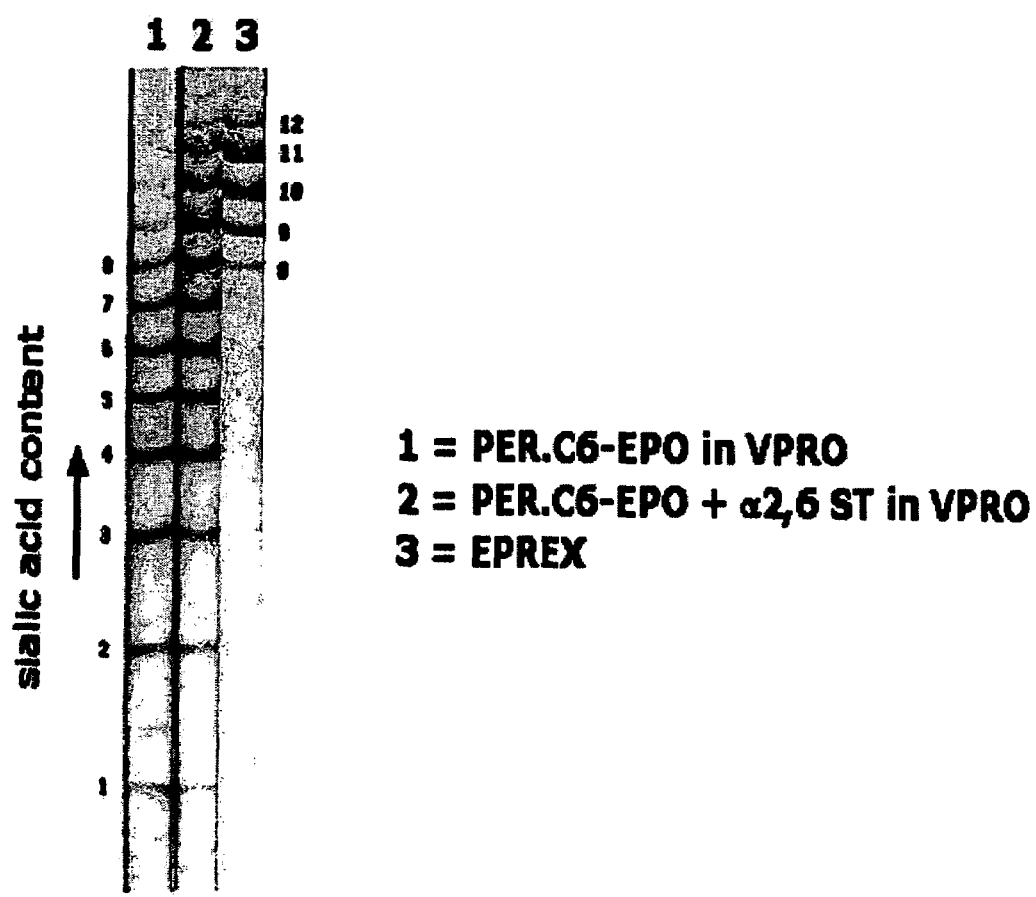
FIG. 11. Sialic acid content as determined by iso-electric focusing of EPO produced in PER.C6 cells that do not over-express sialyltransferase in a serum-free suspension culture in VPRO medium (lane 1), of EPO produced in PER.C6 cells that over-express $\alpha$-2,6-sialyltransferase (i.e., PER.C6-EPO-ST clone 25-3.10) in a serum-free suspension culture in VPRO (lane 2), and of commercially available EPO, i.e., EPREX™ (lane 3).

The entire insert was amplified by PCR using the upstream primer UBS-UP and the down stream primer CAML-DOWN, hereby modifying the translation start site. The resulting PCR product was digested with NheI and PmeI restriction enzymes, purified over agarose gel and ligated to pcDNA2001/DHFRwt that was also digested with NheI and PmeI, dephosphorylated by tSAP and purified over gel, resulting in pUBS-Light2001/DHFRwt (FIG. 10 of the incorporated '544 patent). To remove the extra intron which is located between the variable domain and the first constant domain that is present in pNUT-Cgamma and to link the signal peptide and the variable domain to the wild type constant domains of human IgG1 heavy chain, lacking a number of polymorphisms present in the carboxy-terminal constant domain in pNUT-Cgamma, a PCR product is generated with primer UBS-UP and primer UBSHV-DOWN that has the following sequence: 5'-GAT CGC TAG CTG TCGAGA CGG TGA CCA G -3' (SEQ ID NO: 27) corresponding to the incorporated '544 patent, in which the introduced NheI site is underlined and the annealing nucleotides are italicized. The resulting PCR product is digested with NheI restriction enzyme, purified over gel and ligated to a NheI digested and SAP-dephosphorylated pHC2000/Hyg(−) plasmid that was purified over gel. The plasmid with the insert in the correct orientation and reading frame is named pUBS2-Heavy2000/Hyg(−) (FIG. 11 of the incorporated '544 patent).

For removal of an extra intron which is located between the variable domain and the constant domain that is present in pNUT-Ckappa and to link the signal peptide and the variable domain to the wild type constant domain of human IgG1 light chain, a PCR product was generated with primer UBS-UP and primer UBSLV-DOWN that has the following sequence: 5'-GAT CCG TAC GCT TGA TCT CCA CCT TGG TC -3' (SEQ ID NO: 28) corresponding to the incorporated '544 patent, in which the introduced SunI site is underlined and the annealing nucleotides are in bold. Then the resulting PCR product was digested with MluI and SunI restriction enzymes, purified over gel and ligated to a MluI and SunI digested pLC2001/DHFRwt plasmid that was purified over gel. The resulting plasmid was named pUBS2-Light2001/DHFRwt (FIG. 12 of the incorporated '544 patent).

Figure 13:
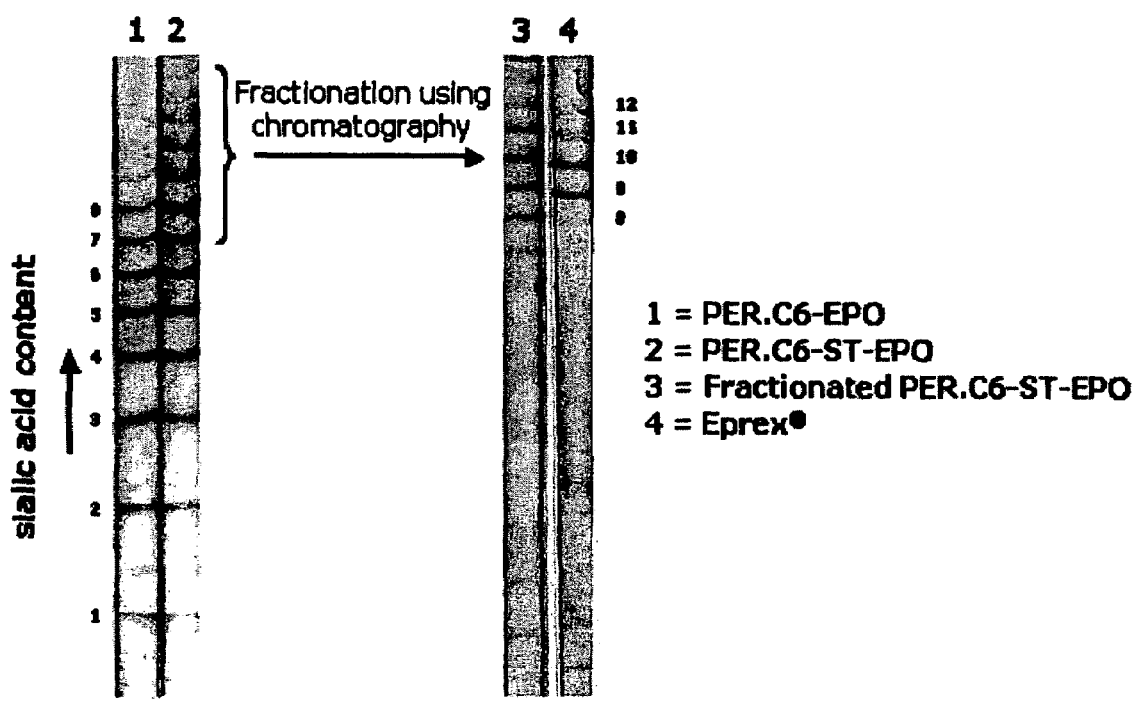
FIG. 13. Iso-electric focusing of various PER.C6-EPO preparations and EPREX. PER.C6-EPO represents the total pool of EPO molecules produced by PER.C6 cells that do not over-express $\alpha$-s,6-sialyltransferase; PER.C6-ST-EPO represents the total pool of EPO molecules produced by PER.C6 cells that do over-express $\alpha$-s,6-sialyltransferase. Fractionated PER.C6-ST-EPO represents the highly sialylated EPO obtained from the material shown in lane 2 using the fractionation/purification protocol that is described in Example 48. EPREX represents a commercially available EPO preparation.
Figure 14:
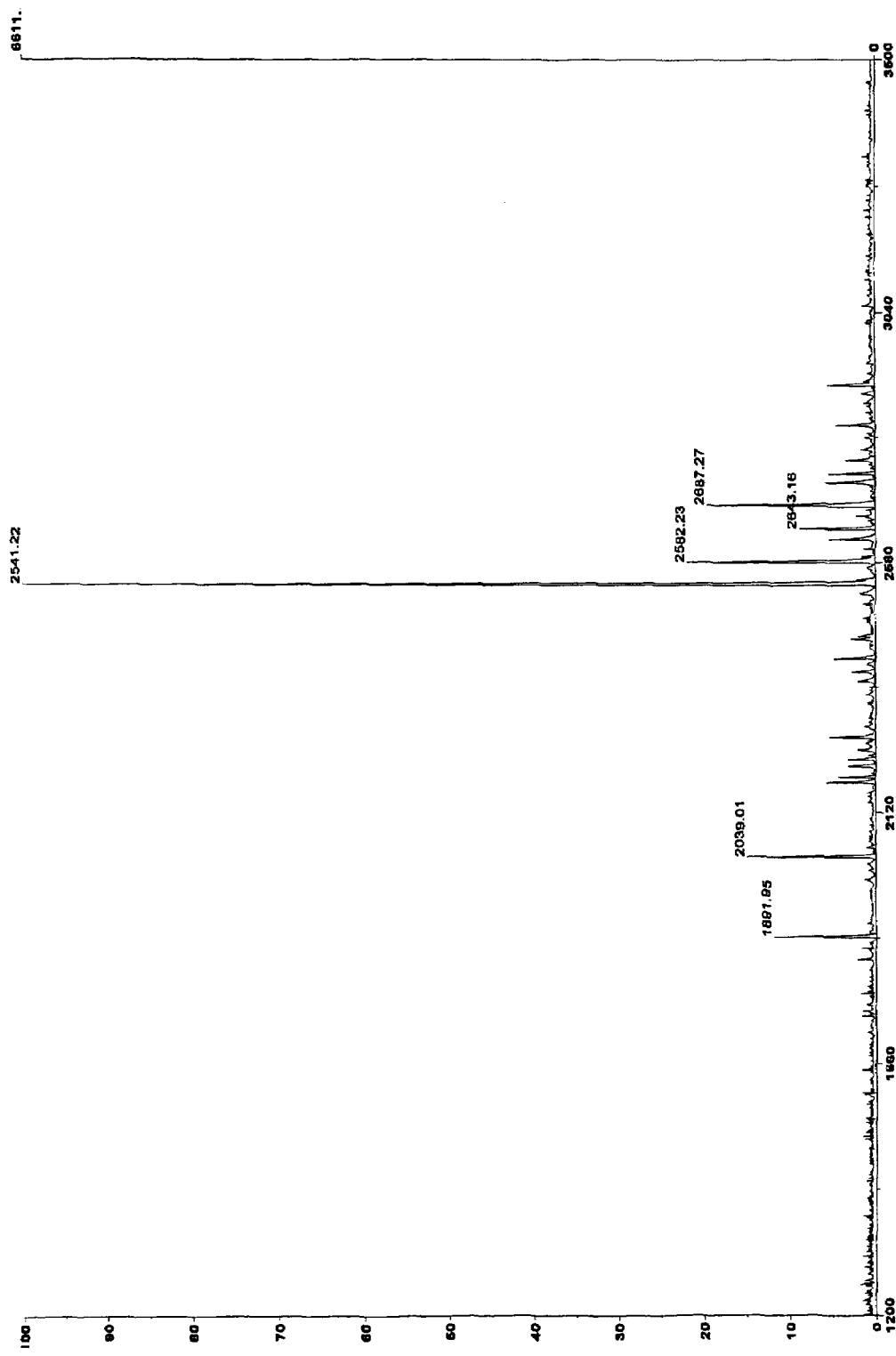
FIG. 14. MALDI-MS spectrum of the desialylated N-linked sugars of fractionated, highly sialylated PER.C6-EPO as obtained using the procedures described in Example 48.

The PCR product of the full-length heavy chain of UBS-54 is digested with NheI and PmeI restriction enzymes and blunted with Klenow enzyme. This fragment is ligated to the plasmid pcDNAs3000/DHFRwt that is digested with BstXI restriction enzyme, blunted, dephosphorylated by SAP and purified over gel. The plasmid with the heavy chain insert is named pUBS-Heavy3000/DHFRwt. Subsequently, the PCR of the light chain is digested with MluI and PmeI restriction enzymes, blunted, purified over gel and ligated to pUBS-Heavy3000/DHFRwt that is digested with HpaI, dephosphorylated by tSAP and purified over gel. The resulting vector is named pUBS-3000/DHFRwt (FIG. 13 of the incorporated '544 patent). The gene that encodes the heavy chain of UBS-54 without an intron between the variable domain and the first constant region and with a wild type carboxy terminal constant region (2031 nucleotides) is purified over gel after digestion of pUBS2-2000/Hyg(−) with EcoRI and PmeI and treatment with Klenow enzyme and free nucleotides to blunt the EcoRI site. Subsequently, the insert is ligated to a pcDNAs3000/DHFRwt plasmid that is digested with BstXI, blunted, dephosphorylated with SAP and purified over gel. The resulting plasmid is named pUBS2-Heavy3000/DHFRwt. pUBS2-Light2001/DHFRwt is then digested with EcoRV and PmeI, and the 755 nucleotide insert containing the signal peptide linked to the variable domain of the kappa chain of UBS-54 and the constant domain of human IgG1 kappa chain without an intron sequence is purified over gel and ligated to pUBS2-Heavy3000/DHFRwt that is digested with HpaI, dephosphorylated with tSAP and purified over gel. The resulting plasmid is named pUBS2-3000/DHFRwt (FIG. 14 of the incorporated '544 patent).

Plasmid pRc/CMV (Invitrogen) was digested with BstBI restriction enzymes, blunted with Klenow enzyme and subsequently digested with XmaI enzyme. The Neomycin resistance gene containing fragment was purified over agarose gel and ligated to pUBS-Light2001/DHFRwt plasmid that was digested with XmaI and Pm1I restriction enzymes, followed by dephosphorylation with SAP and purified over gel to remove the DHFR cDNA. The resulting plasmid was named pUBS-Light2001/Neo(−). The fragment was also ligated to a XmaI/Pm1I digested and gel purified pcDNA2001/DHFRwt plasmid resulting in pcDNA2001/Neo. The PCR product of the UBS-54 variable domain and the digested and purified constant domain PCR product were used in a three-point ligation with a MluI/PmeI digested pcDNA2001/Neo. The resulting plasmid was named pUBS2-Light2001/Neo.

Example 4

Construction of CAMPATH-1H Expression Vectors

Cambridge Bioscience Ltd. (UK) generates a 396 nucleotide fragment containing a perfect Kozak sequence followed by the signal sequence and the variable region of the published CAMPATH-1H light chain (Crowe et al. 1992). This fragment contains, on the 5' end, an introduced and unique HindIII site and, on the 3' end, an introduced and unique SunI site and is cloned into an appropriate shuttle vector. This plasmid is digested with HindIII and SunI and the resulting CAMPATH-1H light chain fragment is purified over gel and ligated into a HindIu/SunI digested and agarose gel purified pLC2001/DHFRwt. The resulting plasmid is named pCAMPATH-Light2001/DHFRwt. Cambridge Bioscience Ltd. (UK) generated a 438 nucleotide fragment containing a perfect Kozak sequence followed by the signal sequence and the published variable region of the CAMPATH-1H heavy chain (Crowe et al. 1992), cloned into an appropriate cloning vector. This product contains a unique HindIII restriction enzyme recognition site on the 5' end and a unique NheI restriction enzyme recognition site on the 3' end. This plasmid was digested with HindII and NheI and the resulting CAMPATH-1H heavy chain fragment was purified over gel and ligated into a purified and HindIII/NheI digested pHC2000/Hyg(−). The resulting plasmid was named pCAMPATH-Heavy2000/Hyg(−).

Example 5

Construction of 15C5 Expression Vectors

The heavy chain of the humanized version of the monoclonal antibody 15C5 directed against human fibrin fragment D-dimer (Bulens et al. 1991; Vandamme et al. 1990)

consisting of human constant domains including intron sequences, hinge region and variable regions preceded by the signal peptide from the 15C5 kappa light chain is amplified by PCR on plasmid "pCMgamma NEO Skappa Vgamma Cgamma hu" as a template using CAMH-DOWN as a down stream primer and 15C5-UP as the upstream primer. 15C5-UP has the following sequence: 5'-GA TCA CGC GTG CTA GCC ACC ATG GGT ACT CCT GCT CAG TTT CTT GGA ATC-3' (SEQ ID NO: 29) corresponding to the incorporated '544 patent, in which the introduced MluI and NheI restriction recognition sites are underlined and the perfect Kozak sequence is italicized. To properly introduce an adequate Kozak context, the adenine at position +4 (the adenine in the ATG start codon is +1) is replaced by a guanine, resulting in a mutation from an arginine into a glycine amino acid. To prevent primer dimerization, position +6 of the guanine is replaced by a thymine and the position +9 of the cytosine is replaced by thymine. This latter mutation leaves the threonine residue intact. The resulting PCR was digested with NheI and PmeI restriction enzymes, purified over gel and ligated to a NheI and PmeI digested pcDNA2000/Hygro(-), that is dephosphorylated by SAP and purified over agarose gel. The resulting plasmid is named p15C5-Heavy2000/Hyg(-). The light chain of the humanized version of the monoclonal antibody 15C5 directed against human fibrin fragment D-dimer (Bulens et al. 1991; Vandamme et al. 1990) consisting of the human constant domain and variable regions preceded by a 20 amino acid signal peptide is amplified by PCR on plasmid pCMkappa DHFR13 15C5kappa hu as a template, using CAML-DOWN as a down stream primer and 15C5-UP as the upstream primer. The resulting PCR is digested with NheI and PmeI restriction enzymes, purified over gel and ligated to a NheI and PmeI digested pcDNA2001/DHFRwt that is dephosphorylated by SAP and purified over agarose gel. The resulting plasmid is named p15C5-Light2001/DHFRwt.

Example 6

Establishment of Methotrexate Hygromycin and G418 Selection Levels.

PER.C6 and PER.C6/E2A were seeded in different densities. The starting concentration of methotrexate (MTX) in these sensitivity studies ranged between 0 nM and 2500 nM. The concentration which was just lethal for both cell lines was determined; when cells were seeded in densities of 100,000 cells per well in a 6-well dish, wells were still 100% confluent at 10 nM and approximately 90-100% confluent at 25 nM, while most cells were killed at a concentration of 50 nM and above after 6 days to 15 days of incubation. These results are summarized in Table 1 of the incorporated '007 application. PER.C6 cells were tested for their resistance to a combination of Hygromycin and G418 to select outgrowing stable colonies that expressed both heavy and light chains for the respective recombinant monoclonal antibodies encoded by plasmids carrying either a hygromycin or a neomycin resistance gene. When cells were grown on normal medium containing 100 ug/ml hygromycin and 250 ug/ml G418, non-transfected cells were killed and stable colonies could appear. (See, Example 7).

CHO-dhfr cells ATCC deposit:CRL9096 are seeded in different densities in their respective culture medium. The starting concentration of methotrexate in these sensitivity studies ranges from approximately 0.5 nM to 500 nM. The concentration, which is just lethal for the cell line, is determined and subsequently used directly after growth selection on hygromycin in the case of IgG heavy chain selection (hyg) and light chain selection (dhfr).

Example 7

Transfection of EPO Expression Vectors to Obtain Stable Cell Lines

Cells of cell lines PER.C6 and PER.C6/E2A were seeded in 40 tissue culture dishes (10 cm diameter) with approximately 2-3 million cells/dish and were kept overnight under their respective conditions (10% $CO_2$ concentration and temperature, which is 39° C. for PER.C6/E2A and 37° C. for PER.C6). The next day, transfections were all performed at 37° C. using Lipofectamine (Gibco). After replacement with fresh (DMEM) medium after 4 hours, PER.C6/E2A cells were transferred to 39° C. again, while PER.C6 cells were kept at 37° C. Twenty dishes of each cell line were transfected with 5 ug ScaI digested pEPO2000/DHFRwt and twenty dishes were transfected with 5 ug ScaI digested pEPO2000/DHFRm, all according to standard protocols. Another 13 dishes served as negative controls for methotrexate killing and transfection efficiency, which was approximately 50%. On the next day, MTX was added to the dishes in concentrations ranging between 100 and 1000 nM for DHFRwt and 50,000 and 500,000 nM for DHFRm dissolved in medium containing dialyzed FBS. Cells were incubated over a period of 4-5 weeks. Tissue medium (including MTX) was refreshed every two-three days. Cells were monitored daily for death, comparing between positive and negative controls. Outgrowing colonies were picked and subcultured. No positive clones could be subcultured from the transfectants that received the mutant DHFR gene, most likely due to toxic effects of the high concentrations of MTX that were applied. From the PER.C6 and PER.C6/E2A cells that were transfected with the wild type DHFR gene, only cell lines could be established in the first passages when cells were grown on 100 nM MTX, although colonies appeared on dishes with 250 and 500 nM MTX. These clones were not viable during subculturing, and were discarded.

Example 8

Sub-Culturing of Transfected Cells

From each cell line, approximately 50 selected colonies that were resistant to the threshold MTX concentration were grown subsequently in 96-well, 24-well, and 6-well plates and T25 flasks in their respective medium plus MTX. When cells reached growth in T25 tissue culture flasks, at least one vial of each clone was frozen and stored, and was subsequently tested for human recombinant EPO production. For this, the commercial ELISA kit from R&D Systems was used (Quantikine IVD human EPO, Quantitative Colorimetric Sandwich ELISA, cat.# DEPOO). Since the different clones appeared to have different growth characteristics and growth curves, a standard for EPO production was set as follows: At day 0, cells were seeded in T25 tissue culture flasks in concentrations ranging between 0.5 to 1.5 million per flask. At day 4, supernatant was taken and used in the EPO ELISA. From this, the production level was set as ELISA units per million seeded cells per day. (U/1E6/day) A number of these clones are given in Table 2 of the incorporated '007 patent application.

The following selection of good producer clones was based on high expression, culturing behavior and viability. To allow checks for long-term viability, suspension growth in roller bottles and bioreactor during extended time periods, more vials of the best producer clones were frozen, and the following best producers of each cell line were selected for further investigations P8, P9, E17 and E55 in which "P"

stands for PER.C6 and "E" stands for PER.C6/E2A. These clones are subcultured and subjected to increasing doses of methotrexate in a time span of two months. The concentration starts at the threshold concentration and increases to approximately 0.2 mM. During these two months, EPO ELISA experiments are performed on a regular basis to detect an increase in EPO production. At the highest methotrexate concentration, the best stable producer is selected and compared to the amounts from the best CHO clone and used for cell banking (RL). From every other clone, 5 vials are frozen. The number of amplified EPO cDNA copies is detected by Southern blotting.

Example 9

EPO Production in Bioreactors

The best performing EPO producing transfected stable cell line of PER.C6, P9, was brought into suspension and scaled up to 1 to 2 liter fermentors. To get P9 into suspension, attached cells were washed with PBS and subsequently incubated with JRH ExCell 525 medium for PER.C6 (JRH Biosciences), after which the cells loosen from the flask and form the suspension culture. Cells were kept at two concentrations of MTX: 0 nM and 100 nM. General production levels of EPO that were reached at these concentrations (in roller bottles) were respectively 1500 and 5700 units per million seeded cells per day. Although the lower yields in the absence of MTX can be explained by removal of the integrated DNA, it seems as if there is a shut-down effect of the integrated DNA since cells that are kept at lower concentrations of MTX for longer periods of time are able to reach their former yields when they are transferred to 100 nM MTX concentrations again. (See, Example 11).

Suspension P9 cells were grown normally with 100 nM MTX and used for inoculation of bioreactors. Two bioreactor settings were tested: perfusion and repeated batch cultures.

A. Perfusion in a 2 Liter Bioreactor.

Figure 15:
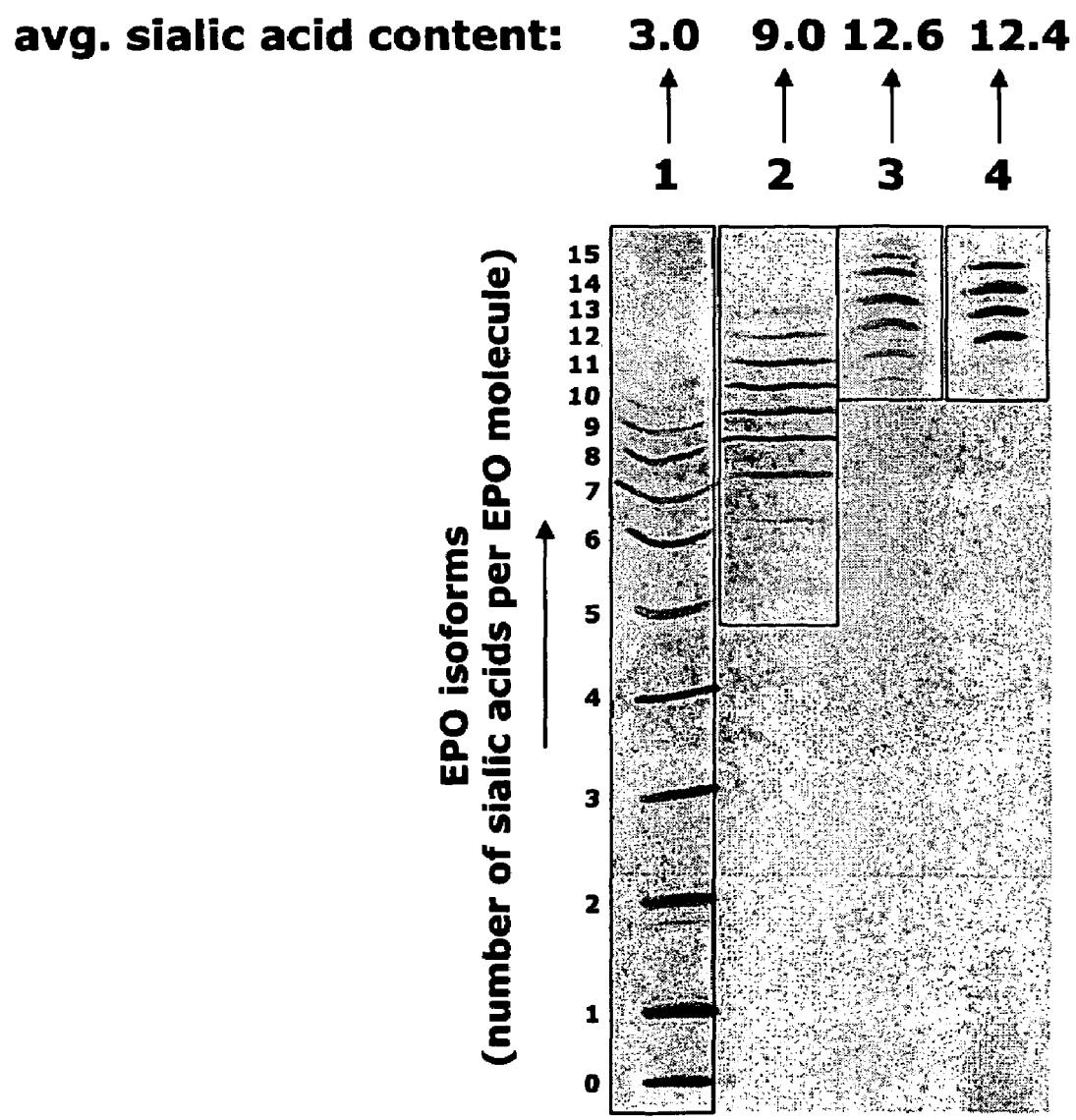
FIG. 15. EPO isoforms with different sialic acid contents as described in this application. 1: EPO produced by PER.C6 without over-expression of sialyltransferase (example 44). 2: EPO produced by PER.C6 with over-expression of $\alpha$-2,6-sialyltransferase (example 45). 3: fractionated highly sialylated EPO (example 48). 4: EPREXO (commercially available EPO). See Example 50.

Cells were seeded at a concentration of $0.5 \times 10^6$ cells per ml and perfusion was started at day 3 after cells reached a density of approximately $2.3 \times 10^6$ cells per ml. The perfusion rate was 1 volume per 24 hours with a bleed of approximately 250 ml per 24 hours. In this setting, P9 cells stayed at a constant density of approximately $5 \times 10^6$ cells per ml and a viability of almost 95% for over a month. The EPO concentration was determined on a regular basis and is shown in FIG. 15 (of the incorporated '544 patent). In the 2 liter perfused bioreactor the P9 cells were able to maintain a production level of approximately 6000 ELISA units per ml. With a perfusion rate of 1 working volume per day (1.5 to 1.6 liter), this means that in this 2 liter setting, the P9 cells produced approximately $1 \times 10^7$ units per day per 2 liter bioreactor in the absence of MTX.

B. Repeated Batch in a 2 Liter Bioreactor

P9 suspension cells that were grown on roller bottles were used to inoculate a 2 liter bioreactor in the absence of MTX and were left to grow until a density of approximately 1.5 million cells per ml, after which a third of the population was removed (+/-1 liter per 2 to 3 days) and the remaining culture was diluted with fresh medium to reach again a density of 0.5 million cells per ml. This procedure was repeated for 3 weeks and the working volume was kept at 1.6 liter. EPO concentrations in the removed medium were determined and shown in FIG. 16 of the incorporated '544 patent. The average concentration was approximately 3000 ELISA units per ml. With an average period of 2 days after which the population was diluted, this means that, in this 2 liter setting, the P9 cells produced approximately $1.5 \times 10^6$ units per day in the absence of MTX.

C. Repeated Batch in a 1 liter Bioreactor with Different Concentrations of Dissolved Oxygen, Temperatures and pH Settings.

Figure 17:
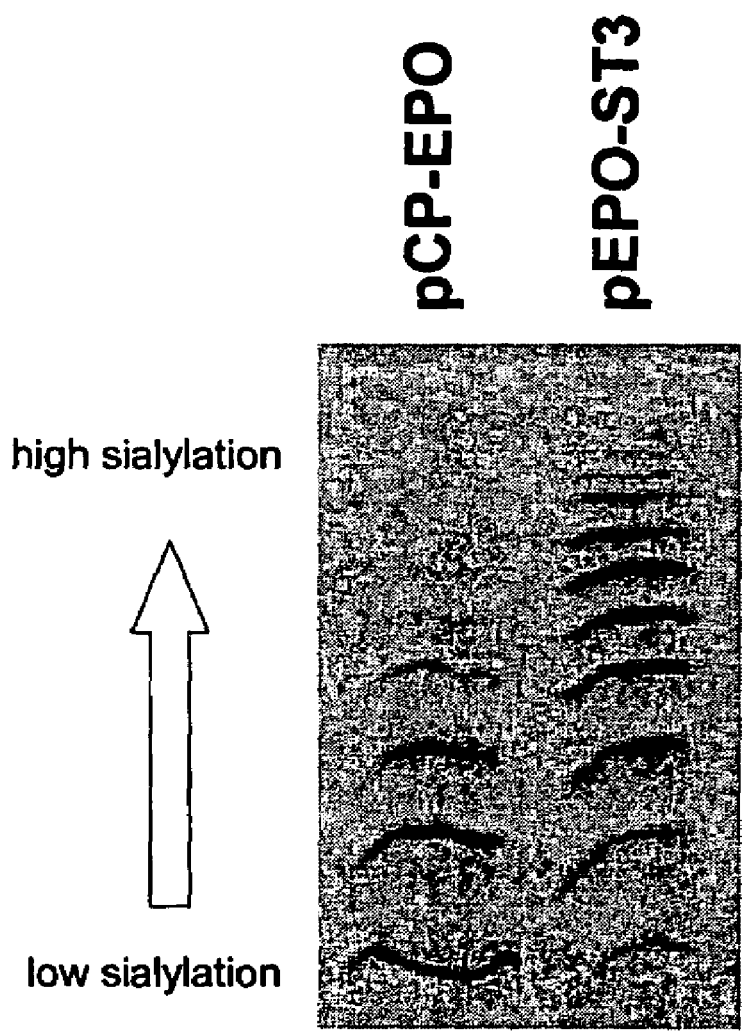
FIG. 17. Iso-electric focusing (IEF) gel of EPO produced in PER.C6 cells (pCP-EPO) and of EPO produced in PER.C6 cells under concomitant over-expression of human $\alpha$-2,3-sialyltransferase (pEPO-ST3), after transient transfection. See example 52 for details.

Fresh P9 suspension cells were grown in the presence of 100 nM MTX in roller bottles and used for inoculation of 4×1 liter bioreactors to a density of 0.3 million cells per ml in JRH ExCell 525 medium. EPO yields were determined after 3, 5 and 7 days. The first settings that were tested were: 0.5%, 10%, 150% and as a positive control 50% Dissolved Oxygen (% DO). 50% DO is the condition in which PER.C6 and P9 cells are normally kept. In another run, P9 cells were inoculated and tested for EPO production at different temperatures (32° C., 34° C., 37° C. and 39° C.) in which 37° C. is the normal setting for PER.C6 and P9, and in the third run, fresh P9 cells were inoculated and tested for EPO production at different pH settings (pH 6.5, pH 6.8, pH 7.0 and pH 7.3). PER.C6 cells are normally kept at pH 7.3. An overview of the EPO yields (3 days after seeding) is shown in FIG. 17 of the incorporated '544 patent. Apparently, EPO concentrations increase when the temperature is rising from 32 to 39° C. as was also seen with PER.C6/E2A cells grown at 39° C. (Table 4) (of the incorporated '544 patent), and 50% DO is optimal for P9 in the range that was tested here. At pH 6.5, cells cannot survive since the viability in this bioreactor dropped beneath 80% after 7 days. EPO samples produced in these settings are checked for glycosylation and charge in 2D electrophoresis. (See, also Example 17).

Example 10

Amplification of the DHFR Gene

Figure 18:
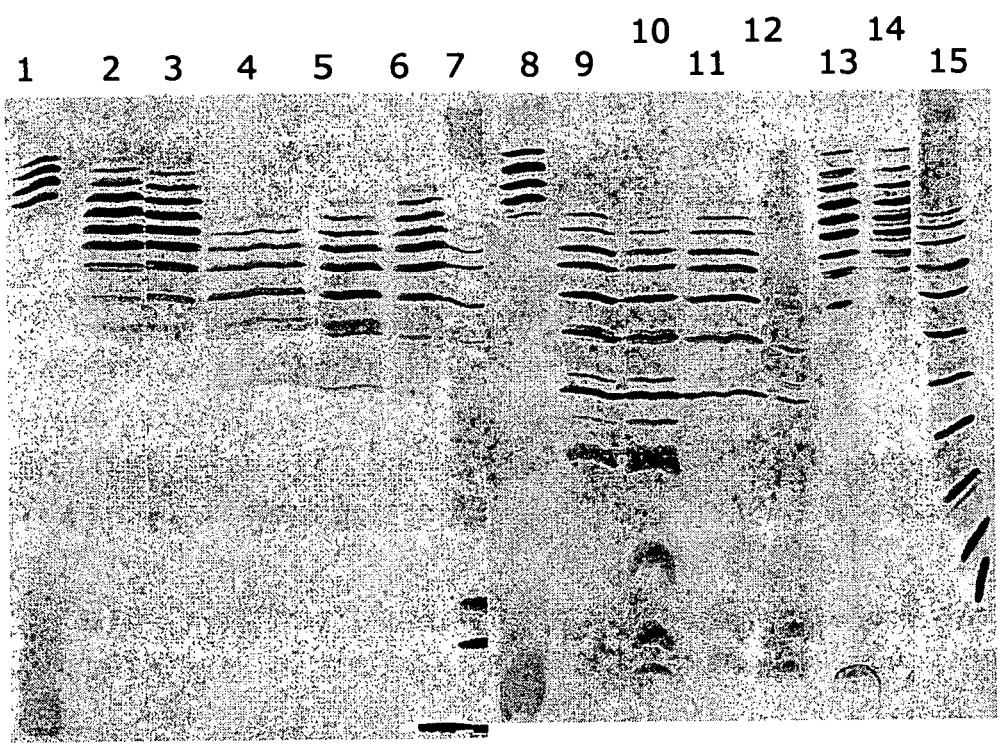
FIG. 18. IEF analysis of stable clones expressing EPO and human $\alpha$-2,3-sialyltransferase (ST3). Lane 1: EPREX (control, commercially available EPO), 2: EPO-ST3 clone 118, 3: EPO-ST3 clone 150, 4: EPO-ST3 clone 165, 5: EPO-ST3 clone 176, 6: EPO-ST3 clone 183, 7: EPO produced in PER.C6 without over-expressing ST3 (control), 8: EPREX (control, commercially available EPO), 9: EPO-ST3 clone 185, 10: EPO-ST3 clone 186, 11: EPO-ST3 clone 199, 12: EPO-ST3 clone 213, 13: EPO-ST3 clone 028, 14: EPO-ST3 clone 059, 15: EPO produced in PER.C6 without over-expressing ST3 (control). See Example 53 for details.
Figure 19:
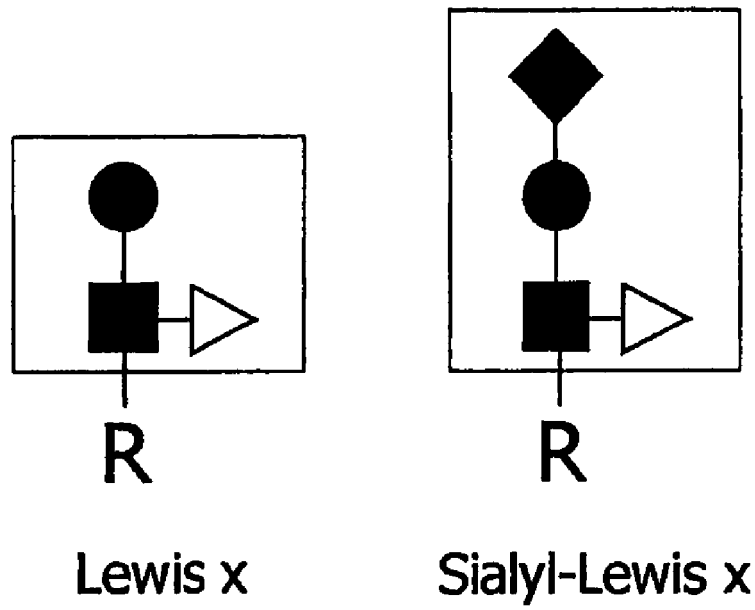
FIG. 19. Schematic representation of Lewis X and Sialyl Lewis X structures.

A number of cell lines described in Example 8 were used in an amplification experiment to determine the possibility of increasing the number of DHFR genes by increasing the concentration of MTX in a time span of more than two months. The concentration started at the threshold concentration (100 nM) and increased to 1800 nM with in-between steps of 200 nM, 400 nM, 800 nM and 1200 nM. During this period, EPO ELISA experiments were performed on a regular basis to detect the units per million seeded cells per day (FIG. 18 of the incorporated '544 patent). At the highest MTX concentration (1800 nM), some vials were frozen. Cell pellets were obtained and DNA was extracted and subsequently digested with BglII, since this enzyme cuts around the wild type DHFR gene in pEPO200/DHFRwt (FIG. 5 of the incorporated '007 application), so a distinct DHFR band of that size would be distinguishable from the endogenous DHFR bands in a Southern blot. This DNA was run and blotted and the blot was hybridized with a radioactive DHFR probe and subsequently with an adenovirus E1 probe as a background control (FIG. 19 of the incorporated '544 patent). The intensities of the hybridizing bands were measured in a phosphorimager and corrected for background levels. These results are shown in Table 3 of the incorporated '544 patent. Apparently, it is possible to obtain amplification of the DHFR gene in PER.C6 cells, albeit in this case only with the endogenous DHFR and not with the integrated vector.

Example 11

Stability of EPO Expression in Stable Cell Lines

A number of cell lines mentioned in Example 8 were subject to long term culturing in the presence and absence of MTX. EPO concentrations were measured regularly in which 1.0 to 1.5×10$^6$ cells per T25 flask were seeded and left for 4 days to calculate the production levels of EPO per million seeded cells per day. The results are shown in FIG. 20 of the incorporated '544 patent. From this, it is concluded that there is a relatively stable expression of EPO in P9 cells when cells are cultured in the presence of MTX and that there is a decrease in EPO production in the absence of MTX. However, when P9 cells were placed on 100 nM MTX again after being cultured for a longer period of time without MTX, the expressed EPO reached its original level (+/−3000 ELISA units per million seeded cells per day), suggesting that the integrated plasmids are shut off but are stably integrated and can be switched back on again. It seems as if there are differences between the cell lines P8 and P9 because the production level of P8 in the presence of MTX is decreasing in time over a high number of passages (FIG. 20A of the incorporated '544 patent), while P9 production is stable for at least 62 passages (FIG. 20B of the incorporated '544 patent).

Example 12

Transient Expression of Recombinant EPO on Attached and Suspension Cells After Plasmid DNA Transfections pEPO2000/DHFRwt, pEPO2000/DHFRm and pAdApt.EPO plasmids from Example 2 are purified from *E. coli* over columns, and are transfected using lipofectamine, electroporation, PEI or other methods. PER.C6 or PER.C6/E2A cells are counted and seeded in DMEM plus serum or JRH ExCell 525 medium or the appropriate medium for transfection in suspension. Transfection is performed at 37° C. up to 16 hours, depending on the transfection method used, according to procedures known by a person skilled in the art. Subsequently, the cells are placed at different temperatures and the medium is replaced by fresh medium with or without serum. In the case when it is necessary to obtain medium that completely lacks serum components, the fresh medium lacking serum is removed again after 3 hours and replaced again by medium lacking serum components. For determination of recombinant EPO production, samples are taken at different time points. Yields of recombinant protein are determined using an ELISA kit (R&D Systems) in which 1 Unit equals approximately 10 ng of recombinant CHO-produced EPO protein (100,000 Units/mg). The cells used in these experiments grow at different rates, due to their origin, characteristics and temperature. Therefore, the amount of recombinant EPO produced is generally calculated in ELISA units/10$^6$ seeded cells/day, taking into account that the antisera used in the ELISA kit do not discriminate between non- and highly glycosylated recombinant EPO. Generally, samples for these calculations are taken at day 4 after replacing the medium upon transfection.

PER.C6/E2A cells, transfected at 37° C. using lipofectamine and subsequently grown at 39° C. in the presence of serum, typically produced 3100 units/10$^6$ cells/day. In the absence of serum components without any refreshment of medium lacking serum, these lipofectamine-transfected cells typically produced 2600 units/10$^6$ cells/day. PER.C6 cells, transfected at 37° C. using lipofectamine and subsequently grown at 37° C. in the presence of serum, typically produced 750 units/10$^6$ cells/day and, in the absence of serum, 590 units/10$^6$ cells/day. For comparison, the same expression plasmids pEPO2000/DHFRwt and pEPO2000/DHFRm were also applied to transfect CHO cells (ECACC deposit no. 85050302) using lipofectamine, PEI, calcium phosphate procedures and other methods. When CHO cells were transfected using lipofectamine and subsequently cultured in Hams F12 medium in the presence of serum, a yield of 190 units/106 cells/day was obtained. In the absence of serum, 90 units/106 cells/day were produced, although higher yields can be obtained when transfections are being performed in DMEM.

Different plates containing attached PER.C6/E2A cells were also transfected at 37° C. with pEPO2000/DHFRwt plasmid and subsequently placed at 32° C., 34° C., 37° C. or 39° C. to determine the influence of temperature on recombinant EPO production. A temperature-dependent production level was observed ranging from 250 to 610 units/10$^6$ seeded cells/day, calculated from a day 4 sample, suggesting that the difference between production levels observed in PER.C6 and PER.C6/E2A is partly due to incubation temperatures (See, also FIG. 17 of the incorporated '544 patent). Since PER.C6/E2A grows well at 37° C., further studies were performed at 37° C.

Different plates containing attached PER.C6 and PER.C6/E2A cells were transfected with pEPO2000/DHFRwt, pEPO2000/DHFRm and pAdApt.EPO using lipofectamine. Four hours after transfection, the DMEM was replaced with either DMEM plus serum or JRH medium lacking serum and EPO was allowed to accumulate in the supernatant for several days to determine the concentrations that are produced in the different mediums. PER.C6 cells were incubated at 37° C., while PER.C6/E2A cells were kept at 39° C. Data from the different plasmids were averaged since they contain a similar expression cassette. Calculated from a day 6 sample, the following data were obtained: PER.C6 grown in DMEM produced 400 units/106 seeded cells/day, and when they were kept in JRH medium, they produced 300 units/106 seeded cells/day. PER.C6/E2A grown in DMEM produced 1800 units/106 seeded cells/day, and when they were kept in JRH, they produced 1100 units/106 seeded cells/day. Again, a clear difference was observed in production levels between PER.C6 and PER.C6/E2A, although this might partly be due to temperature differences. There was, however, a significant difference with PER.C6/E2A cells between the concentration in DMEM vs. the concentration in JRH medium, although this effect was almost completely lost in PER.C6 cells.

EPO expression data obtained in this system are summarized in Table 4 (of the incorporated '544 patent). PER.C6 and derivatives thereof can be used for scaling up the DNA transfections system. According to Wurm and Bernard (1999), transfections on suspension cells can be performed at 1-10 liter set-ups in which yields of 1-10 mg/l (0.1-1 pg/cell/day) of recombinant protein have been obtained using electroporation. A need exists for a system in which this can be well controlled and yields might be higher, especially for screening of large numbers of proteins and toxic proteins that cannot be produced in a stable setting. With the lipofectamine transfections on the best PER.C6 cells in the absence of serum, we reached 590 units/million cells/day (+/−5.9 pg/cell/day when 1 ELISA unit is approximately 10 ng EPO), while PER.C6/E2A reached 31 pg/cell/day (in the presence of serum). The medium used for suspension cultures of PER.C6 and PER.C6/E2A (JRH ExCell 525) does not support efficient transient DNA transfections using components like PEI. Therefore, the medium is adjusted to enable production of recombinant EPO after transfection of pEPO2000/DHFRwt and pEPO2000/DHFRm containing a recombinant human EPO cDNA, and pcDNA2000/DHFRwt containing other cDNA's encoding recombinant proteins.

1 to 10 liter suspension cultures of PER.C6 and PER.C6/E2A growing in adjusted medium to support transient DNA transfections using purified plasmid DNA are used for electroporation or other methods, performing transfection with the same expression plasmids. After several hours, the transfection medium is removed and replaced by fresh medium without serum. The recombinant protein is allowed to accumulate in the supernatant for several days, after which the supernatant is harvested and all the cells are removed. The supernatant is used for down stream processing to purify the recombinant protein.

Example 13

Generation of AdApt.EPO Recombinant Adenoviruses

AdApt.EPO was co-transfected with the pWE/Ad.AflII-rITR.tetO-E4, pWE/Ad.AflII-rITR.DE2A, and pWE/Ad.AflII-rITR.DE2A.tetO-E4 cosmids in the appropriate cell lines using procedures known to persons skilled in the art. Subsequently, cells were left at their appropriate temperatures for several days until full cytopathic effect ("CPE") was observed. Then cells were applied to several freeze/thaw steps to free all viruses from the cells, after which the cell debris was spun down. For IG.Ad5/AdApt.EPO.dE2A, the supernatant was used to infect cells, followed by an agarose overlay for plaque purification using several dilutions. After a number of days, when single plaques were clearly visible in the highest dilutions, nine plaques and one negative control (picked cells between clear plaques, so most likely not containing virus) were picked and checked for EPO production on A549 cells. All plaque picked viruses were positive and the negative control did not produce recombinant EPO. One positive producer was used to infect the appropriate cells and to propagate virus starting from a T-25 flask to a roller bottle setting. Supernatants from the roller bottles were used to purify the virus, after which the number of virus particles (vp's) was determined and compared to the number of infectious units (IU's) using procedures known to persons skilled in the art. Then, the vp/IU ratio was determined.

Example 14

Infection of Attached and Suspension PER.C6 Cells with IG.Ad5/AdApt.EPO.dE2A

Purified viruses from Example 13 were used for transient expression of recombinant EPO in PER.C6 cells and derivatives thereof. IG.Ad5/AdApt.EPO.dE2A virus was used to infect PER.C6 cells, while IG.Ad5/AdApt.EPO.tetOE4 and IG.Ad5/AdApt.EPO.dE2A.tetOE4 viruses can be used to infect PER.C6/E2A cells to lower the possibility of replication and, moreover, to prevent inhibition of recombinant protein production due to replication processes. Infections were performed on attached cells as well as on suspension cells in their appropriate medium using ranges of multiplicities of infection (moi's): 20, 200, 2000, 20000 vp/cell. Infections were performed for 4 hours in different settings ranging from 6-well plates to roller bottles, after which the virus containing supernatant was removed. The cells were washed with PBS or directly refreshed with new medium. Then, cells were allowed to produce recombinant EPO for several days, during which samples were taken and EPO yields were determined. Also, the number of viable cells compared to dead cells was checked. The amount of EPO that was produced was again calculated as ELISA unit seeded cells/day, because the different cell lines have different growth characteristics due to their passage number and environmental circumstances such as temperature and selective pressures. Suspension growing PER.C6 cells were seeded in 250 ml JRH ExCell 525 medium in roller bottles (1 million cells per ml) and subsequently infected with purified IG.Ad5/AdApt.EPO.dE2A virus with an moi of 200 vp/cell. The estimation used for vp determination was high (vp/tU ratio of this batch is 330, which indicates an moi of 0.61 IU's/cell). Thus, not all cells were hit by an infectious virus. A typical production of recombinant EPO in this setting from a day 6 sample was 190 units/106 seeded cells/day, while in a setting in which 50% of the medium including viable and dead cells was replaced by fresh medium, approximately 240 units/$10^6$ cells/day were obtained. The refreshment did not influence the viability of the viable cells, but the removed recombinant protein could be added to the amount that was obtained at the end of the experiment, albeit present in a larger volume. An identical experiment was performed with the exception that cells were infected with an moi of 20 vp/cell, resembling approximately 0.06 Infectious Units/cell. Without refreshment, a yield of 70 ELISA units/$10^6$ cells/day was obtained, while in the experiment in which 50% of the medium was refreshed at day 3, a typical amount of 80 units/106 cells/day was measured. This indicates that there is a dose response effect when an increasing number of infectious units are used for infection of PER.C6 cells.

Furthermore, PER.C6 cells growing in DMEM were seeded in 6-well plates and left overnight in 2 ml DMEM with serum to attach. The next day, cells were infected with another batch of IG.Ad5/AdApt.EPO.dE2A virus (vp/IU ratio 560) with an moi of 200 vp/cells (0.35 Infectious Units/cell). After 4 hours, the virus containing medium was removed and replaced by fresh medium including serum, and cells were left to produce recombinant EPO for more than two weeks with replacement of the medium with fresh medium every day. The yield of recombinant EPO production calculated from a day 4 sample was 60 units/106 cells/day.

Expression data obtained in this system have been summarized in Table 5 (of the incorporated '544 patent).

Due to the fact that a tTA-tetO regulated expression of the Early region 4 of adenovirus (E4) impairs the replication capacity of the recombinant virus in the absence of active E4, it is also possible to use the possible protein production potential of the PER.C6/E2A as well as its parental cell line PER.C6 to produce recombinant proteins in a setting in which a recombinant adenovirus is carrying the human EPO cDNA as the transgene and in which the E4 gene is under the control of a tet operon. Then, very low levels of E4 mRNA are being produced, resulting in very low but detectable levels of recombinant and replicating virus in the cell line PER.C6/E2A and no detectable levels of this virus in PER.C6 cells. To produce recombinant EPO in this way, the two viruses IG.Ad5/AdApt.EPO.tetOE4 and IG.Ad5/AdApt.EPO.dE2A.tetOE4 are used to infect PER.C6 cells and derivatives thereof. Attached and suspension cells are infected with different moi's of the purified adenoviruses in small settings (6-well plates and T25 flasks) and large settings (roller bottles and fermentors). Samples are taken at different time points and EPO levels are determined.

Since viruses that are deleted in E1 and E2A in the viral backbone can be complemented in PER.C6/E2A cells but not in the original PER.C6 cells, settings are used in which a mixture of both cell lines is cultured in the presence of IG.Ad5/AdApt.EPO.dE2A virus. The virus will replicate in PER.C6/E2A, followed by lysis of the infected cells and a subsequent infection of PER.C6 or PER.C6/E2A cells. In contrast, in PER.C6 cells, the virus will not replicate and the cells will not lyse due to viral particle production, but will produce recombinant EPO that will be secreted in the supernatant. A steady state culture/replication/EPO production system is set up in which fresh medium and fresh PER.C6 and PER.C6/E2A cells are added at a constant flow, while used medium, dead cells and debris are removed. Together with this, recombinant EPO is taken from the system and used for purification in a down stream processing procedure in which virus particles are removed.

Example 15

Purification and Analysis of Recombinant EPO

Large batches of growing cells are produced in bioreactors; the secreted recombinant human EPO protein is purified according to procedures known by one of skill in the art. The purified recombinant human EPO protein from PER.C6 and PER.C6/E2A stable clones or transfectants is checked for glycosylation and folding by comparison with commercially available EPO and EPO purified from human origin (urine) using methods known to one of skill in the art (See, Examples 16 and 17). Purified and glycosylated EPO proteins from PER.C6 and PER.C6/E2A are tested for biological activity in in vitro experiments and in mouse spleens as described (Krystal (1983) and in vitro assays (See, Example18).

Example 16

Activity of Beta-Galactoside Alpha 2,6-sialyltransferase in PER.C6

It is known that CHO cells do not contain a gene for beta-galactoside alpha 2,6-sialyltransferase, resulting in the absence of alpha 2,6-linked sialic acids at the terminal ends of—and O-linked oligosaccharides of endogenous and recombinant glycoproteins produced on these CHO cells. Since the alpha 2,3-sialyltransferase gene is present in CHO cells, proteins that are produced on these cells are typically from the 2,3 linkage type. EPO that was purified from human urine does, however, contain both alpha 2,3- and alpha 2,6-linked sialic acids. To determine whether PER.C6 cells, being a human cell line, are able to produce recombinant EPO containing both alpha 2,3- and alpha 2,6-linkages, a direct neuraminidase assay was performed on recombinant EPO produced on PER.C6 cells after transfection with EPO expression vectors. As a control, commercially available EPREX samples were used, which were derived from CHO cells and which should only contain sialic acid linkages of the alpha 2,3 type. The neuraminidases that were used were from Newcastle Disease Virus (NDV) that specifically cleaves alpha 2,3-linked neuraminic acids (sialic acids) from—and O-linked glycans, and from Vibrocholerae (VC) that non-specifically cleaves all terminal—or O-linked sialic acids (alpha 2,3, alpha 2,6 and alpha 2,8 linkages). Both neuraminidases were from Boehringer and were incubated with the samples according to guidelines provided by the manufacturer. Results are shown in FIG. 21A (of the incorporated '544 patent). In lanes 2 and 3 (treatment with NDV neuraminidase), a slight shift is observed as compared to lane 1 (non-treated PER.C6 EPO). When this EPO sample was incubated with VC derived neuraminidase, an even faster migrating band is observed as compared to NDV treated samples. However, with the commercially available EPREX, only a shift was observed when NDV derived neuraminidase was applied (lanes 6 and 7 compared to the non-treated sample in lane 5) and not when VC neuraminidase was used (lane 8).

To definitely establish that no sialic acids of the alpha 2,6 linkage type are present on CHO cells, but that they do exist in proteins present on the cell surface of PER.C6 cells, the following experiment was performed: CHO cells were released from the solid support using trypsin-EDTA, while for PER.C6, suspension cells were used. Both suspensions were washed once with Mem-5% FBS and incubated in this medium for 1 h at 37° C. After washing with PBS, the cells were resuspended to approximately $10^6$ cells/ml in binding medium (Tris-buffered saline, pH 7.5, 0.5% BSA, and 1 mM each of $MgCl_2$, $MnCl_2$ and $CaCl_2$). Aliquots of the cells were incubated for 1 h at room temperature with DIG-labeled lectins, Sambucus nigra agglutinin ("SNA") and Maackia amurensis agglutinin ("MAA"), which specifically bind to sialic acid linkages of the alpha 2,6 Gal and alpha 2,3 Gal types, respectively. Control cells were incubated without lectins. After 1 hour, both lectin-treated and control cells were washed with PBS and then incubated for 1 hour at room temperature with FITC-labeled anti-DIG antibody (Boehringer-Mannheim). Subsequently, the cells were washed with PBS and analyzed for fluorescence intensity on a FACsort apparatus (Becton Dickinson). The FACS analysis is shown in FIG. 21B (of the incorporated '544 patent). When the SNA lectin is incubated with CHO cells, no shift is seen as compared to non-treated cells, while when this lectin is incubated with PER.C6 cells, a clear shift (dark fields) is observed as compared to non-treated cells (open fields). When both cell lines are incubated with the MAA lectin, both cell lines give a clear shift as compared to non-treated cells.

From these EPO digestions and FACS results, it is concluded that there is a beta-galactoside alpha 2,6 sialyltransferase activity present in human PER.C6 cells which is absent in CHO cells.

Example 17

Determination of Sialic Acid Content in PER.C6 Produced EPO

The terminal neuraminic acids (or sialic acids) that are present on the—and O-linked glycans of EPO protect the protein from clearance from the bloodstream by enzymes in the liver. Moreover, since these sialic acids are negatively charged, one can distinguish between different EPO forms depending on their charge or specific pI. therefore, EPO produced on PER.C6 and CHO cells was used in 2-dimensional electrophoresis in which the first dimension separates the protein on charge (pH range 3-10) and the second dimension separates the proteins further on molecular weight. Subsequently, the proteins were blotted and detected in a western blot with an anti-EPO antibody.

It is also possible to detect the separated EPO protein by staining the gel using Coomassie blue or silver staining methods, subsequently removing different spots from the gel and determining the specific glycan composition of the different—or O-linked glycosylations that are present on the protein by mass spectrometry.

In FIG. 22A of the incorporated '544 patent, a number of EPO samples are shown that were derived from P9 supernatants. P9 is the PER.C6 cell line that stably expresses recombinant human EPO (See, Example 8). These samples were compared to commercially available EPREX, which contains only EPO forms harboring approximately 9 to 14 sialic acids. EPREX should, therefore, be negatively charged and be focusing towards the pH 3 side of the gel. FIG. 22B (of the incorporated '544 patent) shows a comparison between EPO derived from P9 in an attached setting in which the cells were cultured on DMEM medium and EPO derived from CHO cells that were transiently transfected with the pEPO2000/DHFRwt vector. Apparently, the lower forms of EPO cannot be detected in the CHO samples, whereas all forms can be seen in the P9 sample. The sialic acid content is given by numbering the bands that were separated in the first dimension from 1 to 14. It is not possible to determine the percentage of each form of EPO molecules present in the mixtures because the western blot was performed using ECL, and because it is unknown whether glycosylation of the EPO molecule or transfer of the EPO molecule to the nitrocellulose inhibits recognition of the EPO molecule by the antibody. However, it is possible to determine the presence of the separate forms of sialic acid containing EPO molecules. It can be concluded that PER.C6 is able to produce the entire range of 14 sialic acid containing isoforms of recombinant human EPO.

Example 18

In Vitro Functionality of PER.C6 Produced EPO

The function of recombinant EPO in vivo is determined by its half-life in the bloodstream. Removal of EPO takes place by liver enzymes that bind to galactose residues in the glycans that are not protected by sialic acids and by removal through the kidney. Whether this filtering by the kidney is due to misfolding or due to under- or mis-glycosylation is unknown. Furthermore, EPO molecules that reach their targets in the bone marrow and bind to the EPO receptor on progenitor cells are also removed from circulation. Binding to the EPO receptor and down stream signaling depends heavily on a proper glycosylation status of the EPO molecule. Sialic acids can, to some extent, inhibit binding of EPO to the EPO receptor, resulting in a lower effectiveness of the protein. However, since the sialic acids prevent EPO from removal, these sugars are essential for its function to protect the protein on its travel to the EPO receptor. When sialic acids are removed from EPO in vitro, a better binding to the receptor occurs, resulting in a stronger down stream signaling. This means that the functionalities in vivo and in vitro are significantly different, although a proper EPO receptor binding property can be checked in vitro despite the possibility of an under-sialylation causing a short half-life in vivo (Takeuchi et al. 1989).

Several in vitro assays for EPO functionality have been described of which the stimulation of the IL3, GM-CSF and EPO-dependent human cell line TF-1 is most commonly used. Hereby, one can determine the number of in vitro units per mg (Kitamura et al. 1989; Hammerling et al. 1996). Other in vitro assays are the formation of red colonies under an agarose layer of bone marrow cells that were stimulated to differentiate by EPO, the incorporation of 59Fe into heme in cultured mouse bone marrow cells (Krystal et al. 1981 and 1983; Takeuchi et al. 1989), in rat bone marrow cells (Goldwasser et al. 1975) and the Radio Immuno Assay (RIA) in which the recognition of EPO for antisera is determined.

EPO produced on PER.C6/E2A cells was used to stimulate TF-1 cells as follows: Cells were seeded in 96-well plates with a density of around 10,000 cells per well in medium lacking IL3 or GM-CSF, which are the growth factors that can stimulate indefinite growth of these cells in culture. Subsequently, medium is added, resulting in final concentrations of 0.0001, 0.001, 0.01, 0.1, 1 and 10 units per ml. These units were determined by ELISA, while the units of the positive control EPREX were known (4000 units per ml) and were diluted to the same concentration. Cells were incubated with these EPO samples for 4 days, after which an MTS assay (Promega) was performed to check for viable cells by fluorescence measurement at 490 nm (fluorescence is detectable after transfer of MTS into formazan). FIG. 23 of the incorporated '544 patent shows the activity of two samples derived from PER.C6/E2A cells that were transfected with an EPO expression vector and subsequently incubated at 37° C. and 39° C. for 4 days. The results suggest that samples obtained at 39° C. are more active than samples obtained at 37° C., which might indicate that the sialic acid content is suboptimal at higher temperatures. It is hereby shown that PER.C6 produced EPO can stimulate TF-1 cells in an in vitro assay, strongly suggesting that the EPO that is produced on this human cell line can interact with the EPO receptor and stimulate differentiation.

Example 19

Production of Recombinant Murine, Humanized and Human Monoclonal Antibodies in PER.C6 and PER.C6/E2A A. Transient DNA Transfections cDNA's encoding heavy and light chains of murine, humanized and human monoclonal antibodies (mAbs) are cloned in two different systems: one in which the heavy and light chains are integrated into one single plasmid (a modified pcDNA2000/DHFRwt plasmid) and the other in which heavy and light chain cDNA's are cloned separately into two different plasmids (See, Examples 1, 3, 4 and 5). These plasmids can carry the same selection marker (like DHFR) or they carry their own selection marker (one that contains the DHFR gene and one that contains, for instance, the neo-resistance marker). For transient expression systems, it does not matter what selection markers are present in the backbone of the vector since no subsequent selection is being performed. In the common and regular transfection methods used in the art, equal amounts of plasmids are transfected. A disadvantage of integrating both heavy and light chains on one single plasmid is that the promoters that are driving the expression of both cDNA's might influence each other, resulting in non-equal expression levels of both subunits, although the number of cDNA copies of each gene is exactly the same.

Plasmids containing the cDNA's of the heavy and light chain of a murine and a humanized monoclonal antibody are transfected and, after several days, the concentration of correctly folded antibody is determined using methods known to persons skilled in the art. Conditions such as temperature and used medium are checked for both PER.C6 and PER.C6/E2A cells. Functionality of the produced recombinant antibody is controlled by determination of affinity for the specified antigen.

B. Transient Viral Infections cDNA's encoding a heavy and a light chain are cloned in two different systems: one in which the heavy and light chains are integrated into one single adapter plasmid (a modified pAdApt.pac) and the other in which heavy and light chain cDNA's are cloned separately into two different adapters (each separately in pAdApt.pac). In the first system, viruses are propagated that carry an E1 deletion (dE1) together with a E2A deletion (dE2A) or both deletions in the context of a tetOE4 insertion in the adenoviral backbone. In the second system, the heavy and light chains are cloned separately in pAdApt.pac and separately propagated to viruses with the same adenoviral backbone. These viruses are used to perform single or co-infections on attached and suspension growing PER.C6 and PER.C6/E2A cells. After several days, samples are taken to determine the concentration of full length recombinant antibodies, after which the functionality of these antibodies is determined using the specified antigen in affinity studies.

C. Stable Production and Amplification of the Integrated Plasmid.

Expression plasmids carrying the heavy and light chain together and plasmids carrying the heavy and light chain separately are used to transfect attached PER.C6 and PER.C6/E2A and CHO-dhfr cells. Subsequently, cells are exposed to MTX and/or hygromycin and neomycin to select for integration of the different plasmids. Moreover, a double selection with G418 and hygromycin is performed to select for integration of plasmids that carry the neomycin and hygromycin resistance gene. Expression of functional full length monoclonal antibodies is determined and best expressing clones are used for subsequent studies including stability of integration, copy number detection, determination of levels of both subunits and ability to amplify upon increase of MTX concentration after the best performing cell lines are used for mAb production in larger settings such as perfused and (fed-) batch bioreactors, after which optimization of quantity and quality of the mAbs is executed.

Example 20

Transfection of mAb Expression Vectors to Obtain Stable Cell Lines

PER.C6 cells were seeded in DMEM plus 10% FBS in 47 tissue culture dishes (10 cm diameter) with approximately 2.5×106 cells per dish and were kept overnight under their normal culture conditions (10% $CO_2$ concentration and 37° C.). The next day, co-transfections were performed in 39 dishes at 37° C. using Lipofectamine in standard protocols with 1 µg MunI digested and purified pUBS-Heavy2000/Hyg(−) and 1 µg Seal digested and purified pUBS-Light2001/Neo (See, Example 3) per dish, while 2 dishes were co-transfected as controls with 1 µg MunI digested and purified pcDNA2000/Hyg(−) and 1 µg Seal digested and purified pcDNA2001/Neo. As a control for transfection efficiency, 4 dishes were transfected with a LacZ control vector, while 2 dishes were not transfected and served as negative controls.

After hours, cells were washed twice with DMEM and re-fed with fresh medium without selection. The next day, medium was replaced by fresh medium containing different selection reagents: 33 dishes of the heavy and light chain co-transfectants, 2 dishes that were transfected with the empty vectors and the 2 negative controls (no transfection) were incubated only with 50 µg per ml hygromycin, 2 dishes of the heavy and light chain co-transfectants and 2 dishes of the transfection efficiency dishes (LacZ vector) were incubated only with 500 µg per ml G418, while 2 transfection efficiency dishes were not treated with selection medium but used for transfection efficiency that was around 40%. Two dishes were incubated with a combination of 50 µg per ml hygromycin and 250 µg per ml G418 and 2 dishes were incubated with 25 µg per ml hygromycin and 500 µg per ml G418.

Since cells were overgrowing when they were only incubated with hygromycin alone, it was decided that a combination of hygromycin and G418 selection would immediately kill the cells that integrated only one type of the two vectors that were transfected. Seven days after seeding, all co-transfectants were further incubated with a combination of 100 ug per ml hygromycin and 500 µg per ml G418. Cells were refreshed 2 or 3 days with medium containing the same concentrations of selecting agents. Fourteen days after seeding, the concentrations were adjusted to 250 µg per ml G418 and 50 µg per ml hygromycin. Twenty-two days after seeding, a large number of colonies had grown to an extent in which it was possible to select, pick and subculture. Approximately 300 separate colonies were selected and picked from the 10 cm dishes and subsequently grown via 96-wells and/or 24-wells via 6-well plates to T25 flasks. In this stage, cells are frozen (4 vials per subcultured colony) and production levels of recombinant UBS-54 mAb are determined in the supernatant using the ELISA described in Example 26.

CHO-dhfr cells are seeded in DMEM plus 10% FBS including hypoxanthine and thymidine in tissue culture dishes (10 cm diameter) with approximately 1 million cells per dish and are kept overnight under normal conditions and used for a co-transfection the next day with pUBS-Heavy2000/Hyg(−) and pUBS-Light2001/DHFRwt under standard protocols using Lipofectamine. Medium is replaced with fresh medium after a few hours and split to different densities to allow the cells to adjust to the selection medium when stable integration is taking place without a possible outgrowth of non-transfected cells. Colonies are first selected on hygromycin resistance and, subsequently, MTX is added to select for double integrations of the 2 plasmids in these subcultured cell lines.

Transfections as described for pUBS-Heavy2000/Hyg(−) and pUBS-Light2001/Neo are performed with pUBS2-Heavy2000/Hyg(−) and pUBS2-Light2001/Neo in PER.C6 and PER.C6/E2A and selection is performed with either subsequent incubation with hygromycin followed by G418 or as described above with a combination of both selection reagents. CHO-dhfr cells are transfected with pUBS2-Heavy2000/Hyg(−) and pUBS2-Light2001/DHFRwt as described herein and selection is performed in a sequential way in which cells are first selected with hygromycin, after which an integration of the light chain vector is controlled by selection on MTX.

Furthermore, PER.C6 and PER.C6/E2A cells are also used for transfections with pUBS-3000/Hyg(−) and pUBS2-3000/Hyg(−), while CHO-dhfr cells are transfected with pUBS-3000/DHFRwt and pUBS2-3000/DHFRwt, after which a selection and further amplification of the integrated plasmids are performed by increasing the MTX concentration. In the case of the pcDNAs3000 plasmids, an equal number of mRNA's of both the heavy and light chain is expected, while in the case of two separate vectors, it is unclear whether a correct equilibrium is achieved between the two subunits of the immunoglobulin.

Transfections are also being performed on PER.C6, PER.C6/E2A and CHO-dhfr with expression vectors described in Examples 4 and 5 to obtain stable cell lines that express the humanized IgG1 mAb CAMPATH-1H and the humanized IgG1 mAb 15C5 respectively.

Example 21

Sub-Culturing of Transfected Cells

From PER.C6 cells transfected with pUBS-Heavy2000/Hyg (−) and PUBS-Light2001/Neo, approximately 300 colonies that were growing in medium containing Hygromycin and G418 were generally grown subsequently in 96-well, 24-well and 6-well plates in their respective medium plus their respective selecting agents. Cells that were able to grow in 24 well plates were checked for mAb production by using the ELISA described in Example 26. If cells scored positively, at least one vial of each clone was frozen and stored, and cells were subsequently tested and subcultured. The selection of a good producer clone is based on high expression, culturing behavior and viability. To allow checks for long term viability, amplification of the integrated plasmids and suspension growth during extended time periods, best producer clones are frozen, of which a number of the best producers of each cell line are selected for further work. Similar experiments are being performed on CHO-dhfr cells transfected with different plasmids and PER.C6 and PER.C6/E2A cells that were transfected with other combinations of heavy and light chains and other combinations of selection markers.

Example 22 mAb Production in Bioreactors

The best UBS-54 producing transfected cell line of PER.C6 is brought into suspension by washing the cells in PBS and then culturing the cells in JRH ExCell 525 medium, first in small culture flasks and subsequently in roller bottles, and scaled up to 1 to 2 liter fermentors. Cells are kept on hygromycin and G418 selection until it is proven that integration of the vectors is stable over longer periods of time. This is done when cells are still in their attached phase or when cells are in suspension.

Suspension growing mAb producing PER.C6 cells are generally cultured with hygromycin and G418 and used for inoculation of bioreactors from roller bottles. Production yields, functionality and quality of the produced mAb is checked after growth of the cells in perfused bioreactors and in fed batch settings.

A. Perfusion in a 2 liter Bioreactor.

Cells are seeded in suspension medium in the absence of selecting agents at a concentration of approximately $0.5 \times 10^6$ cells per ml and perfusion is started after a number of days when cell density reaches approximately 2 to $3 \times 10^6$ cells per ml. The perfusion rate is generally 1 volume per 24 hours with a bleed of approximately 250 ml per 24 hours. In this setting, cells stay normally at a constant density of approximately $5 \times 10^6$ cells per ml and a viability of almost 95% for over a month. The mAb production levels are determined on a regular basis.

B. Fed Batch in a 2 Liter Bioreactor.

In an initial run, mAb producing PER.C6 suspension cells that are grown on roller bottles are used to inoculate a 2 liter bioreactor in the absence of selecting agents to a density of 0.3 to 0.5 million cells per ml in a working volume of 300 to 500 ml and are left to grow until the viability of the cell culture drops to 10%. As a culture lifetime standard, it is determined at what day after inoculation the viable cell density drops beneath 0.5 million cells per ml. Cells normally grow until a density of 2 to 3 million cells per ml, after which the medium components become limiting and the viability decreases. Furthermore, it is determined how much of the essential components, such as glucose and amino acids in the medium are being consumed by the cells. Next to that, it is determined what amino acids are being produced and what other products are accumulating in the culture. Depending on this, concentrated feeding samples are being produced that are added at regular time points to increase the culture lifetime and thereby increase the concentration of the mAb in the supernatant. In another setting, 10× concentrated medium samples are developed that are added to the cells at different time points and that also increase the viability of the cells for a longer period of time, finally resulting in a higher concentration of mAb in the supernatant.

Example 23

Transient Expression of Humanized Recombinant Monoclonal Antibodies

The correct combinations of the UBS-54 heavy and light chain genes containing vectors were used in transient transfection experiments in PER.C6 cells. For this, it is not important which selection marker is introduced in the plasmid backbone, because the expression lasts for a short period (2-3 days). The transfection method is generally lipofectamine, although other cationic lipid compounds for efficient transfection can be used. Transient methods are extrapolated from T25 flasks settings to at least 10-liter bioreactors. Approximately 3.5 million PER.C6 and PER.C6/E2A cells were seeded at day 1 in a T25 flask. At day 2, cells were transfected with, at most, 8 ug plasmid DNA using lipofectamine and refreshed after 2-4 hours and left for 2 days. Then, the supernatant was harvested and antibody titers were measured in a quantitative ELISA for human IgG1 immunoglobulin (CLB, see also Example 26). Levels of total human antibody in this system are approximately 4.8 ug/million seeded cells for PER.C6 and 11.1 µg/million seeded cells for PER.C6/E2A. To determine how much of the produced antibody is of full size and built up from two heavy and two light chains, as well as the expression levels of the heavy and/or light chain alone and connected by disulfide bridges, control ELISA's recognizing the sub-units separately are developed. Different capturing and staining antibody combinations are used that all detect human(ized) IgG1 sub-units. Supernatants of PER.C6 transfectants (transfected with control vectors or pUBS-Heavy2000/Hyg(−) and pUBS-Light2001/DHFRwt) were checked for full sized mAb production (FIG. 24) (of the incorporated '544 patent). Samples were treated with and without DTT, wherein one can distinguish between full sized mAb (non-reduced) and heavy and light chain separately (reduced). As expected, the heavy chain is only secreted when the light chain is co-expressed and most of the antibody is of full size.

Example 24

Scale-Up System for Transient Transfections

PER.C6 and derivatives thereof are used for scaling up the DNA transfections system. According to Wurm and Bernard (1999), transfections on suspension cells can be performed at 1-10 liter set-ups in which yields of 1-10 mg/l (0.1-1 pg/cell/day) of recombinant protein have been obtained using electroporation.

A need exists for a system in which this can be well controlled and yields might be higher, especially for screening of large numbers of proteins and toxic proteins that cannot be produced in a stable setting. Moreover, since cell lines such as CHO are heavily affected by apoptosis-inducing agents such as lipofectamine, the art teaches that there is a need for cells that are resistant to this. Since PER.C6 is hardly affected by transfection methods, it seems that PER.C6 and derivatives thereof are useful for these purposes. One to 50 liter suspension cultures of PER.C6 and PER.C6/E2A growing in adjusted medium to support transient DNA transfections using purified plasmid DNA are used for electroporation or other methods, performing transfection with the same expression plasmids. After several hours, the transfection medium is removed and replaced by fresh medium without serum. The recombinant protein is allowed to accumulate in the supernatant for several days, after which the supernatant is harvested and all the cells are removed. The supernatant is used for down stream processing to purify the recombinant protein.

Example 25

Scale Up System for Viral Infections

Heavy and light chain cDNA's of the antibodies described in Examples 3, 4 and 5 are cloned into recombinant adenoviral adapter plasmids separately and in combination. The combinations are made to ensure an equal expression level for both heavy and light chains of the antibody to be formed. When heavy and light chains are cloned separately, viruses are being produced and propagated separately, of which the infectability and the concentration of virus particles are determined and finally co-infected into PER.C6 and derivatives thereof to produce recombinant mAbs in the supernatant. Production of adapter vectors, recombinant adenoviruses and mAbs is as described for recombinant EPO (See, Examples 13 and 14).

Example 26

Development of an ELISA for Determination of Human mAbs

Greiner microlon plates # 655061 were coated with an anti-human IgG1 kappa monoclonal antibody (Pharmingen #M032196 0.5) with 100 gl per well in a concentration of 4 µg per ml in PBS. Incubation was performed overnight at 4° C. or for 90 minutes at 37° C. Then, wells were washed three times with 0.05% TWEEN/PBS (400 µl per well) and subsequently blocked with 100 µl 5% milk dissolved in 0.05% TWEEN/PBS per well for 30 minutes at 37° C. and then, the plate was washed three times with 400 µl 0.05% TWEEN/PBS per well. As a standard, a purified human IgG1 antibody was used (Sigma, #108H9265) diluted in 0.5% milk/0.05% TWEEN/PBS in dilutions ranging from 50 to 400 ng per ml. Per well, 100 µl of the standard was incubated for 1 h at 37° C. Then, the plate was washed three times with 400 µl per well 0.05% TWEEN/PBS. As the second antibody, a biotin labeled mouse monoclonal anti-human IgG1 antibody was used (Pharmingen #M045741) in a concentration of 2 ng per ml. Per well, 100 µl of this antibody was added and incubated for 1 h at 37° C. and the wells were washed three times with 400 µl 0.05% TWEEN/PBS.

Subsequently, conjugate was added: 100 µl per well of a 1:1000 dilution of Streptavidin-HRP solution (Pharmingen #M045975) and incubated for 1 h at 37° C., and the plate was again washed three times with 400 µl per well with 0.05% TWEEN/PBS.

One ABTS tablet (Boehringer Mannheim #600191-01) was dissolved in 50 ml ABTS buffer (Boehringer Mannheim #60328501) and 100 µl of this solution was added to each well and incubated for 1 h at RT or 37° C. Finally, the OD was measured at 405 nm. Supernatant samples from cells transfected with mAb encoding vectors were generally dissolved and diluted in 0.5% milk/0.05% TWEEN/PBS. If samples did not fit with the linear range of the standard curve, other dilutions were used.

Example 27

Production of Influenza HA and NA Proteins in a Human Cell for Recombinant Subunit Vaccines cDNA sequences of genes encoding hemagluttinin (HA) and neuraminidase (NA) proteins of known and regularly appearing novel influenza virus strains are being determined and generated by PCR with primers for convenient cloning into pcDNA2000, pcDNA2001, pcDNA2002 and pcDNAs3000 vectors (See, Example 1). Subsequently, these resulting expression vectors are being transfected into PER.C6 and derivatives thereof for stable and transient expression of the recombinant proteins to result in the production of recombinant HA and NA proteins that are therefore produced in a complete standardized way with human cells under strict and well-defined conditions. Cells are allowed to accumulate these recombinant HA and NA proteins for a standard period of time. When the pcDNAs3000 vector is used, it is possible to clone both cDNA's simultaneously and have the cells produce both proteins at the same time. From separate or combined cultures, the proteins are being purified following standard techniques and final HA and NA titers are being determined and activities of the proteins are checked by persons skilled in the art. Then, the purified recombinant proteins are used for vaccination studies and finally used for large-scale vaccination purposes.

The HA1 fragment of the swine influenza virus A/swine/Oedenrode/7C/96 (Genbank accession number AF092053) was obtained by PCR using a forward primer with the following sequence: 5' ATT GGC GCG CCA CCA TGA AGA CTA TCA TTG CTT TGA GCT AC3' (SEQ ID NO: 30) corresponding to the incorporated '544 patent, and with a reverse primer with the following sequence: 5' GAT GCT AGC TCA TCT AGT TTG TTT TTC TGG TAT ATT CCG 3' (SEQ ID NO: 31) corresponding to the incorporated '544 patent. The resulting 1.0 kb PCR product was digested with AscI and NheI restriction enzymes and ligated with a AscI and NheI digested and purified pcDNA2000/DHFRwt vector, resulting in pcDNA2001/DHFRwt-swHA1. Moreover, the HA2 fragment of the same virus was amplified by PCR using the same forward primer as described for HA1 and another reverse primer with the following sequence: 5' GAT GCT AGC TCA GTC TTT GTA TCC TGA CTT CAG TTC AAC ACC 3' (SEQ ID NO: 32) corresponding to the incorporated '544 patent. The resulting 1.6 kb HA2 PCR product was cloned in an identical way as described for HA1, resulting in pcDNA2001/DHFRwt-swHA2.

Example 28

Integration of cDNA's Encoding Post-Translational Modifying Enzymes

Since the levels of recombinant protein production in stable and transiently transfected and infected PER.C6 and PER.C6/E2A are extremely high and since a higher expression level is usually obtained upon DHFR dependent amplification due to increase of MTX concentration, an "out-titration" of the endogenous levels of enzymes that are involved in post-translational modifications might occur.

Therefore, cDNA's encoding human enzymes involved in different kinds of post-translational modifications and processes such as glycosylation, phosphorylation, carboxylation, folding and trafficking are being overexpressed in PER.C6 and PER.C6/E2A to enable a more functional recombinant product to be produced to extreme levels in small and large settings. It was shown that CHO cells can be engineered in which an alpha-2,6-sialyltransferase was introduced to enhance the expression and bioactivity of tPA and human erythropoietin (Zhang et al. 1998, Minch et al. 1995, Jenkins et al. 1998). Other genes such as beta 1,4-galactosyltransferase were also introduced into insect and CHO cells to improve the N-linked oligosaccharide branch structures and to enhance the concentration of sialic acids at the terminal residues (Weikert et al. 1999; Hollister et al. 1998). PER.C6 cells are modified by integration of cDNA's encoding alpha 2,3-sialyltransferase, alpha 2,6-sialyltransferase and beta 1,4-galactosyltransferase proteins to further increase the sialic acid content of recombinant proteins produced on this human cell line.

Example 29

Inhibition of Apoptosis by Overexpression of Adenovirus E1B in CHO-dhfr Cells

It is known that CHO cells, overexpressing recombinant exogenous proteins, are highly sensitive for apoptotic signals, resulting in a generally higher death rate among these stable producing cell lines as compared to the wild type or original cells from which these cells were derived. Moreover, CHO cells die of apoptotic effects when agents such as lipofectamine are being used in transfection studies. Thus, CHO cells have a great disadvantage in recombinant protein production in the sense that the cells are very easily killed by apoptosis due to different reasons. Since it is known that the E1B gene of adenovirus has anti-apoptotic effects (White et al. 1992; Yew and Berk 1992), stable CHO-dhfr cells that express both heavy and light chains of the described antibodies (See, Examples 3, 4 and 5) are being transfected with adenovirus E1B cDNA's to produce a stable or transient expression of the E1 B proteins to finally ensure a lower apoptotic effect in these cells and thereby increase the production rate of the recombinant proteins. Transiently transfected cells and stably transfected cells are compared to wild type CHO-dhfr cells in FACS analyses for cell death due to the transfection method or due to the fact that they over-express the recombinant proteins.

Stable CHO cell lines are generated in which the adenovirus E1B proteins are overexpressed. Subsequently, the apoptotic response due to effects of, for instance, Lipofectamine in these stable E1 B producing CHO cells is compared to the apoptotic response of the parental cells that did not receive the E1 B gene. These experiments are executed using FACS analyses and commercially available kits that can determine the rate of apoptosis.

Example 30

Inhibition of Apoptosis by Overexpression of Adenovirus E1B in Human Cells

PER.C6 cells and derivatives thereof do express the E1A and E1B genes of adenovirus. Other human cells, such as A549 cells, are being used to stably overexpress adenovirus E1B to determine the anti-apoptotic effects of the presence of the adenovirus E1B gene as described for CHO cells (See, Example 29). Most cells do respond to transfection agents such as lipofectamine or other cationic lipids, resulting in massive apoptosis and finally resulting in low concentrations of the recombinant proteins that are secreted, simply due to the fact that only few cells survive the treatment. Stable E1B overexpressing cells are compared to the parental cell lines in their response to overexpression of toxic proteins or apoptosis inducing proteins and their response to transfection agents such as lipofectamine.

Example 31

Generation of PER.C6 Derived Cell Lines Lacking a Functional DHFR Protein

PER.C6 cells are used to knock out the DHFR gene using different systems to obtain cell lines that can be used for amplification of the exogenous integrated DHFR gene that is encoded on the vectors that are described in Examples 1 to 5 or other DHFR expressing vectors. PER.C6 cells are screened for the presence of the different chromosomes and are selected for a low copy number of the chromosome that carries the human DHFR gene. Subsequently, these cells are used in knock-out experiments in which the open reading frame of the DHFR gene is disrupted and replaced by a selection marker. To obtain a double knock-out cell line, both alleles are removed via homologous recombination using two different selection markers or by other systems as, for instance, described for CHO cells (Urlaub et al. 1983).

Other systems are also applied in which the functionality of the DHFR protein is lowered or completely removed, for instance, by the use of anti-sense RNA or via RNA/DNA hybrids, in which the gene is not removed or knocked out, but the down stream products of the gene are disturbed in their function.

Example 32

Long-Term Production of Recombinant Proteins Using Protease and Neuraminidase Inhibitors Stable clones described in Example 8 are used for long-term expression in the presence and absence of MTX, serum and protease inhibitors. When stable or transfected cells are left during a number of days to accumulate recombinant human EPO protein, a flattening curve instead of a straight increase is observed, which indicates that the accumulated EPO is degraded in time. This might be an inactive process due to external factors such as light or temperature. It might also be that specific proteases that are produced by the viable cells or that are released upon lysis of dead cells digest the recombinant EPO protein. Therefore, an increasing concentration of $CuSO_4$ is added to the culture medium after transfection and on the stable producing cells to detect a more stable production curve. Cells are cultured for several days and the amount of EPO is determined at different time points. $CuSO_4$ is a known inhibitor of protease activity, which can be easily removed during down stream processing and EPO purification. The most optimal concentration of $CuSO_4$ is used to produce recombinant human EPO protein after transient expression upon DNA transfection and viral infections. Furthermore, the optimal concentration of $CuSO_4$ is also used in the production of EPO on the stable clones. In the case of EPO in which the presence of terminal sialic acids is important to ensure a long circulation half-life of the recombinant protein, it is necessary to produce highly sialylated EPO. Since living cells produce neuraminidases that can be secreted upon activation by stress factors, it is likely that produced EPO lose their sialic acids due to these stress factors and produced neuraminidases. To prevent clipping off of sialic acids, neuraminidase inhibitors are added to the medium to result in a prolonged attachment of sialic acids to the EPO that is produced.

Example 33

Stable Expression of Recombinant Proteins in Human Cells Using the Amplifiable Glutamine Synthetase System PER.C6 and derivatives thereof are being used to stably express recombinant proteins using the glutamine synthetase (GS) system. First, cells are being checked for their ability to grow in glutamine free medium. If cells cannot grow in glutamine free medium, this means that these cells do not express enough GS, finally resulting in death of the cells. The GS gene can be integrated into expression vectors as a selection marker (as is described for the DHFR gene) and can be amplified by increasing the methionine sulphoximine (MSX) concentration resulting in overexpression of the recombinant protein of interest, since the entire stably integrated vector will be co-amplified as was shown for DHFR. The GS gene expression system became feasible after a report of Sanders et al. (1984) and a comparison was made between the DHFR selection system and GS by Cockett et al. (1990). The production of recombinant mAbs using GS was first described by Bebbington et al. (1992).

The GS gene is cloned into the vector backbones described in Example 1 or cDNA's encoding recombinant proteins and heavy and light chains of mabs are cloned into the available vectors carrying the GS gene. Subsequently, these vectors are transfected into PER.C6 and selected under MSX concentrations that will allow growth of cells with stable integration of the vectors.

Example 34

Production of Recombinant HIV gp120 Protein in a Human Cell

The cDNA encoding the highly glycosylated envelope protein gp120 from Human Immunodeficiency Virus (HIV) is determined and obtained by PCR using primers that harbor a perfect Kozak sequence in the upstream primer for proper translation initiation and convenient restriction recognition sequences for cloning into the expression vectors described in Example 1. Subsequently, this PCR product is sequenced on both strands to ensure that no PCR mistakes are being introduced.

The expression vector is transfected into PER.C6, derivatives thereof and CHO-dhfr cells to obtain stable producing cell lines. Differences in glycosylation between CHO-produced and PER.C6 produced gp120 are being determined in 2D electrophoresis experiments and subsequently in Mass Spectrometry experiments, since gp120 is a heavily glycosylated protein with mainly O-linked oligosaccharides. The recombinant protein is purified by persons skilled in the art and subsequently used for functionality and other assays. Purified protein is used for vaccination purposes to prevent HIV infections.

Example 35

Construction of pAlpha2,6ST2000/Hygro.

The fragment containing the sequence coding for alpha2,6 sialyltransferase was obtained by EcoRI digestion of plasmid pGST-Gal (a gift from Dr. I. van Die, Free University of Amsterdam). The plasmid consists of a pBR322 backbone containing the entire cDNA sequence coding for rat alpha2,6 sialyltransferase, GenBank accession no. M18769). The fragment was made blunt-ended by T4 DNA polymerase according to standard procedures. After gel purification, the alpha2,6 sialyltransferase encoding fragment was ligated into pcDNA2000/Hygro (also known as plasmid pcDNA2000/Hyg(−) which has been described in the incorporated '544 patent), which was linearized with PmeI, dephosphorylated and gel purified according to standard laboratory procedures. The resulting plasmid was named pAlpha2,6ST2000/Hygro (FIG. 1 of the instant application).

Example 36

Transfection of pAlpha2,6ST2000/Hygro in PER.C6-EPO and Selection of Over-Expressing Clones PER.C6-EPO were initially generated for other purposes, namely for experiments focusing on glycosylation of erythropoietin (EPO). EPO is a protein involved in stimulation of erythropoiesis and its activity depends heavily on its sialic acid content for in vivo functionality. The PER.C6-EPO cell line is a derivative of PER.C6 and overexpresses the human EPO protein (cells have been described in the incorporated '544 patent). The fact that this cell line is producing EPO is not believed to be critical for the present example. PER.C6-EPO cells were cultured and transfected with pAlpha2,6ST2000/Hygro, as described below.

PER.C6 cells were seeded in tissue culture dishes (10 cm diameter) with approximately 2-3 million cells/dish and were kept overnight at 37° C. and 10% $CO_2$. On the next day, cells are transfected using Lipofectamine (Gibco) according to the manufacturer's protocol. Twenty dishes were transfected each with 2 µg of pAlpha2,6ST2000/Hygro all, according to standard protocols, well known to persons skilled in the art. Another 6 dishes served as negative controls for hygromycin killing and transfection efficiency. On the next day, hygromycin was added to the dishes at a concentration of 50 µg/ml, dissolved in DMEM medium containing FES. Cells were incubated over a period of 3-4 weeks, with regular washing of the cells with fresh medium supplemented with hygromycin. Cells were monitored daily for death, comparing with the negative controls that did not receive the plasmids harboring the hygromycin selection markers. Outgrowing colonies were picked and subcultured generally as described for erythropoietin- and antibody-overexpressing cell lines in the incorporated '544 patent. Approximately 25 selected antibiotic-resistant colonies were grown subsequently in 24-wells, 6-wells plates and T25 flask without hygromycin. When cells reached growth in T75 tissue culture flasks at least one vial of each clone was frozen and stored for backup. The clones were subsequently tested for alpha2,6ST activity by FACS analysis on a FACsort apparatus (Becton Dickinson) using methods previously described by Govorkova et al. (1999). For this, the SAalpha2,6Gal-specific *Sambucus nigra* agglutinin (DIG Glycan differentiation kit, Roche) was used following the supplier's protocols. These clones were subcultured in a time span of two months, during which FACS analysis experiments were performed on a regular basis to monitor expression of alpha2,6 sialyltransferase on the cell surface. Increased expression of SAalpha2,6Gal was stable. The best alpha2,6 sialyltransferase-expressing clone, as assessed by the highest density of SAalpha2,6Gal on the cell surface, was clone 25-3.10. This clone was named "PER.C6-alpha2,6 ST." The results in FIG. 4A of the instant application show a FACS analysis on PER.C6-alpha2,6 ST at the end of the selection process. It is evident that stable transfection of pAlpha2,6ST2000/Hygro leads to markedly increased levels of SAalpha2,6Gal residues on the cell surface as compared to the maternal PER.C6 cell line. Interestingly, over-expression of alpha2,6 sialyltransferase also seems to result in lower amounts of SAalpha2,3Gal residues, as detected by FACS using alpha2,3Gal-specific *Maackia amurensis* agglutinin (FIG. 4B of the instant application). This effect is most likely due to competition of alpha2,6 sialyltransferase with endogenous alpha2,3 sialyltransferase for the same glycoprotein substrate.

Example 37

Figure 2B:
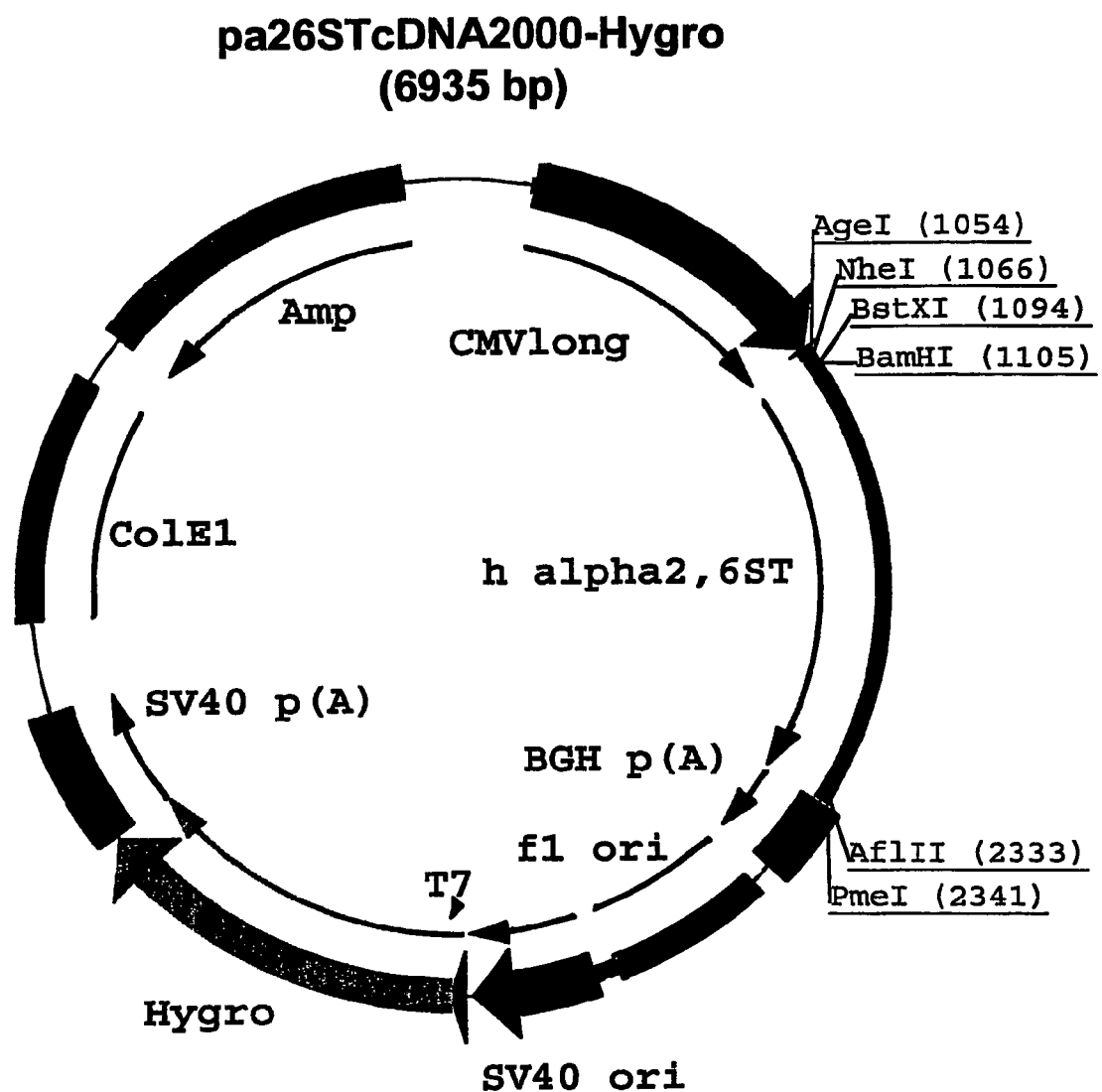

Generation of Alpha2,6- and Alpha2,3 Sialyltransferase cDNA Expression Vectors A PCR fragment containing the full length cDNA of human alpha2,6 sialyltransferase (GenBank accession no. 14735135) is obtained by Polymerase Chain Reaction (PCR) on a human cDNA library using methods well known to persons skilled in the art. The primers used for the amplification (sense: 5'-TTT TTT GGA TCC ATG ATT CAC ACC AAC CTG AAG AAA AAG-3' (SEQ ID NO: 33), antisense: 5'-TTT TTT CTT AAG TTA GCA GTG AAT GGT CCG GAA GC-3' (SEQ ID NO: 34)) contain an additional 5'-tail that allows digestion with BamHI in the sense primer and AflIII in the antisense primer, respectively. The PCR product is purified via agarose gel electrophoresis and digested with BamHI and AflIII and, subsequently, cloned into pcDNA2000/Hygro (described as pcDNA2000/Hyg(-) in the incorporated '544 patent) and into pcDNA2000/Neo (this vector was basically constructed in the same way as pcDNA2000/Hyg(-) from pcDNA2000/DHFR as has been described in detail in the incorporated '544 patent). For this, pcDNA2000/Hygro and pcDNA2000/Neo were also digested with BamHI and AflIII restriction enzymes. The sequence and the correct cloning are checked by double-stranded sequencing according to standard procedures known to persons skilled in the art of molecular biology. The resulting plasmids are named pAlpha2,6STcDNA2000/Hygro (FIG. 2A of the instant application) pAlpha2,6STcDNA2000/Neo (FIG. 2B of the instant application). They comprise nucleic acid encoding human alpha2,6 sialyltransferase under the control of the extended CMV promoter (see the incorporated '544 patent). Furthermore, the plasmids confer resistance to neomycin and hygromycin, respectively that are used to select for clones that have integrated the plasmid into their genome in a stable manner.

Figure 3B:
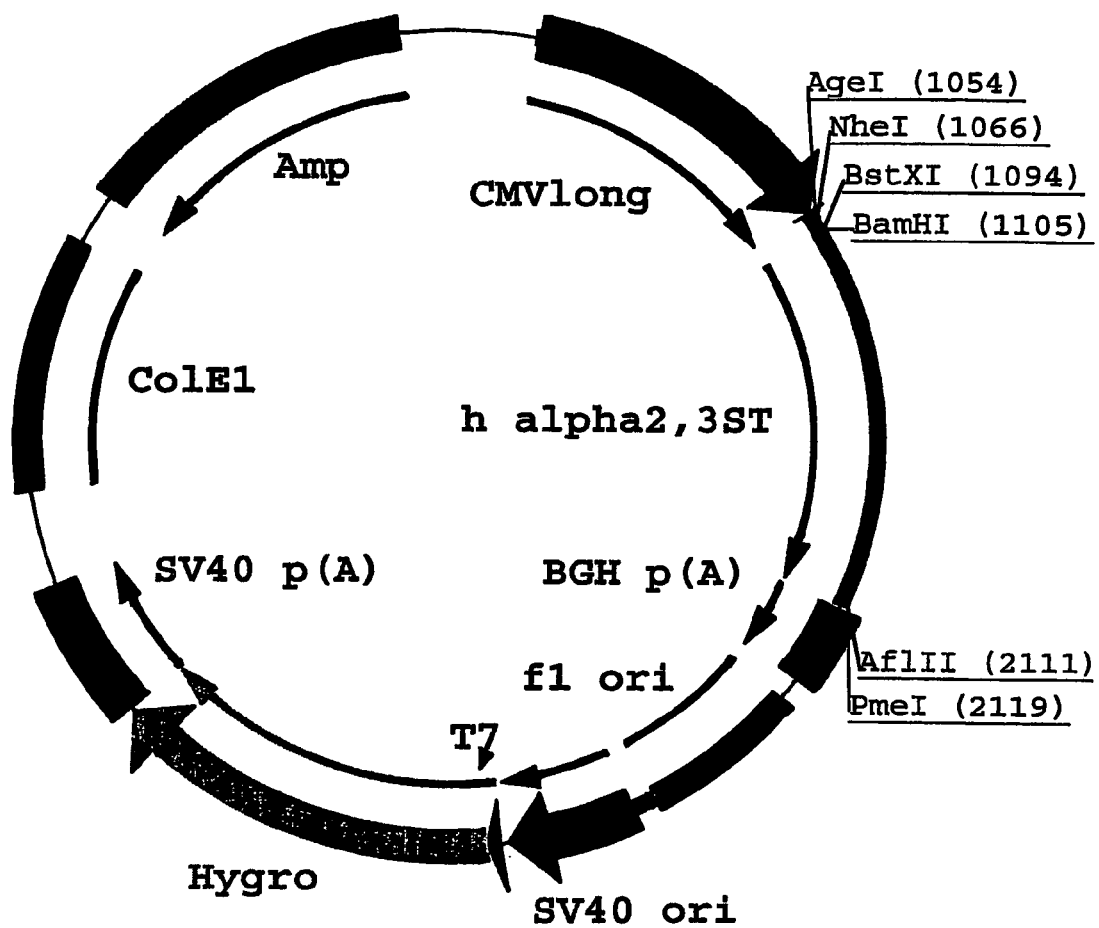

The cDNA of human alpha2,3 sialyltransferase (GenBank accession no. L23767) is obtained and cloned as described above for the human alpha 2,6 sialyltransferase gene. The primers that are used for the PCR reaction are: sense 5'-TTT TTT GGA TCC ATG TGT CCT GCA GGC TGG AAG CTC-3', (SEQ ID NO: 35), and antisense 5'-TTT TTT CTT AAG TCA GAA GGA CGT GAG GTT CTT GAT AG-3', (SEQ ID NO: 36). The resulting plasmids are named pAlpha2,3STcDNA2000/Hygro (FIG. 3A of the instant application) pAlpha2,3STcDNA2000/Neo (FIG. 3B of the instant application).

Example 38

Generation of Stable PER.C6 Cells Over-Expressing Either Human Alpha2,6- or Human Alpha2,3 Sialyltransferase Cells of the PER.C6 cell line are seeded in 40 tissue culture dishes (10 cm diameter) with approximately 2-3 million cells/dish and are kept overnight at 37° C. and 10% $CO_2$. On the next day, cells are transfected using Lipofectamine (Gibco) according to the manufacturer's protocol and to standard culturing procedures known to persons skilled in the art. Twenty dishes are transfected each with 5 μg of pAlpha2,6STcDNA2000/Neo. Another 20 dishes with non-transfected cells serve as negative controls for neomycin killing and transfection efficiency. On the next day, neomycin (0.5 mg/ml) is added to the appropriate dishes, dissolved in medium containing FBS. Cells are incubated over a period of 4-5 weeks, with regular washing of the cells with fresh medium supplemented with the selection agent. Cells are monitored daily for death, comparing with the negative controls that did not receive the plasmids harboring the neomycin and hygromycin selection markers. Outgrowing colonies are picked and subcultured generally as described for erythropoietin- and antibody-overexpressing cell lines in the incorporated '544 patent.

From each cell line, approximately 50 selected neomycin-resistant colonies are grown subsequently in 96-wells, 24-wells, 6-wells plates and T25 flask with neomycin. When cells reach growth in T25 tissue culture flasks at least one vial of each clone is frozen and stored for backup. Each clone is subsequently tested for production of recombinant human alpha2,6 sialyltransferase by FACS analysis using SAalpha2,6Gal-specific *Sambucus nigra* agglutinin as described above and as previously described by Govorkova et al. (1999). The following selection of good producer clones is based on expression, culturing behavior and viability. To allow checks for long-term viability, suspension growth in roller bottles and bioreactor during extended time periods, more vials of the best performing clones are frozen, and are selected for further investigation. These clones are subcultured in a time span of two months. During these two months, FACS analysis experiments are performed on a regular basis to monitor expression of alpha2,6 sialyltransferase on the cell surface. The best stable producer is selected and used for cell banking. This clone is expanded to generate a cell line that is named PER.C6-H-alpha2,6 ST.

Cell lines over-expressing the human alpha2,3 sialyltransferase protein are generated in generally the same way as described above for the human alpha2,6 sialyltransferase over-expressing PER.C6 cells. In this case, plasmid pAlpha2,3STcDNA2000/Neo is used. The resulting cell line is named PER.C6-H-alpha2,3 ST.

Example 39

Cell Culture and Infection with Primary and Adapted Influenza Virus Isolates in PER.C6 Cells and in Alpha2,6 Sialyltransferase-Overexpressing PER.C6 Cells Experiments were performed to compare the susceptibility to infection of PER.C6 with that of PER.C6-alpha2,6 ST. Suspension cultures of PER.C6 and PER.C6-alpha2,6 ST were cultured in serum-free ExCell 525 medium (JRH Biosciences) supplemented with 4 mM L-Glutamine (Gibco), at 37° C. and 10% $CO_2$ in 490 $cm^2$ tissue culture roller bottles during continuous rotation at 1 rpm. The procedure described below was applied for all the influenza infections reported. At the day of infection, cells were seeded in 6-well plates, at the density of $1\times10^6$ cells/ml in a final volume of 2 ml of serum-free media, containing 2 mg/ml Pen/Strep (Gibco), 200 mg/ml Fungizone (Gibco) and 3 μg/ml trypsin-EDTA (Gibco). Cells were infected with a viral inoculum of a primary isolate and with a PER.C6-adapted batch (derived from the primary isolate and passaged for 1 passage on PER.C6 cells). The primary isolate that was used is the A/Netherlands/002/01 (H1N1, A/New Caledonia like, gift from Prof. Dr. A. Osterhaus, University of Rotterdam, NL). Both batches were used at a $10^{-2}$ v/v dilution. Infected cells were kept in static culture at 35° C., in 10% $CO_2$, for six days. Viral supernatants were retrieved throughout the experiment and subsequently clarified. Clarification was performed by pelleting the cells in a microfuge at 5,000 rpm for 5 min, at room temperature. Cell pellets were analyzed by direct immunofluorescence assay as described infra. Supernatants were transferred to a new Eppendorf tube, rapidly frozen in liquid $N_2$ and stored at −80° C. until use in plaque assays (see below).

Example 40

Immunofluorescence Test

Figure 5:
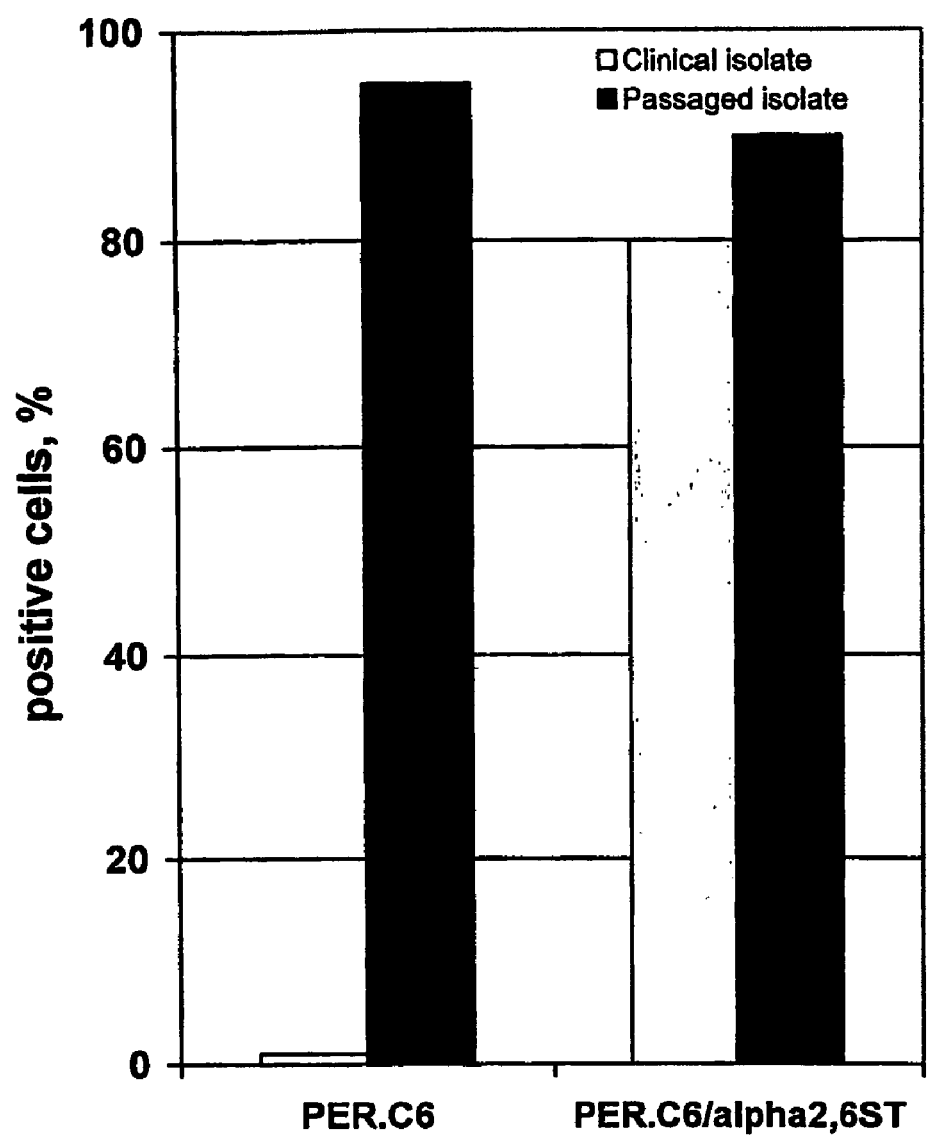
FIG. 5. Propagation of a primary clinical influenza isolate and a egg-passaged influenza batch (from the same primary isolate) on PER.C6 and PER.C6/alpha2,6ST, determined by fluorescence. Infectivity is expressed as percentage of cells positive for HA-immunofluorescent staining.

Direct immunofluorescence (I.F.) assays for the detection of Influenza virus infection were carried out in infected cells (see above) using the IMAGEN™ Influenza Virus A and B kit (Dako) according to the protocol provided by the supplier. Briefly, infected cells were centrifuged for 5 min. The supernatant was removed and the pellet resuspended in PBS. This was repeated twice to wash the cells thoroughly. The washed cell pellet was resuspended in PBS and 20 µl of cell suspension was added to each of two wells of an I.F. slide. This was allowed to dry at room temperature. The cells were fixed by adding 20 µl acetone to each well and air-dried. To each well, 20 µl of the appropriate IMAGEN Influenza reagent (i.e., labeled antibody specific Influenza A or B) was added. The slide was then incubated for 15 min at 37° C. on a damp tissue. Excess reagent was washed away with PBS and then rinsed for 5 min in PBS. The slide was air-dried at room temperature. One drop of IMAGEN mounting fluid was added to each well and a cover slip placed over the slide (this was fixed in place with a small amount of nail polish). Samples were viewed microscopically using epifluorescence illumination. Infected cells were characterized by a bright, apple-green fluorescence. The approximate percentage of cells that show positive (fluorescent green) compared with negative (red) cells was recorded. Results are shown in FIG. 5 of the instant application. It is evident that PER.C6-alpha2,6 ST supported efficiently the replication of the clinical isolate (white bars).

Example 41

Plaque Assay

Virus production in PER.C6 and PER.C6-alpha2,6 ST were studied by scoring for plaque formation in MDCK (Madin Darbin Canine Kidney) cells inoculated with virus supernatants. MDCK cells are particularly useful for such plaque assay experiments. A total of 1 ml of 10-fold diluted viral supernatants of primary and PER.C6-passaged influenza virus both propagated on PER.C6 and PER.C6-alpha2,6 ST according to the methods described in Example 39, were inoculated on MDCK cells which were grown until 95% confluence in 6-well plates in DMEM supplemented with 2 mM L-glutamine. After 1 h at 37° C., the cells were washed twice with PBS and overloaded with 3 ml of agarose mix (1.2 ml 2.5% agarose, 1.5 ml 2×MEM, 30 µl 200 mM L-Glutamine, 24 µl trypsin-EDTA, 250 µl PBS). The cells were then incubated in a humid, 10% $CO_2$ atmosphere at 37° C. for approximately 3 days and viral plaques were visually scored and counted. Results are shown in FIG. 6 of the instant application. The clinical isolate of influenza virus (white bars) and the PER.C6-passaged virus (gray bars) could infect the PER.C6-alpha2,6 ST cells very efficiently (right panel), whereas PER.C6 cells (left panel) were not very susceptible to infection by the primary clinical isolate. This shows that cells that over-express the alpha2,6 sialyltransferase are particularly useful to propagate primary virus isolates and shows that these cells are extremely useful in rapid and safe methods for the production of vaccines against, for instance, influenza infection.

Example 42

Titration of Influenza Virus Particles Using PER.C6 Cells in FACS

A novel FACS-based method was employed to measure the titer of influenza virus in supernatants. The procedure entails the quantification of replication-competent virions by detecting the fraction of cells that are productively infected within the first round of viral replication. Using a suspension culture of PER.C6 and a moiety of infection between 0.01 and 1, it is possible to obtain very accurate values within a few hours. The same titration by plaque assay with MDCK cells, which is at the moment the standard assay for influenza virus titration used by many in the art, is much more lengthy (generally almost two weeks), labor demanding, and especially less reproducible. What follows is the technical description of the materials and method employed. Here, it is shown that suspension cells can be used for titration of influenza virus particles in supernatants using FACS analysis.

PER.C6 cells that were grown in suspension in serum-free AEM Medium (Gibco) were plated in a 24-well plate (1 ml cells per well at $1 \times 10^6$ cells/ml). Trypsin-EDTA (Gibco) was added to a final concentration of 3 µg/ml. Cells were infected with an influenza virus type A supernatant (X-127, a reassortant of A/Beijing/262/95 and X-31 (obtained from the National Institute for Biological Standards and Control). 200 µl virus supernatant were added to the cells in 3-fold dilution steps, starting with undiluted virus stock. A control of mock-infected cells was included. Following addition of the virus, cells were kept for 5 h at 35° C.

Infected cells were sampled (350 µl each) in 1.5 ml Eppendorf tubes. Cold PBS was added up to 1 ml and the tubes were centrifuged for 5 min at 5,000 rpm in Eppendorf bench centrifuge. Supernatant was discarded and cells were resuspended gently in 100 µl cold Cytoperm/Cytofix permeabilizing solution (Pharmingen). After 20 min at 4° C., cold PBS (900 µl) was added and cells pelleted again, as above. Pelleted cells were resuspended in 350 µl cold-staining medium (PBS, 1% BSA, 0.1% Na Azide) containing 5 µl of influenza A nucleoprotein-specific antibody labeled with FITC (Imagen Kit, Dako). Cells were incubated at 4° C. for 15 min to 30 min and subsequently washed once with 1 ml cold PBS and once with 1 ml 1× Cellfix fixing solution (Becton Dickinson). Cells were then analyzed by FACS or stored at 4° C. in the dark for up to 1 week for subsequent FACS analysis.

Figure 7:
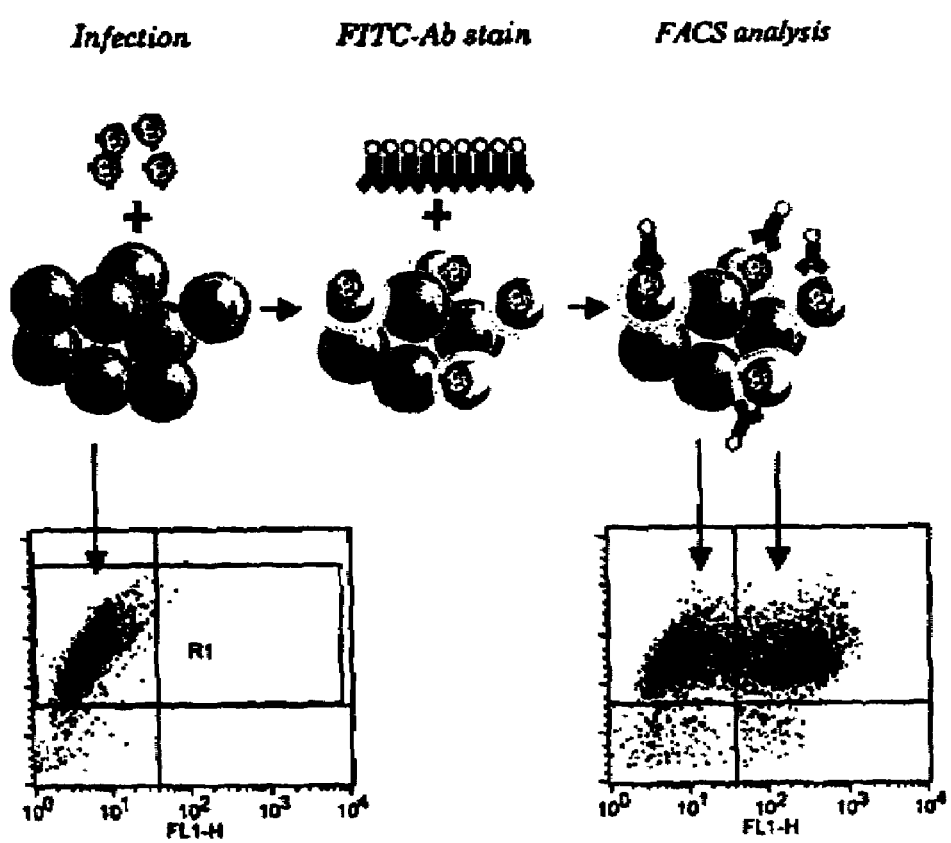
FIG. 7. Schematic representation of the influenza titration assay. First cells are infected with virus particles, then cells are incubated with antisera and subsequently used in FACS analysis in which infected cells can be separated and counted in the entire population of cells.

Stained cells were analyzed on a FACsort apparatus (Becton Dickinson). Influenza/FITC positive cells were detected in the FL1 channel and appeared in the upper right quadrant (FIG. 7 of the instant application). In the lower portion of the figure are plotted the results of the FACS analysis on uninfected cells and cells at 5 h post infection. The upper right quadrant and the upper left quadrant of the graphs represent the FITC-positive/infected and FITC-negative/uninfected cells, respectively.

Figure 8:
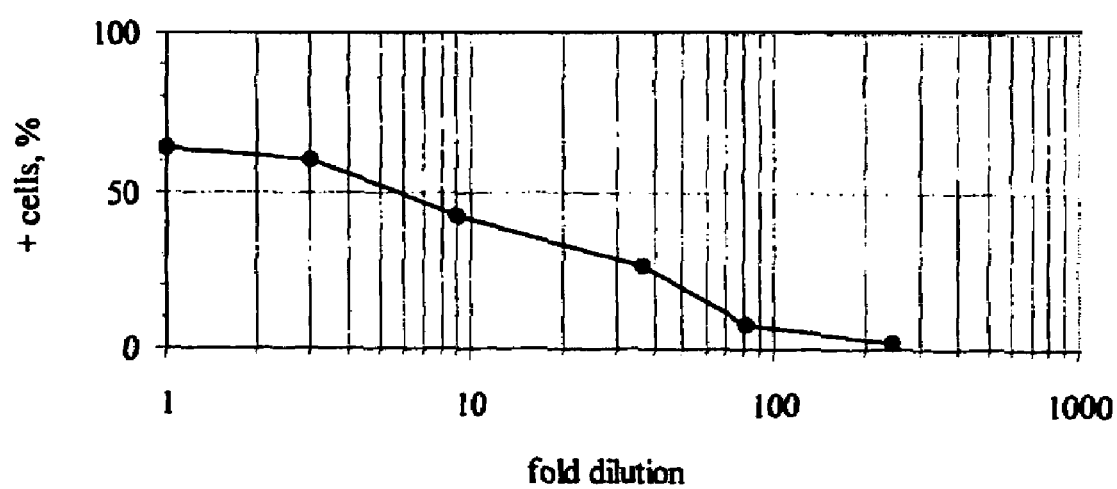
FIG. 8. Plot of the fraction of infected cells (%) over the dilution factor.

Infected cells were then plotted as percentage on the Y-axis over the dilution of the supernatant used to infect them on the X-axis (FIG. 8 of the instant application). The value that corresponds to 50% of infected cells represents the $TCID_{50}$ of the supernatant. Knowing that 1,000,000 cells were used for this initial infection, one derives that 200 µl supernatant diluted ⅙ contain 500,000 infectious particles, corresponding to a titer of $1.5 \times 10^7$ infectious particles/ml. When the same supernatant was quantified on the standard plaque assay with MDCK cells using standard procedures well known to persons skilled in the art, a value of $1.7 \times 10^7$ was obtained, with a variation of +/−50%.

Of course, different volumes and dilutions of virus supernatant can be used together with different amounts of PER.C6 to vary the sensitivity of the assay. Analogously, titers of influenza viruses other than X-127 can be measured, provided the appropriate antibody is used in the staining.

Example 43

Increased Sialylation of EPO Produced in PER.C6 Cells by the Over-Expression of α2,6-sialyltransferase To determine the effect of over-expression of α2,6-sialyltransferase on the sialylation of EPO produced in PER.C6 cells, EPO was produced in adherent cultures of an α2,6 sialyltransferase over-expressing PER.C6 cell line, i.e., PER.C6-EPO-ST clone 25-3.10 (see Example 36), and in the parental cell line PER.C6-EPO clone 25 not over-expressing the α2,6-sialyltransferase. The cells were first cultured in T-flasks in DMEM+10 mM $MgCl_2$+9% FBS. At the moment that the cells were grown to 60-70% confluency, the serum containing medium was replaced by DMEM+10 mM $MgCl_2$ without serum. The culture was then continued at 37° C. and 10% $CO_2$ for 3-4 days. The culture supernatant was thereafter harvested and EPO was purified and analyzed using methods that have been described in the incorporated WO 03/038100. The sialic acid content of the EPO produced by the PER.C6-EPO-ST clone 25-3.10 and its parental cell line was determined by iso-electric focusing. As can be observed from the results shown in FIG. 9, the sialic acid content of the EPO produced in PER.C6 cells over-expressing the α2,6-sialyltransferase was higher than that of EPO produced in the parental PER.C6 cell line in which the α2,6-sialyltransferase was not over-expressed indicating that the over-expression of the α2,6-sialyltransferase results in an increased sialylation of the PER.C6-produced EPO.

Example 44

Increased Level of Galactosylation and Fucosylation of EPO Produced in PER.C6 Cells through the Adaptation of the Cells to Growth in Suspension in Serum-Free Medium The stable PER.C6 cell line, PER.C6-022, producing EPO was used to assess the level of galactosylation of EPO when the cells were cultured adherently (using methods described in example 43) and when the cells were adapted to growth in serum-free medium. For the latter, a procedure was developed to produce EPO in PER.C6 cells that were cultured in suspension in serum free medium. The procedure is described below and was applied to several EPO-producing PER.C6 cell lines. PER.C6-EPO-022 cells were used to produce EPO with N-linked glycans structures that are typical for non-modified PER.C6 cells as described in the incorporated WO 03/038100.

For the production of PER.C6-EPO, the above indicated cell line was adapted to a serum-free medium, i.e., Excell 525 (JRH Biosciences). Therefore, the cells were first cultured to form a 70%-90% confluent monolayer in a T80 culture flask in DMEM+9% FBS+10 mM $MgCl_2$ and thereafter washed with PBS and trypsinized according to routine culture techniques. The cells were subsequently suspended in DMEM+9% FBS+10 mM $MgCl_2$ and centrifuged for 5 min. at 1000 rpm in a table centrifuge. The supernatant was discarded and the cells were re-suspended in the serum free medium, Excell 525+4 mM L-Glutamine, to a cell density of $0.3 \times 10^6$ cells/ml. A 25 ml cell suspension was put in a 250 ml shaker flask and shaken at 100 rpm at 37° C. at 5% $CO_2$. After reaching a cell density of $\geq 1 \times 10^6$ cells/ml, the cells were sub-cultured. Therefore, the cells were spun down for 5 min at 1000 rpm and suspended in fresh Excell 525+4 mM L-Glutamine to a cell density of 0.2 or $0.3 \times 10^6$ cells/ml and further cultured in shaker flasks at 37° C., 5% $CO_2$ and 100 rpm.

For production of EPO, the cells were transferred to a serum-free production medium, i.e., VPRO (JRH Biosciences), which supports the growth of PER.C6 cells to very high cell densities (usually $>10^7$ cells/ml in a batch culture). For this purpose, the cells were first cultured to $\geq 1 \times 10^6$ cells/ml in Excell 525, then spun down for 5 min at 1000 rpm and subsequently suspended in VPRO medium+6 mM L-glutamine to a density of $1 \times 10^6$ cells/ml. The cells were then cultured in a shaker flask for 7-10 days at 37° C., 5% $CO_2$ and 100 rpm. During this period, the cells grew to a density of $>10^7$ cells/ml. The culture medium was harvested after the cell viability started to decline. The cells were spun down for 5 min at 1000 rpm and the supernatant was used for the quantification and purification of EPO. The concentration of EPO was determined using ELISA (R&D systems) and turned out to be 14,044 eU/ml for the EPO produced by PER.C6-EPO-022. Thereafter, EPO was purified by affinity chromatography using an anti-EPO antibody as previously described (see, the incorporated WO 03/038100).

The composition of the N-linked glycans on EPO produced by PER.C6 cells was analyzed using MALDI-MS. Therefore, glycoprotein samples were concentrated and buffer-exchanged to 20 mM sodium phosphate (pH 7.2) using Millipore Microcon 10 concentrators, obtaining a final concentration of approx. 1 µg/µl. Subsequently, the glycoprotein was digested with PNGase F, which releases the N-linked glycans and the samples were incubated with neuraminidase, which removes the sialic acid residues. The desialylated glycan pool was analyzed without further purification using MALDI-MS. Positive ion MALDI-MS was performed on an Applied Biosystems Voyager DE Pro mass spectrometer in the reflector mode; 2,5-dihydroxybenzoic acid was used as a matrix (DHB, 10 mg/ml in 50/50/0.1 acetonitrile/water/trifluoroacetic acid).

Spectra obtained with the above-described procedures were smoothed using the functions and parameters in the Data Explorer software. First, a baseline correction was performed on the spectra using the advanced baseline correction tool (peak width 32, flexibility 0.5, degree 0.1). After this step, the function Noise Removal (std. dev to remove=2) was used to reduce the noise in the spectrum.

FIG. 10 shows representative mass profiles of the N-linked glycans on EPO produced in an adherent PER.C6 cell culture and in a PER.C6 suspension cell culture in serum-free medium. The mass profiles are clearly different and show that the masses of the N-linked sugars produced in the suspension culture are generally much larger than those produced in the adherent culture, indicating that EPO is more extensively glycosylated in PER.C6 cells that have been cultured in suspension in serum-free medium.

To obtain more insight in the differences in glycosylation under the different cell culture conditions, glycan compositions and carbohydrate structures were assigned to the peaks observed in the mass spectra using the GlycoMod software (www.expasy.ch/tools/glycomod). This software basically predicts the number of N-acetyl-hexosamines (HexNAc), Hexoses (Hex), and deoxyhexoses (dHex) that are part of a glycan structure with any particular, observed mass. Using this method, complex type carbohydrate compositions could be accurately assigned to all peaks with an intensity of ≧10%. There were no indications that any of the peaks with an intensity of ≧10% contained phosphate or sulphate. To further predict the structure of the carbohydrates it was assumed that the N-linked sugars all contained a basic core structure of two HexNAcs (2×GlcNAc), three hexoses (3× mannose) and one dHex (1× fucose). This assumption was based the generally known fucosylated core-structure of complex type N-linked sugars (Varki et al., 1999) and on sequence data of the N-glycans on PER.C6-produced EPO as described in the incorporated WO 03/038100, which confirmed that essentially all N-linked glycans on PER.C6-produced EPO contain a fucosylated core structure. The mass profiles of PER.C6-produced EPO (see, for example, FIG. 10) showed that all sugar species observed have a bigger mass than one that corresponds to a fucosylated core only. The N-glycans of the PER.C6-produced EPO therefore contain in addition to this fucosylated core structure other HexNAc and/or Hex and/or dHex residues. These residues form the antennae of the complex N-linked sugars. It was assumed that any additional dHex residue would be an α1,3-linked fucose, that any additional Hex residue would be a galactose, and that any additional dHex residue would be either GlcNAc or GalNAc. This assumption was made on the basis of the generally known structures of complex type N-linked sugars made by mammalian and human cells (Varki et al., 1999), on the sequence data of the N-glycans on PER.C6-produced EPO as described in WO 03/038100, and on the observation that the N-linked sugars of PER.C6-produced EPO can contain GalNAc (also described in WO 03/038100).

Based on the above-described assumptions, putative glycan structures were assigned to all peaks with ≧10% intensity present in the mass spectra. The relative peak heights were subsequently used to determine the relative occurrence of the different glycan species. Because the number of Gal residues, which are involved in GlcNAc-Gal (LacNAc) structures, can be deduced from the putative glycan structures it was possible to calculate the average number of Gal residues per N-linked glycan (EPO contains 3 N-linked glycans, and hence the number obtained can be multiplied by 3 to obtain the average number of such residues per EPO molecule) present on PER.C6-EPO (see, Table 1). Table 1 shows that the average number of Gal residues was significantly higher in EPO that was produced in cells that had been adapted for growth in suspension in serum-free medium (VPRO(S)) than in cells that had been grown adherently in the presence of serum (DMEM). It can therefore be concluded that the level of galactosylation is significantly increased by adaptation and growth of the cells in suspension and in serum-free medium. Table 1 shows that the average number of GalNAc residues, which are involved in GlcNAc-GalNAc (LacdiNAc) structures, was not much affected by changing the culture conditions. Yet, the average number of putative (α1,3-linked fucose, which forms the so-called Lewis x structure, was significantly increased in cells that had been adapted and cultured in suspension and in serum-free medium. This could be explained, in part, by the fact that galactosylation is increased under these conditions, which in turn results in the formation of more GlcNAc-Gal sequences to which an α1,3-linked fucose can be added. Another structure to which an α1,3-linked fucose can be added is GlcNAc-GalNAc (LacdiNAc). However, the increased α1,3-fucosylation does not seem to be due to an increased occurrence of LacdiNAc structures because the average number of GalNAc residues was not much affected by changing the culture conditions.

The average number of Gal+GalNAc residues corresponds to the average number of LacNAc and LacdiNAc structures to which an α1,3-linked fucose can potentially be added. When the ratio between the occurrence of Gal+GalNAc (part of LacNAc and LacdiNAc structures) and the occurrence of Lewis x structures is determined (see, Table 1), it can be concluded that more than twice as much of the available Gal+GalNAc residues is involved in a Lewis x structure when the cells are grown in suspension in a serum-free medium than when the cells were cultured adherently in the presence of serum. This indicates that the (α1,3)fucosylation is increased in cells that are cultured in suspension in serum-free medium.

Example 45

Level of Sialylation is Further Increased in Cells that Over-Express α2,6-Sialyltransferase and that are Cultured in Suspension in a Serum-Free Medium We reasoned that the increased level of galactosylation in suspension cultures in serum-free medium would be beneficial in obtaining a higher level of sialylation in cells that over-express the α2,6-sialyltransferase because the increased galactosylation results in the formation of more GlcNAc-Gal structures to which a sialic acid can be linked. Therefore, PER.C6-EPO clone 25-3.10 was adapted to suspension culture in serum-free medium and EPO was produced in VPRO medium as described in Example 44.

The sialic acid content of EPO was analyzed using iso-electric focusing, which was performed essentially as described in WO 03/038100. Instead of visualizing EPO using Western blot analysis, EPO was stained with colloidal blue (Novex). The bands represent EPO isoforms containing different amounts of sialic acids per EPO molecule. The sialic acid content of EPO produced in PER.C6 cells that over-expressed the α2,6-sialyltransferase was compared to that of EPREX and to EPO produced by PER.C6 cells that do not over-express the sialyltransferase (FIG. 11). The results demonstrate that EPO produced in PER.C6 cells over-expressing the rat alpha 2,6 sialyltransferase contained significantly more sialic acids than EPO produced in PER.C6 that do not over-express the sialyltransferase. In particular, the highly sialylated EPO isoforms that are present in EPREX are well represented in the EPO preparation derived from PER.C6 cells over-expressing the sialyltransferase whereas these isoforms are under-represented or absent in the EPO produced in ordinary PER.C6 cells (i.e., without overexpression of the sialyltransferase). It also appeared that the sialic acid content of EPO derived from PER.C6-EPO-ST clone 25-3.10 produced in VPRO (in the cells that have been adapted to growth in suspension in serum-free medium) has a higher sialic acid content than EPO derived from the same cell line but not adapted to serum-free medium (compare FIG. 9 with FIG. 11). This indicates that both the adaptation to growth in suspension in serum-free medium and the over-expression of the α2,6-sialyltransferase contribute to the increased level of sialylation.

Example 46

The Over-Expression of α2,6 Sialyltransferase in PER.C6 Cells Results in a Reduction of α1,3 Fucosylation EPO was produced in a serum-free suspension culture of α2,6-sialyltransferase over-expressing cells, i.e., PER.C6-

EPO-ST 25-3.10 cells and in its parental cell line not over-expressing the sialyltransferase, i.e., PER.C6-EPO clone 25, to analyze the effects of the over-expression of the α2,6-sialyltransferase on the glycosylation of EPO. The procedures for production and analysis of the N-linked glycans were as described in Example 44.

The glycan analysis (Table 2) showed that EPO produced by the α2,6-sialyltransferase over-expressing cells on average contained 0.4-0.6 Lewis-X structures per N-linked glycan whereas the EPO produced by the parental cell line, in which the sialyltransferase was not over-expressed contained 0.9 Lewis x structures per N-linked glycan. This shows that the over-expression of the sialyltransferase caused a reduction of the α1,3 fucosylation. This suggests that the fucosyl transferases responsible for the addition of α1,3-linked fucoses compete with the sialyltransferase(s) to modify the terminal GlcNAc-Gal and GlcNAc-GalNAc sequences.

Example 47

Over-Expression of α2,6 Sialyltransferase Results in a High Sialic Acid Content per N-Linked Glycan In order to determine the effect of the over-expression of the α2,6-sialyltransferase on the sialylation of the individual N-linked sugars of the PER.C6-produced EPO (PER.C6-EPO), the sialic acid content of the N-linked sugars of PER.C6-EPO was monitored. Therefore, the N-linked sugars of PER.C6-EPO were separated on charge in order to distinguish between sugars containing 0, 1, 2, 3, or 4 sialic acids.

To do so, PER.C6-EPO samples derived from cells that do or do not over-express the α2,6-sialyltransferase were concentrated and buffer-exchanged to 20 mM sodium phosphate (pH 7.2) using Millipore Microcon 10 concentrators to a concentration of approx. 0.25-0.5 μg/μl. Subsequently, the glycoprotein was digested with PNGase F, which releases the N-linked glycans. The released glycans were separated from the protein by ethanol precipitation (75% v/v at 4° C.) and were dried in a Speed Vac centrifuge at room temperature.

Next, the glycans were dissolved and labeled with anthranilic acid (AA) in 10 μl AA in dimethylsulphoxide-glacial acetic acid (30% v/v) containing 1 M cyanoborohydride. The reaction was carried out at 65° C. for 2 h, after which the labeling mixture was applied on a cellulose disk (1-cm diameter) in a glass holder. The disk was washed five times with 1 ml 96% (v/v) acetonitrile to remove AA and other reactants. Labeled glycans were eluted with 3 water washes (0.5 ml) and dried in a SPEED VAC™ centrifuge at room temperature prior to analysis.

The AA labeled glycans were separated on an HPLC using a weak anion exchange column (Vydac, 301VHP575P) with a binary gradient of A (20% Acetonitrile in water) and B (500 mM Ammonium Acetate pH 5.0, 20% Acetonitrile) at a flow rate of 0.4 ml/min. Using this method, the non-, mono-, bi-, tri- and tetra-sialylated glycans were separated, which have been confirmed with known oligosaccharide standards such as NA2, A1, A2[F], A3 and A4F (Glyko Inc., Oxford GlycoSciences, and Dextra-Labs).

The results in FIG. 12 show that the N-linked sugars of EPO produced in α2,6-sialyltransferase over-expressing PER.C6 cells contained significantly more sialic acids that the N-linked sugars of EPO produced in PER.C6 cells that do not over-express the α2,6-sialyltransferase. This demonstrates that the over-expression of the α2,6 sialyltransferase results in the production of N-linked sugars with a greater sialic acid content than when the α2,6-sialyltransferase is not over-expressed.

Example 48

Isolation of Highly Sialylated PER.C6-EPO by Ion-Exchange Chromatography

The isolation of highly sialylated EPO produced by PER.C6 is based on ion-exchange (in particular, anion exchange) chromatography during which the highly sialylated EPO molecules are separated from the less sialylated molecules. First, EPO produced by PER.C6-EPO-ST Clone 25-3.10 cells according to the methods described in Example 45 was purified by affinity chromatography using the EPO-specific E14 monoclonal antibody as described in the incorporated WO 03/038100. In this step, EPO was eluted with 0.1 M glycine-HCl, pH 2.7, which was immediately neutralized by adding potassium phosphate buffer, pH 8.0. The resulting buffer was thereafter exchanged using a Hiprep 26/10 desalting column to 20 mM Tris, 20 μM CuSO$_4$ (pH 7). Then, the purified EPO was loaded on a HiTrap Q HP column (Pharmacia). The column was first washed with loading buffer (20 mM Tris, 20 mM CuSO$_4$ (pH 7) and then step-wise eluted with increasing concentrations of elution buffer (20 mM Tris, 20 μM CuSO$_4$, 1M NaCl). EPO containing a low or medium sialic acid content was first eluted with 11.5% elution buffer (115 mM NaCl) and the highly sialylated EPO was eluted with 25% elution buffer (250 mM NaCl). The sialic acid content of the resulting fractions of EPO was analyzed using iso-electric focusing as described in example 45.

FIG. 13 shows the sialic acid content of fractionated and non-fractionated PER.C6-EPO. The results show that the fractionation procedure resulted in the purification and enrichment of the highly sialylated EPO molecules.

FIG. 14 shows the MALDI-MS spectrum of the highly sialylated PER.C6-EPO fraction that was de-sialylated for the mass spectrometry analysis.

The interpretation of the spectrum based on the assumptions described in example 44 revealed that the fractionated, highly sialylated PER.C6-EPO preparation contained predominantly tetra-antennary, fully galactosylated N-linked sugars.

The quantification of the average number of Gal, GalNac, and Lewis-X structures per N-linked glycan revealed that the fractionated EPO molecules contained a higher average number of Gal residues but a lower average number of GalNAc and Lewis x structures that the total pool of EPO molecules from which they originated (see, Table 3). This shows that EPO molecules with an increased number of Gal residues and a reduced number of GalNAc and Lewis x residues can be selected when highly sialylated EPO molecules are fractionated and enriched on the basis of their charge using ion-exchange chromatography.

Example 49

Erythropoietic Activity of Highly Sialylated PER.C6-EPO

To show that the increase in sialic acid content of PER.C6-EPO results in an increased erythropoietic activity, the erythropoietic activity of the highly sialylated PER.C6-EPO such as produced according to Example 46 is studied in rats. The potential of recombinant human EPO to stimulate the production of red blood cells can be monitored in a rodent model that has been described by Barbone et al.

(1994). According to this model, the increase in the reticulocyte counts is used as a measure for the biological activity of the recombinant human EPO preparation. Reticulocytes are the precursors of red blood cells and their production, in response to EPO, can be used as a measure for the potential of EPO in stimulating the production of red blood cells. An increased production of red blood cells, in turn, leads to a higher hematocrit value.

The activities of the highly sialylated PER.C6™-EPO and EPREX are compared in six groups of three Wag/Rij rats. Various doses of PER.C6™-EPO, EPREX and diluent buffer as a negative control are injected intravenously in the penile vein at day 0, 1, and 2. PER.C6™-EPO and EPREX are administered at a dose of 1, 5, 25, or 125 eU (Elisa units) as determined by the commercially available EPO-specific R&D Elisa Kit. All EPO preparations are diluted to the proper concentration in PBS/0.05% TWEEN 80 in a total volume of 500 µl. At day 3, 250 µl of EDTA blood is sampled by tongue puncture. On the same day, the percentage of reticulocytes in the total red blood cell population is determined.

Example 50

Determination of Sialic Acid Content of PER.C6 Produced EPO by Iso-Electric Focusing and Densitometric Analysis The sialic acid content of various samples of affinity purified, PER.C6-produced EPO was analyzed using iso-electric focusing, which was performed on an IsoGel agarose IEF plate (Cambrex) soaked in an ampholyte solution pH 3-10 containing 8 M urea. The EPO bands were visualized with colloidal blue (Novex). As indicated in FIG. 15, the bands represent EPO isoforms containing different numbers of sialic acids per EPO molecule. The relative amount for each isoform was determined using densitometric analysis of the bands. The average number of sialic acid residues per EPO molecule was calculated using the formula:

$$\sum_{n=0-15} (A_n * n)$$

A=relative amount of each isoform
n=isoform number(corresponding to the number of sialic acid residues per EPO molecule)

Using this method, the average sialic acid content of EPO produced by the clone PER.C6-EPO-022 (as described in example 44), and of EPO produced by the PER.C6-EPO-ST cell line clone 25-3.10 (as described in example 45), and of EPO that was obtained after fractionation of the highly sialylated PER.C6-EPO-ST molecules (as described in Example 48) as well as of EPREX® was found to be 3.0, 9.0, 12.6 and 12.4, respectively. Alternative methods to calculate the sialic acid content of the recombinant EPO fractions could also be used, e.g., the method described in U.S. Pat. No. 5,856,298, example 2, or a procedure as described by Jourdian et al., J Biol Chem. 246, 430 (1971), or modifications of such methods known to the person skilled in the art.

Example 51

Construction of the EPO-ST3 Expression Vector
In order to construct an expression vector for the simultaneous expression of EPO and α2,3-sialyltransferase, the EPO coding sequence was amplified by PCR (forward primer: 5'-CCAGGCGCGCCACCATGGGGGTGCAC-GAATGTCC-3' (SEQ ID NO:37), reverse primer: 5'-CCGGGTTAACTCATCTGTCCCCTGTCCTGC-3') (SEQ ID NO:38). The resulting PCR fragment was digested with AscI and HpaI and inserted into the same restriction sites of pcDNA3002Neo, resulting in the vector pCP-EPO (FIG. 16A). The human α2,3-sialyltransferase coding sequence (gene named SIAT4C or STZ; GenBank accession no. L23767, see also U.S. Pat. No. 5,494,790) was amplified by PCR (forward primer: 5'-GGACTAGTGGATCCGC-CACCATG-3') (SEQ ID NO:39), reverse primer: 5'-GCTCTAGATCAGAAGGACGTGAGGTTCTTG-3') ) (SEQ ID NO:40), digested with BamHI and XbaI and inserted into the BamHI and NheI site of pCP-EPO. The resulting vector was named pEPO-ST3 (FIG. 16B).

Example 52

Transient Expression of pEPO-ST3 in PER.C6 Cells
The day before transfection, PER.C6 cells were seeded in T175 culture flasks at a density of 35 million cells/flask and cultured in DMEM, containing 10 mM $MgCl_2$ and 9% fetal bovine serum, at 37° C. and 10% $CO_2$. Transfection was carried out with 28 µg pEPO-ST3 (see Example 51, FIG. 16B) or pCP-EPO (as a control; see Example 51, FIG. 16A) per flask, using Lipofectamine (Gibco) according to the manufacturers instructions, using techniques well known to persons skilled in the art. Three or four days after transfection, the culture supernatants were harvested, and cleared by centrifugation and filtration. The EPO concentrations in the supernatants were determined by ELISA (using a commercially available kit from R&D systems), and EPO was purified by affinity chromatography. The concentration of the purified EPO samples was determined by HPLC, and 18 µg of the purified EPO samples were subsequently analyzed by iso-electric focusing (IEF) in order to separate the EPO isoforms (FIG. 17). It was found that PER.C6 cells, transiently transfected with the pEPO-ST3 construct, produced EPO with a significantly increased level of sialylation (as compared to the control construct pCP-EPO, which lacks the α2,3-sialyltransferase). This demonstrates that, like for an α-2,6-sialyltransferase, also the co-expression of an α2,3-sialyltransferase can be used to increase the sialylation level of EPO produced in PER.C6 cells.

Example 53

Stable Expression of pEPO-ST3 in PER.C6 Cells
Transfection, Isolation and Screening of Parental Clones
PER.C6 clones producing highly sialylated erythropoietin (EPO) were generated by expressing human EPO and human α-2,3 sialyltransferase from a single plasmid pEPO-ST3 (see example 51). To obtain stable clones we performed a lipofectAMINE based transfection with construct pEPO-ST3. Stable clones were selected in DMEM (Gibco) supplemented with 10% Fetal Bovine Serum containing the selection agent GENETICIN® (final concentration 0.5 mg/ml). Three weeks after initiation of the transfection procedure, GENETICIN®-resistant clones grew out. A total of 479 clones were selected for isolation. The isolated clones were cultured in selection medium, until 70-90% confluency in 96-well plates. During the passage from 96-well plates to 24-well plates, supernatant were harvested and stored at 2-8° C. until screening. The supernatants of 346 clones were screened for EPO production using an EPO specific ELISA (QUANTIKINE®IVD®: Human EPO Immunoassay, manufacturer's protocol). Expression levels between clones were found to vary between background levels and more than 400 eU/ml/day. The 15% highest ranked clones and 15% of randomly selected clones (of clones producing more than 50 eU/ml/day but less than the 15% highest producers) were selected for sub-culturing resulting in a total of 103 clones. During the cell expansion phase, a parallel culture of the selected clones was established for determination of EPO levels. The information from this second screening was used to select 50 clones.

Productivity and Quality of Clones in Serum Containing Medium

Adherent cultures of these clones were initiated in T80 flasks to generate material for purification/analysis purposes. The cells were cultured in DMEM supplemented with 10% Fetal Bovine Serum for 3-5 days. Then, the material was harvested. The amount of EPO present in the culture supernatants varies from 541 to 3783 eU/ml.

After purification of EPO by affinity chromatography the samples were analyzed by Isoelectric Focusing Gel electrophoresis, as described supra. Representative results are presented in FIG. 18. Some clones did not appear to have a strongly increased sialylation level of EPO (e.g., lanes 9-12), but it can be seen that EPO produced by several of the analyzed clones has significantly improved sialylation (i.e., on average, more EPO isoforms with high numbers of sialic acids) compared to EPO produced without over-expression of α-2,3-sialyltransferase (e.g., lanes 2, 3 and in particular 13 and 14). Clearly, a screening of several clones is sufficient to identify clones with the desired increased level of sialylation.

In conclusion, co-expression of human EPO and human α-2,3-sialyltransferase from a single plasmid results in clones with increased levels of sialylation of the EPO molecules as compared to clones expressing EPO only.

Tables

TABLE 1

| PER.C6-EPO produced in | Gal | GalNAc | Lewis x | Gal + GalNAc: Lewis x |
|---|---|---|---|---|
| DMEM | 1.8 | 0.5 | 0.6 | 4.0. |
| VPRO (S) | 2.7 | 0.7 | 1.9 | 1.8 |

Table 1: Average number of Gal, GalNAc, and Lewis x structures per N-linked glycan present on PER.C6-produced EPO. EPO was produced either in an adherent culture (DMEM) or in a suspension culture in the serum-free VPRO medium (VPRO [S]). The last column represents the ratio of the average number of terminal Gal+GalNac residues over the average number of Lewis-X structures.

TABLE 2

| α2,6 sialyltransferase | Lewis x |
|---|---|
| without | 0.9 |
| with | 0.4-0.6 |

Table 2: Average number of Lewis x structures per N-linked glycan present on EPO produced in PER.C6 cells that do (i.e., PER.C6-EPO-ST clone 25-3.20) or do not (i.e., PER.C6-EPO clone 25) over-express the α2,6 sialyltransferase.

TABLE 3

| EPO preparation | Gal | GalNAc | Lewis x |
|---|---|---|---|
| Total EPO | 2.5 | 0.5 | 0.5 |
| Fractionated EPO | 3.2 | 0.3 | 0.2 |

Table 3: Average number of Gal, GalNAc, and Lewis x structures per N-linked glycan found in the total pool of EPO molecules that are produced in a serum-free suspension culture of α2,6 sialyltransferase over-expressing PER.C6 cells and in the highly sialylated EPO fraction thereof, which was obtained using the procedures described in example 46.

TABLE 4

| Fig. 15, lane | EPO preparation | Lewis X | Sialic acid |
|---|---|---|---|
| 1 | PER.C6 suspension serum-free (Example 44) | 5.7 | 3.0 |
| 2 | PER.C6 + overexpressed α-2,6-sialyltransferase suspension serum-free (Example 45) | 1.2-1.8 | 9.0 |
| 3 | 3. fractionated highly sialylated EPO (Example 48) | 0.6 | 12.6 |
| 4 | EPREX (commercially available EPO) | 0 | 12.4 |

Table 4. Lewis X and sialic acid content on glycans of different EPO preparations (see, Example 50). Contents are per EPO molecule.

REFERENCES

Baldwin R W, Byers V S (1986) Monoclonal antibodies in cancer treatment. Lancet 1, 603-605.

Barbas C F, Kang A S, Lerner R A and Benkovic S J (1991) Assembly of combinatorial antibody libraries on phage surfaces: The gene III site. Proc Natl Acad Sci USA. 88, 7978.

Baum L G and Paulson J C (1990) Sialyloligosaccharides of the respiratory epithelium in the selection of human influenza virus receptor specificity. Acta Histochem Suppl 40:35-8

Bebbington C R, Renner G, Thomson S, Abrams D, Yarranton G T (1992) High-level expression of a recombinant antibody from myeloma cells using a glutamine synthetase gene as an amplifiable selectable marker. Bio/technology 10, 169-175.

Borrebaeck C A K, Malmborg A-C and Ohlin M (1993) Does endogenous glycosylation prevent the use of mouse monoclonal antibodies as cancer therapeutics? Immunology Today 14, 477-479.

Borrebaeck C A K (1999) Human monoclonal antibodies: The emperor's new clothes? Nature Biotech. 17, 621.

Boshart W, Weber F, Jahn G, Dorsch-Hasler K, Fleckenstein B, Schaffner W (1985) A very strong enhancer is located upstream of an immediate early gene of human cytomegalovirus. Cell 41, 521-530.

Bruggeman M, Spicer C, Buluwela L, Rosewell I, Barton S, Surani M A, Rabbits T H (1991) Human antibody production in transgenic mice: expression from 100 kb of the human IgH locus. Eur J Immunol. 21, 1323-1326.

Bulens F, Vandamme A-M, Bemar H, Nelles L, Lijnen R H, and Collen D (1991) Construction and characterization of a functional chimeric murine-human antibody directed against human fibrin fragment-D dimer. Eur J Biochem. 195, 235-242.

Burton D R and Barbas III C F (1994) Human antibodies from combinatorial libraries. Adv Immunol. 57, 191-280.

Carter P, Presta L, Gorman C M, Ridgway J B, Henner D, Wong W L, Rowland A M, Kotts C, Carver M E and Shephard H M (1992) Humanization of an anti-p185HER2 antibody for human cancer therapy. Proc Natl Acad Sci USA 89, 4285-4289.

Clarkson T, Hoogenboom H R, Griffiths A and Winter G (1991) Making antibody fragments using phage display libraries. Nature 353, 624.

Claas E C, Osterhaus A D, van Beek R, De Jong J C, Rimmelzwaan G F, Senne D A, Krauss S, Shortridge K F and Webster R G (1998) Human influenza A HSN1 virus related to a highly pathogenic avian influenza virus. Lancet 351:472-427

Cockett M I, Bebbington C R, Yarranton G T (1990) High level expression of tissue inhibitor of metalloproteinases in Chinese hamster ovary cells using glutamine synthetase gene amplification. Bio/technology 8, 662-667.

Couceiro J N, Paulson J C and Baum L G (1993) Influenza virus strains selectively recognize sialyl-oligosaccharides on human respiratory epithelium; the role of the host cell in selection of hemagglutinin receptor specificity. Virus Res 29:155-165

Crowe J S, Hall V S, Smith M A, Cooper H J, and Tite J P (1992) Humanized monoclonal antibody CAMPATH-1H: myeloma cell expression of genomic constructs, nucleotide sequence of cDNA constructs and comparison of effector mechanisms of myeloma and Chinese hamster ovary cell-derived material. Clin Exp Immunol 87, 105-110.

Daniels P S, Jeffries S, Yates P, Schild G C, Rogers G N, Paulson J C, Wharton S A, Douglas A R, Skehel J J and Wiley D C (1987) The receptor-binding and membrane-fusion properties of influenza virus variants selected using anti-haemagglutinin monoclonal antibodies. EMBO J 6:1459-1465

Debbas M, White E (1993) Wild-type p53 mediates apoptosis by E1A, which is inhibited by E1B. Genes Dev. 7, 546-554.

Delorme E, Lorenzini T, Giffin J, Martin F, Jacobsen F, Boone T, Elliot S (1992) Role of glycosylation on the secretion and biological activity of erythropoietin. Biochemistry 31, 9871-9876.

Farrow S N, White J H, Martinou I, Raven T, Pun K T, Grinham C J, Martinou J C, Brown R (1995) Cloning of a bcl-2 homologue by interaction with adenovirus E1B 19K. Nature 374, 731-733.

Fishwild D M, O'Donnell S L, Bengoechea T, Hudson D V, Harding F, Bernhard S L, Jones D, Kay R M, Higgins K M, Schramm S R, Lonberg N (1996) High-avidity human IgG kappa monoclonal antibodies from a novel strain of minilocus transgenic mice. Nat Biotechnol. 14, 845-851.

Fukuta K, Abe R, Yokomatsu T, Kono N, Asanagi M, Omae F, Minowa M T, Takeuchi M, Makino T (2000) Remodeling of sugar chain structures of human interferon-γ. Glycobiology 4:412-430.

Fussenegger M, Bailey J E, Hauser H, Mueller P P (1999) Genetic optimization of recombinant glycoprotein production by mammalian cells. Trends Biotechn. 17, 35-42.

Freidin J E, Lefvert A K, Mellstedt H (1990) Pharmacokinetics of the mouse monoclonal antibody 17-1A in cancer patients receiving various treatment schedules. Cancer Res. 50, 4866-4871.

Galili U (1993) Interaction of the natural anti-Gal antibody with alpha-galactosyl epitopes: a major obstacle for xenotransplantation in humans. Immunol Today 14, 480-482.

Gambaryan A S, Robertson J S and Matrosovich M N (1999) Effects of egg-adaptation on the receptor-binding properties of human influenza A and B viruses. Virology 258: 232-239

Gambaryan A S, Tuzikov A B, Piskarev V E, Yamnikova S S, Lvov D K, Robertson J S, Bovin N V and Matrosovich M N (1997) Specification of receptor-binding phenotypes of influenza virus isolates from different hosts using synthetic sialylglycopolymers: non-egg-adapted human H1 and H3 influenza A and influenza B viruses share a common high binding affinity for 6'-sialyl (N-acetyl lactosamine). Virology 232:345-350

Garrard L, Yang M, O'Connell M, Kelley R and Henner D J (1991) Fab assembly and enrichment in a monovalent phage display system. BioTechnology 9, 1373.

Gibbs M J, Armstrong J S and Gibbs A J (2001) Recombination in the hemagglutinin gene of the 1918 "Spanish flu." Science 293:1842-1845
Goldwasser E, Eliason J F, Sikkema D (1975) An assay for erythropoietin in vitro at the milliunit level. Endocrinology 97, 315-23.
Gorman C M, Gies D, McCray G, Huang M (1989) The human cytomegalovirus major immediate early promoter can be trans-activated by adenovirus early proteins. Virology 171, 377-385.
Govorkova E A, Matrosovich M N, Tuzikov A B et al. (1999) Selection of receptor-binding variants of human influenza A and B viruses in baby hamster kidney cells. Virology 262:31-38
Grabenhorst E, Hoffinann A, Nimtz M, Zettlmeissl G, and Conradt H S (1995) Construction of stable BHK-21 cells coexpressing human secretory glycoproteins and human Gal(β1-4)GlcNAc-R α2,6-sialyltransferase. Eur. J. Biochem. 232:718-725.
Graham F L, Smiley J, Rusell W C and Nairn R (1977) Characteristics of a human cell line transformed by DNA from human adenovirus type 5. J. Virol. 36, 59-74
Green L L, Hardy M C, Maynard-Currie C E, Tsuda H, Louie D M, Mendez M J, Abderrahim H, Noguchi M, Smith D H, Zeng Y (1994) Antigen-specific human monoclonal antibodies from mice engineered with human Ig heavy and light chain YACs. Nat Genet. 7, 13-21.
Hale G, Dyer M J S, Clark M R, Phillips J M, Marcus R, Reichmann L, Winter G and Waldmann H (1988) Remission induction in non-Hodgkin lymphoma with reshaped human monoclonal antibody CAMPATH-1H. Lancet 2, 1394-1399.
Hammerling U, Kroon R, Wilhelmsen T, Sjˆdin L (1996) in vitro bioassay for human erythropoietin based on proliferative stimulation of an erythroid cell line and analysis of carbohydrate-dependent microheterogeneity. J Pharm Biomed An. 14, 1455-1469.
Han J, Sabbatini P, Perez D, Rao L, Modha D, White E (1996) The E1B 19K protein blocks apoptosis by interacting with and inhibiting the p53-inducible and death-promoting Bax protein. Genes Dev. 10, 461-477.
Harduin-Lepers A, Vallejo-Ruiz V, Krzewinski-Recchi M A, Samyn-Petit B, Julien S, and Delannoy P (2001) The human sialyltransferase family. Biochimie 83:727-737.
Hatta N, Gao P, Halfmann P and Kawaoka Y (2001) Molecular basis for high virulence of Hong Kong H5N1 influenza A viruses. Science 293:1840-1842

Havenga M J, Werner A B, Valerio D, van Es H H (1998) Methotrexate selectable retroviral vectors for Gaucher disease. Gene Ther. 5, 1379-1388.

Hollister J R, Shaper J H, Jarvis D J (1998) Stable expression of mammalian beta1,4-galactosyltransferase extends the N-glycosylation pathway in insect cells. Glycobiology 8, 473-480.

Huls G A, Heijnen I A F M, Cuomo M E, Koningsberger J C, Wiegman L, Boel E, Van der Vuurst de Vries A-R., Loyson S A J., Helfrich W., Van Berge Henegouwen G P., Van Meijer M., De Kruif J. and Logtenberg T (1999) A recombinant, fully human monoclonal antibody with anti-tumor activity constructed from phage-displayed antibody fragments. Nature Biotechnol. 17, 276-281.

Ilobi CP, Henfrey R, Robertson J S, Mumford J A, Erasmus B J and Wood J M (1994) Antigenic and molecular characterization of host cell-mediated variants of equine H3N8 influenza viruses. J Gen Virol 75:669-673

Isaacs J D, Watts R A, Hazleman B L, Hale G, Keogan M T, Cobbold S P, Waldmann H (1992) Humanized monoclonal antibody therapy for rheumatoid arthritis. Lancet 340, 748-52.

Ito T, Suzuki Y, Takada A, Kawamoto A, Otsuki K, Masuda H, Yamada M, Suzuki T, Kida H and Kawaoka Y (1997) Differences in sialic acid-galactose linkages in the chicken egg amnion and allantois influence human influenza virus receptor specificity and variant selection. J Virol 71:3357-3362.

Jacobovits A (1995) Production of fully human antibodies by transgenic mice. Curr Opin Biotechnol. 6, 561-566.

Jenkins N, Parekh R B, James D C (1996) Getting the glycosylation right: implications for the biotechnology industry. Nat Biotechnol. 14, 975-81.

Jenkins N, Buckberry L, Marc A, Monaco L (1998) Genetic engineering of alpha 2,6-sialyltransferase in recombinant CHO cells. Biochem Soc Trans. 26, S115.

Kawashima I, Ozawa H, Kotani M, Suzuki M, Kawano T, Gomibuchi M, Tai T (1993) Characterization of ganglioside expression in human melanoma cells: immunological and biochemical analysis. J Biochem (Tokyo) 114, 186-193.

Kay R, Takei F, Humphries R K (1990) Expression cloning of a cDNA encoding M1/69. J Immunol. 145, 1952-1959.

Kitamura T, Tange T, Terasawa T, Chiba S, Kuwaki T, Miyagawa K, Piao Y-F, Miyazono K, Urabe A, Takaku F (1989) Establishment and characterization of a unique human cell line that proliferates dependently on GM-CSF, IL-3, or erythropoietin. J Cell Physiol. 140, 323-334.

Kohler G and Milstein C (1975) Continuous cultures of fused cells secreting antibody of predefined specificity. Nature 256:495.

Krystal G, Eaves A C, Eaves C J (1981) A quantitative bioassay for erythropoietin, using mouse bone marrow. J Lab Clin Med. 97, 144-157.

Krystal G (1983) A simple microassay for erythropoietin based on 3H-thymidine incorporation into spleen cells from phenylhydrazine treated mice. Exp Hematol. 11, 649-660.

Lee E U, Roth J, Paulson J C (1989) Alteration of terminal glycosylation sequences on N-linked oligosaccharides of Chinese hamster ovary cells by expression of beta-galactoside alpha 2,6-sialyltransferase. J Biol Chem. 264, 13848-13855.

Leist M, et al. (2004) Derivatives of erythropoietin that are tissue protective but not erythropoietic. Science 305, 239-242.

Levrero M, Barban V, Manteca S, Ballay A, Balsamo C, Avantaggiata M L, Natoli G, Skellekens H, Tiollais P, Perricaudet M (1991) Defective and non-defective adenovirus vectors for expression foreign genes in vitro and in vivo. Gene 101, 195-202.

Liu C K, Wei G, Atwood W J (1998) Infection of glial cells by the human polyomavirus J C is mediated by an N-linked glycoprotein containing terminal alpha(2-6)-linked sialic acids. J Virol 72:4643-4639.

Lonberg N, Taylor L D, Harding F A, Trounstine M, Higgins K M, Schramm S R, Kuo C C, Mashayekh R, Wymore K, McCabe J G (1994) Antigen-specific human antibodies from mice comprising four distinct genetic modifications. Nature 368, 856-859.

Lonberg N, Huszar D (1995) Human antibodies from transgenic mice. Int Rev Immunol. 13, 65-93.

Lowder J N, Meeker T C, Levy R (1985) Monoclonal antibody therapy of lymphoid malignancy. Cancer Surv. 4, 359-375.

McCafferty J, Griffiths A D, Winter G and Chiswell D J (1990) Phage antibodies: filamentous phage displaying antibody variable domains. Nature 348, 552.

Mellstedt H, Frodin J E, Masucci G, Ragnhammar P, Fagerberg J, Hjelm A L, Shetye J, Wersall P, Osterborg A (1991) The therapeutic use of monoclonal antibodies in colorectal carcinoma. Semin Oncol. 18, 462-477.

Mendez M J, Green L L, Corvalan J R, Jia X C, Maynard-Currie C E, Yang X D, Gallo M L, Louie D M, Lee D V, Erickson K L, Luna J, Roy C M, Abderrahim H, Kirschenbaum F, Noguchi M, Smith D H, Fukushima A, Hales J F, Klapholz S, Finer M H, Davis C G, Zsebo K M, Jakobovits A (1997) Functional transplant of megabase human immunoglobulin loci recapitulates human antibody response in mice. Nat Genet. 15, 146-156.

Minch S L, Kallio P T, Bailey J E (1995) Tissue plasminogen activator coexpressed in Chinese hamster ovary cells with alpha(2,6)-sialyltransferase contains NeuAc alpha(2,6) Gal beta(1,4)Glc-N-AcR linkages. Biotechn Prog. 11, 348-351.

Morrison et al. Chimeric human antibody molecules: mouse antigen-binding domains with human constant region domains, Proc. Nat'l Acad. Sci. (USA), 81:6851-55 (1984).

Muchmore E A, Milewski M, Varki A, Diaz S (1989) Biosynthesis of N-glycolyneuraminic acid.

The primary site of hydroxylation of N-acetylneuraminic acid is the cytosolic sugar nucleotide pool. J Biol Chem. 264, 20216-20223.

Nadler L, Stashenko P, Hardy R, Kaplan W, Burton L, Kufe D W, Antman K H, Schlossman S F (1980) Serotherapy of a patient with a monoclonal antibody directed against a human lymphoma-associated antigen. Cancer Res. 40, 3147-3154.

Newman R W, Jennings R, Major D L, Robertson J S, Jenkins R, Potter C W, Burnett I, Jewes L, Anders M, Jackson D and et al. (1993) Immune response of human volunteers and animals to vaccination with egg-grown influenza A (H1N1) virus is influenced by three amino acid substitutions in the haemagglutinin molecule. Vaccine 11:400-406.

Oi V T, Morrison S L, Herzenberg L A, Berg P (1983) Immunoglobulin gene expression in transformed lymphoid cells. Proc Natl Acad Sci USA. 1983 80, 825-829.

Olive D M, Al-Mulla W, Simsek M, Zarban S, al-Nakib W (1990) The human cytomegalovirus immediate early enhancer-promoter is responsive to activation by the adenovirus-5 13S E1A gene. Arch Virol. 112, 67-80.

Owens R J and Young R J. (1994) The genetic engineering of monoclonal antibodies. J. Immunol Methods 168, 149-165.

Pau M G, Ophorst C, Koldijk M H, Schouten G, Mehtali M and Uytdehaag F (2001) The human cell line PER.C6 provides a new manufacturing system for the production of influenza vaccines. Vaccine 19:2716-2721.

Potter W P (1998). Chronicle of influenza pandemics. In Textbook of influenza, N K G, R G Webster and A J Hay, eds. (Oxford) pp. 3-18.

Prati E G P, Matasci M, Suter T B, Dinter A, Sburlati A R, and Bailey J E (2000) Engineering of coordinated up- and down-regulation of two glycosyltransferases of the O-glycosylation pathway in Chinese hamster ovary (CHO) cells. Biotech. and Bioeng. 68:239-244.

Reff M E, Carner K, Chambers K S, Chinn PC, Leonard J E, Raab R, Newman R A, Hanna N and Anderson D R (1994) Depletion of B cells in vivo by a chimeric mouse human monoclonal antibody to CD20. Blood 83, 435-445.

Reichmann L, Clark M, Waldmann H and Winter G (1988) Reshaping human antibodies for therapy. Nature 322, 323-327.

Riethmuller G, Riethmuller G, Schneider-Gadicke E, Schlimok G, Schmiegel W, Raab R, Hoffken K, Gruber R, Pichlmaier H, Hirche H, Pichlmayr R, et al. (1994) Randomized trial of monoclonal antibody for adjuvant therapy of resected Dukes' D colorectal carcinoma. Lancet 343, 1177-1183.

Rother R P and Squinto S P (1996) The alpha-Galactosyl epitope: A sugar coating that makes viruses and cells unpalatable. Cell 86, 185-188.

Robertson J S, Cook P, Nicolson C, Newman R and Wood J M (1994) Mixed populations in influenza virus vaccine strains. Vaccine 12:1317-1322.

Rogers G N, Daniels R S, Skehel J J, Wiley D C, Wang X F, Higa H H and Paulson J C (1985) Host-mediated selection of influenza virus receptor variants. Sialic acid-alpha 2,6Gal-specific clones of A/duck/Ukraine/1/63 revert to sialic acid-alpha 2,3Gal-specific wild type in ovo. J Biol Chem 260:7362-7367.

Sanders P G, Wilson R H (1984) Amplification and cloning of the Chinese hamster glutamine synthetase gene. EMBO J. 3, 65-71.

Sandhu J S (1992) Protein Engineering of antibodies. Critical Rev Biotechnology 12, 437-462.

Schiedner G, Hertel S and Kochanek S (2000) Efficient transformation of primary human amniocytes by E1 functions of Ad5: generation of new cell lines for adenoviral vector production. Hum. Gene. Ther. 11, 2105-2116.

Shawler D L, Bartholomew R M, Smith L M and Dillman R O (1985) Human immune response to multiple injections of murine monoclonal IgG. J Immunol. 135, 1530.

Subbarao K, Klimov A, Katz J, Regnery H, Lim W, Hall H, Perdue M, Swayne D, Bender C, Huang J, Hemphill M, Rowe T, Shaw M, Xu X, Fukuda K and Cox N (1998) Characterization of an avian influenza A (H5N1) virus isolated from a child with a fatal respiratory illness. Science 279:393-396.

Suzuki Y (1994) Gangliosides as influenza virus receptors. Variation of influenza viruses and their recognition of the receptor sialo-sugar chains. Prog Lipid Res 33:429-457.

Suzuki Y, Kato H, Naeve C W and Webster R G (1989) Single-amino-acid substitution in an antigenic site of influenza virus hemagglutinin can alter the specificity of binding to cell membrane-associated gangliosides. J Virol 63:4298-4302.

Suzuki T, Portner A, Scroggs R A, Uchikawa M, Koyama N, Matsuo K, Suzuki Y and Takimoto T (2001) Receptor specificities of human respiroviruses. J Virol 75:4604-4613

Takeuchi M, Inoue N, Strickland T W, Kubota M, Wada M, Shimizu R, Hoshi S, Kozutsumi H, Takasaki S, Kobata A (1989) Relationship between sugar chain structure and biological activity of recombinant human erythropoietin produced in Chinese hamster ovary cells. Proc Natl Acad Sci USA. 86, 7819-7822.

Urlaub G, Kas E, Carothers A M, Chasin L A (1983) Deletion of the diploid dihydrofolate reductase locus from cultured mammalian cells. Cell 33, 405-412.

Vandamme A-M, Bulens F, Bernar H, Nelles L, Lijnen R H and Collen D (1990) Construction and characterization of a recombinant murine monoclonal antibody directed against human fibrin fragment-D dimer. Eur J Biochem. 192, 767-775.

Varki A, Cummings R, Esko J, Freeze H, Hart G and Marth J (1999) Essentials of glycobiology. Cold Spring Harbor Laboratory Press, Cold Spring Harbor, New York.

Vaswani S K and Hamilton R G (1998) Humanized antibodies as potential therapeutic drugs. Ann Allergy, Asthma and Immunol. 81, 105-115.

Vonach B, Hess B, Leist C (1998) Construction of a novel CHO cell line coexpressing human glucosyltransferases and fusion PSGL-1-immunoglobulin G. In: O.-W. Merten et al. (eds), New developments and new applications in animal cell technology, pp. 181-183, Kluwer Academic Publishers.

Walters R W, Yi S M, Keshavjee S, Brown K E, Welsh M J, Chiorini J A and Zabner J (2001) Binding of adeno-associated virus type 5 to 2,3-linked sialic acid is required for gene transfer. J Biol Chem 276:20610-20616.

Weikert S, Papac D, Briggs J, Cowfer D, Tom S, Gawlitzek M, Lofgren J, Mehta S, Chisholm V, Modi N, Eppler S, Carroll K, Chamow S, Peers D, Berman P, Krummen L (1999) Engineering Chinese hamster ovary cells to maximize sialic acid content of recombinant glycoproteins. Nature Biotechnology 17, 1116-1121.

White E, Sabbatini P, Debbas M, Wold W S, Kusher D I, Gooding L R (1992) The 19-kilodalton adenovirus E1B transforming protein inhibits programmed cell death and prevents cytolysis by tumor necrosis factor alpha. Mol Cell Biol. 12, 2570-2580.

Winter G, Griffiths A D, Hawkins R E and Hoogenboom H R (1994) Making antibodies by phage display technology. Annu Rev Immunol. 12, 433-455.

Wurm F, Bernard A (1999) Large-scale transient expression in mammalian cells for recombinant protein production. Curr Opin Biotechnol. 10, 156-159.

Yamaguchi K, Akai K, Kawanishi G, Ueda M, Masuda S, Sasaki R (1991) Effects of site-directed removal of N-glycosylation sites in human erythropoietin on its production and biological properties. J Biol Chem. 266, 20434-20439.

Yew P R, Berk A J (1992) Inhibition of p53 transactivation required for transformation by adenovirus early 1B protein. Nature 357, 82-85.

Zhang X, Lok S H, Kom O L (1998) Stable expression of human alpha-2,6-sialyltransferase in Chinese hamster ovary cells: functional consequences for human erythropoietin expression and bioactivity. Biochem Biophys Acta. 27, 441-452.

What is claimed is:

1. A composition comprising one or more isoforms of an erythropoietin (EPO) comprising glycans linked thereto, wherein said glycans comprise, on average,
   a) between 1 and 2 Lewis-X structures per EPO molecule, wherein, when an EPO molecule comprises 2 Lewis-X structures, said 2 Lewis-X structures are located on either the same or different glycans, and
   b) at least 6 terminal sialic acid moieties per EPO molecule, said terminal sialic acid moieties located on either the same or different glycans.

2. The composition of claim 1, wherein said glycans comprise, on average,
   a) 1-2 Lewis-X structure per EPO molecule, and
   b) at least 7 sialic acid moieties per EPO molecule.

3. The composition of claim 1, wherein said glycans comprise, on average,
   a) 1-2 Lewis-X structure per EPO molecule, and
   b) at least 8 sialic acid moieties per EPO molecule.

4. The composition of claim 1, wherein said glycans comprise, on average,
   a) between 1 and 2 Lewis-X structures per EPO molecule, and
   b) between 8 and 10 sialic acid moieties per EPO molecule.

5. A composition comprising one or more isoforms of an erythropoietin (EPO) comprising glycans linked thereto, wherein said glycans comprise, on average,
   a) at least 0.5 and no more than 2 Lewis-X structure per EPO molecule, wherein, when an EPO molecule comprises 2 Lewis-X structures, said 2 Lewis-X structures are located on either the same or different glycans linked to said EPO molecule, and
   b) at least 10 terminal sialic acid moieties per EPO molecule, wherein at least a portion of said terminal sialic acid moieties are located on different glycans.

6. The composition of claim 5, wherein said glycans comprise, on average,
   a) 0.5-2 Lewis-X structure per EPO molecule, and
   b) at least 11 sialic acid moieties per EPO molecule.

7. The composition of claim 5, wherein said glycans comprise, on average,
   a) between 0.5 and 1 Lewis-X structures per EPO molecule, and
   b) between 11 and 13 sialic acid moieties per EPO molecule.

8. The composition of claim 1, wherein said erythropoietin is human erythropoietin.

9. The composition of claim 4, wherein said erythropoietin is human erythropoietin.

10. The composition of claim 5, wherein said erythropoietin is human erythropoietin.

11. The composition of claim 7, wherein said erythropoietin is human erythropoietin.

12. The composition of claim 1, wherein said glycans comprise three N-linked glycans per EPO molecule with each N-linked glycan linked to a different asparagine residue.

13. The composition of claim 5, wherein said glycans comprise three N-linked glycans per EPO molecule with each N-linked glycan linked to a different asparagine residue.

14. The composition of claim 1, wherein said glycans comprise three N-linked glycans per EPO molecule and one O-linked glycan per EPO molecule, wherein said O-linked glycan is linked to a seine residue.

15. The composition of claim 5, wherein said glycans comprise three N-linked glycans per EPO molecule and one O-linked glycan per EPO molecule, wherein said O-linked glycan is linked to a seine residue.

16. The composition of claim 1, wherein at least one of said Lewis-X structures and at least one of said sialic acid moieties are located on the same glycan.

17. The composition of claim 1, wherein at least one said Lewis-X structures and at least one of said sialic acid moieties are located on different glycans.

18. The composition of claim 1, wherein at least one of said glycans per EPO molecule comprises an oligosaccharide having between 2 and 5 N-acetyl-glucosamine (GlcNAc) bearing branches.

19. The composition of claim 18, further comprising at least one GlcNAc covalently linked to galactose.

20. The composition of claim 19, wherein at least one galactose is covalently linked to a sialic acid via an alpha2,3- or an alpha2,6-linkage.

21. The composition of claim 19, further comprising between 1 and 2 GlcNAc modified with galactose further modified with alpha1,3-linked fucose so as to form said between 1 and 2 Lewis-X structures per EPO molecule.

22. The composition of claim 21, further comprising a galactose of one of said Lewis-X structures modified with either alpha2,3- or alpha2,6-linked sialic acid to form a sialyl-Lewis-X structure.

23. The composition of claim 18, wherein at least one GlcNAc is covalently linked to an N-acetyl-galactosamine (GalNAc).

24. The composition of claim 23, wherein at least one GalNAc is covalently linked to a sialic acid via an alpha2,6-linkage.

25. The composition of claim 23, further comprising between 1 and 2 GlcNAc covalently linked to GalNAc further covalently linked to alpha1,3-linked fucose so as to form said between 1 and 2 Lewis-X structures per EPO molecule.

26. The composition of claim 25, further comprising a GalNAc of one of said Lewis-X structures covalently linked to a sialic acid via an alpha2,6-linkage to form a sialyl-Lewis-X structure.

* * * * *

UNITED STATES PATENT AND TRADEMARK OFFICE
CERTIFICATE OF CORRECTION

PATENT NO. : 7,297,680 B2
APPLICATION NO. : 11/102073
DATED : November 20, 2007
INVENTOR(S) : Dirk J. E. Opstelten and Alphonsus G. C. M. UytdeHaag Page 1 of 1

It is certified that error appears in the above-identified patent and that said Letters Patent is hereby corrected as shown below:

On the title page:
After ITEM Related U.S. Application Data:   insert:
--(30) Foreign Application Priority Data
Oct. 29, 2001 (NL) PCT/NL01/00792
Dec. 7, 2001 (NL) PCT/NL01/00892
Jan. 25, 2002 (EP) 02075327
Apr. 19, 2002 (NL) PCT/NL02/00257--

In the claims:
CLAIM 14, COLUMN 93, LINE 20,   change "seine" to --serine--
CLAIM 15, COLUMN 93, LINE 24,   change "seine" to --serine--

Signed and Sealed this
Nineteenth Day of November, 2013

Teresa Stanek Rea
*Deputy Director of the United States Patent and Trademark Office*

SEQUENCE LISTING

<160> NUMBER OF SEQ ID NOS: 40

<210> SEQ ID NO 1
<211> LENGTH: 41
<212> TYPE: DNA
<213> ORGANISM: Artificial Sequence
<220> FEATURE:
<223> OTHER INFORMATION: PCR Primer?DHFR up, synthesized sequence

<400> SEQUENCE: 1
gatccacgtg agatctccac catggttggt tcgctaaact g           41

<210> SEQ ID NO 2
<211> LENGTH: 37
<212> TYPE: DNA
<213> ORGANISM: Artificial Sequence
<220> FEATURE:
<223> OTHER INFORMATION: PCR Primer?DHFR down, synthesized sequence

<400> SEQUENCE: 2
gatccacgtg agatctttaa tcattcttct catatac                37

<210> SEQ ID NO 3
<211> LENGTH: 85
<212> TYPE: DNA
<213> ORGANISM: Artificial Sequence
<220> FEATURE:
<223> OTHER INFORMATION: polylinker fragment, synthesized sequence,
      restriction fragment from digestion of pIPspAdapt 6 with AgeI and
      Bam HI

<400> SEQUENCE: 3
accggtgaat tcggcgcgcc gtcgacgata tcgatcggac cgacgcgttc gcgagcggcc   60
gcaattcgct agcgttaacg gatcc                                        85

<210> SEQ ID NO 4
<211> LENGTH: 86
<212> TYPE: DNA
<213> ORGANISM: Artificial Sequence
<220> FEATURE:
<223> OTHER INFORMATION: polylinker fragment, synthesized sequence,
      restriction fragment from digestion of pIPspAdapt7 with AgeI and
      Bam HI

<400> SEQUENCE: 4
accggtgaat tgcggccgct cgcgaacgcg tcggtccgta tcgatatcgt cgacggcgcg   60
ccgaattcgc tagcgttaac ggatcc                                       86

<210> SEQ ID NO 5
<211> LENGTH: 43
<212> TYPE: DNA
<213> ORGANISM: Artificial Sequence
<220> FEATURE:
<223> OTHER INFORMATION: PCR Primer?EPO?START, synthesized sequence

<400> SEQUENCE: 5
aaaaaggatc cgccaccatg ggggtgcacg aatgtcctgc ctg         43

<210> SEQ ID NO 6
<211> LENGTH: 38
<212> TYPE: DNA
<213> ORGANISM: Artificial Sequence
<220> FEATURE:
<223> OTHER INFORMATION: PCR Primer?EPO?STOP, synthesized sequence

<400> SEQUENCE: 6
aaaaaggatc ctcatctgtc ccctgtcctg caggcctc                                      38

<210> SEQ ID NO 7
<211> LENGTH: 47
<212> TYPE: DNA
<213> ORGANISM: Artificial Sequence
<220> FEATURE:
<223> OTHER INFORMATION: PCR Primer?LTR?1, synthesized sequence

<400> SEQUENCE: 7
ctgtacgtac cagtgcactg gcctaggcat ggaaaaatac ataactg                            47

<210> SEQ ID NO 8
<211> LENGTH: 64
<212> TYPE: DNA
<213> ORGANISM: Artificial Sequence
<220> FEATURE:
<223> OTHER INFORMATION: PCR Primer?LTR?2, synthesized sequence

<400> SEQUENCE: 8
gcggatcctt cgaaccatgg taagcttggt accgctagcg ttaaccgggc gactcagtca              60
atcg                                                                           64

<210> SEQ ID NO 9
<211> LENGTH: 28
<212> TYPE: DNA
<213> ORGANISM: Artificial Sequence
<220> FEATURE:
<223> OTHER INFORMATION: PCR Primer?HSA1, synthesized sequence

<400> SEQUENCE: 9
gcgccaccat gggcagagcg atggtggc                                                 28

<210> SEQ ID NO 10
<211> LENGTH: 50
<212> TYPE: DNA
<213> ORGANISM: Artificial Sequence
<220> FEATURE:
<223> OTHER INFORMATION: PCR Primer?HSA2, synthesized sequence

<400> SEQUENCE: 10
gttagatcta agcttgtcga catcgatcta ctaacagtag agatgtagaa                         50

<210> SEQ ID NO 11
<211> LENGTH: 10
<212> TYPE: DNA
<213> ORGANISM: Artificial Sequence
<220> FEATURE:
<223> OTHER INFORMATION: Oligonucleotide, synthesized sequence, EcoRI
      linker

<400> SEQUENCE: 11
ttaagtcgac                                                                     10

<210> SEQ ID NO 12
<211> LENGTH: 10
<212> TYPE: DNA
<213> ORGANISM: Artificial Sequence
<220> FEATURE:
<223> OTHER INFORMATION: oligonucleotide, synthesized sequence, EcoRI
      linker

<400> SEQUENCE: 12
ttaagtcgac                                                           10

<210> SEQ ID NO 13
<211> LENGTH: 23
<212> TYPE: DNA
<213> ORGANISM: Artificial Sequence
<220> FEATURE:
<223> OTHER INFORMATION: oligonucleotide, synthesized sequence, PacI
      linker

<400> SEQUENCE: 13
aattgtctta attaaccgct taa                                            23

<210> SEQ ID NO 14
<211> LENGTH: 67
<212> TYPE: DNA
<213> ORGANISM: Artificial Sequence
<220> FEATURE:
<223> OTHER INFORMATION: oligonucleotide, synthesized sequence, PLL?1

<400> SEQUENCE: 14
gccatcccta ggaagcttgg taccggtgaa ttcgctagcg ttaacggatc ctctagacga    60
gatctgg                                                              67

<210> SEQ ID NO 15
<211> LENGTH: 67
<212> TYPE: DNA
<213> ORGANISM: Artificial Sequence
<220> FEATURE:
<223> OTHER INFORMATION: oligonucleotide, synthesized sequence, PLL?2

<400> SEQUENCE: 15
ccagatctcg tctagaggat ccgttaacgc tagcgaattc accggtacca agcttcctag    60
ggatggc                                                              67

<210> SEQ ID NO 16
<211> LENGTH: 39
<212> TYPE: DNA
<213> ORGANISM: Artificial Sequence
<220> FEATURE:
<223> OTHER INFORMATION: PCR Primer?CMVplus, synthesized sequence

<400> SEQUENCE: 16
gatcggtacc actgcagtgg tcaatattgg ccattagcc                           39

<210> SEQ ID NO 17
<211> LENGTH: 29
<212> TYPE: DNA
<213> ORGANISM: Artificial Sequence
<220> FEATURE:
<223> OTHER INFORMATION: PCR Primer?CMVminA, synthesized sequence

<400> SEQUENCE: 17
gatcaagctt ccaatgcacc gttcccggc                                      29

<210> SEQ ID NO 18
<211> LENGTH: 34
<212> TYPE: DNA
<213> ORGANISM: Artificial Sequence
<220> FEATURE:
<223> OTHER INFORMATION: PCR Primer?CAMH?UP, synthesized sequence

<400> SEQUENCE: 18
gatcgatatc gctagcacca agggcccatc ggtc                                34

<210> SEQ ID NO 19
<211> LENGTH: 30
<212> TYPE: DNA
<213> ORGANISM: Artificial Sequence
<220> FEATURE:
<223> OTHER INFORMATION: PCR Primer?CAMH?DOWN, synthesized sequence

<400> SEQUENCE: 19
gatcgtttaa actcatttac ccggagacag                              30

<210> SEQ ID NO 20
<211> LENGTH: 28
<212> TYPE: DNA
<213> ORGANISM: Artificial Sequence
<220> FEATURE:
<223> OTHER INFORMATION: PCR Primer?CAML?UP, synthesized sequence

<400> SEQUENCE: 20
gatccgtacg gtggctgcac catctgtc                                28

<210> SEQ ID NO 21
<211> LENGTH: 31
<212> TYPE: DNA
<213> ORGANISM: Artificial Sequence
<220> FEATURE:
<223> OTHER INFORMATION: PCR Primer?CAML?DOWN, synthesized sequence

<400> SEQUENCE: 21
gatcgtttaa acctaacact ctcccctgtt g                            31

<210> SEQ ID NO 22
<211> LENGTH: 20
<212> TYPE: PRT
<213> ORGANISM: Artificial Sequence
<220> FEATURE:
<223> OTHER INFORMATION: leader peptide sequence, synthesized sequence

<400> SEQUENCE: 22

Met Ala Cys Pro Gly Phe Leu Trp Ala Leu Val Ile Ser Thr Cys Leu
1               5                   10                  15

Glu Phe Ser Met
            20

<210> SEQ ID NO 23
<211> LENGTH: 60
<212> TYPE: DNA
<213> ORGANISM: Artificial Sequence
<220> FEATURE:
<223> OTHER INFORMATION: oligonucleotide?leader peptide coding sequence,
      synthesized sequence

<400> SEQUENCE: 23
atggcatgcc ctggcttcct gtgggcactt gtgatctcca cctgtcttga attttccatg    60

<210> SEQ ID NO 24
<211> LENGTH: 38
<212> TYPE: DNA
<213> ORGANISM: Artificial Sequence
<220> FEATURE:
<223> OTHER INFORMATION: PCR Primer?UBS?UP, synthesized sequence

<400> SEQUENCE: 24
gatcacgcgt gctagccacc atggcatgcc ctggcttc                     38

<210> SEQ ID NO 25

```
<211> LENGTH: 20
<212> TYPE: PRT
<213> ORGANISM: Artificial Sequence
<220> FEATURE:
<223> OTHER INFORMATION: leader peptide, synthesized sequence

<400> SEQUENCE: 25

Met Ala Cys Pro Gly Phe Leu Trp Ala Leu Val Ile Ser Thr Cys Leu
1               5                   10                  15

Glu Phe Ser Met
            20

<210> SEQ ID NO 26
<211> LENGTH: 60
<212> TYPE: DNA
<213> ORGANISM: Artificial Sequence
<220> FEATURE:
<223> OTHER INFORMATION: oligonucleotide?leader peptide coding sequence,
      synthesized sequence

<400> SEQUENCE: 26
atggcatgcc ctggcttcct gtgggcactt gtgatctcca cctgtcttga attttccatg      60

<210> SEQ ID NO 27
<211> LENGTH: 28
<212> TYPE: DNA
<213> ORGANISM: Artificial Sequence
<220> FEATURE:
<223> OTHER INFORMATION: oligonucleotide, synthesized sequence, PCR
      product generated using primers UBS?UP and UBSHV?DOWN on template
      pNUT?Cgamma

<400> SEQUENCE: 27
gatcgctagc tgtcgagacg gtgaccag                                         28

<210> SEQ ID NO 28
<211> LENGTH: 29
<212> TYPE: DNA
<213> ORGANISM: Artificial Sequence
<220> FEATURE:
<223> OTHER INFORMATION: oligonucleotide, synthesized sequence, PCR
      product generated using primers UBS?UP and UBSLV?DOWN on template
      pNUT?Ckappa

<400> SEQUENCE: 28
gatccgtacg cttgatctcc accttggtc                                        29

<210> SEQ ID NO 29
<211> LENGTH: 50
<212> TYPE: DNA
<213> ORGANISM: Artificial Sequence
<220> FEATURE:
<223> OTHER INFORMATION: PCR Primer?15C5?UP, synthesized sequence

<400> SEQUENCE: 29
gatcacgcgt gctagccacc atgggtactc ctgctcagtt tcttggaatc                 50

<210> SEQ ID NO 30
<211> LENGTH: 41
<212> TYPE: DNA
<213> ORGANISM: Artificial Sequence
<220> FEATURE:
<223> OTHER INFORMATION: PCR Primer?HA1 forward primer, synthesized
      sequence

<400> SEQUENCE: 30
attggcgcgc caccatgaag actatcattg ctttgagcta c                          41
```

-continued

<210> SEQ ID NO 31
<211> LENGTH: 39
<212> TYPE: DNA
<213> ORGANISM: Artificial Sequence
<220> FEATURE:
<223> OTHER INFORMATION: PCR Primer?HA1 reverse primer, synthesized
      sequence

<400> SEQUENCE: 31
gatgctagct catctagttt gttttctgg tatattccg                              39

<210> SEQ ID NO 32
<211> LENGTH: 42
<212> TYPE: DNA
<213> ORGANISM: Artificial Sequence
<220> FEATURE:
<223> OTHER INFORMATION: PCR Primer?HA2 reverse primer, synthesized
      sequence

<400> SEQUENCE: 32
gatgctagct cagtctttgt atcctgactt cagttcaaca cc                         42

<210> SEQ ID NO 33
<211> LENGTH: 39
<212> TYPE: DNA
<213> ORGANISM: Artificial: chemically synthesized sequence
<220> FEATURE:
<223> OTHER INFORMATION: Forward primer for human alpha2,6
      sialyltransferase

<400> SEQUENCE: 33 tttttggat ccatgattca caccaacctg aagaaaaag                              39

<210> SEQ ID NO 34
<211> LENGTH: 35
<212> TYPE: DNA
<213> ORGANISM: Artificial: chemically synthesized sequence
<220> FEATURE:
<223> OTHER INFORMATION: Reverse primer for human alpha2,6
      sialyltransferase

<400> SEQUENCE: 34
tttttcctta agttagcagt gaatggtccg gaagc                                 35

<210> SEQ ID NO 35
<211> LENGTH: 36
<212> TYPE: DNA
<213> ORGANISM: Artificial: chemically synthesized sequence
<220> FEATURE:
<223> OTHER INFORMATION: Forward primer for human alpha2,3
      sialyltransferase

<400> SEQUENCE: 35 tttttggat ccatgtgtcc tgcaggctgg aagctc                                 36

<210> SEQ ID NO 36
<211> LENGTH: 38
<212> TYPE: DNA
<213> ORGANISM: Artificial: chemically synthesized sequence
<220> FEATURE:
<223> OTHER INFORMATION: Reverse primer for human alpha2,3
      sialyltransferase

<400> SEQUENCE: 36
tttttcctta agtcagaagg acgtgaggtt cttgatag                              38

```
<210> SEQ ID NO 37
<211> LENGTH: 34
<212> TYPE: DNA
<213> ORGANISM: Artificial: chemically synthesized sequence
<220> FEATURE:
<223> OTHER INFORMATION: Forward primer

<400> SEQUENCE: 37
ccaggcgcgc caccatgggg gtgcacgaat gtcc                              34

<210> SEQ ID NO 38
<211> LENGTH: 30
<212> TYPE: DNA
<213> ORGANISM: Artificial: chemically synthesized sequence
<220> FEATURE:
<223> OTHER INFORMATION: Reverse primer

<400> SEQUENCE: 38
ccgggttaac tcatctgtcc cctgtcctgc                                   30

<210> SEQ ID NO 39
<211> LENGTH: 23
<212> TYPE: DNA
<213> ORGANISM: Artificial: chemically synthesized sequence
<220> FEATURE:
<223> OTHER INFORMATION: Forward primer

<400> SEQUENCE: 39
ggactagtgg atccgccacc atg                                          23

<210> SEQ ID NO 40
<211> LENGTH: 30
<212> TYPE: DNA
<213> ORGANISM: Artificial: chemically synthesized sequence
<220> FEATURE:
<223> OTHER INFORMATION: Reverse primer

<400> SEQUENCE: 40
gctctagatc agaaggacgt gaggttcttg                                   30
```